US011669790B2

(12) United States Patent
Lyman et al.

(10) Patent No.: US 11,669,790 B2
(45) Date of Patent: *Jun. 6, 2023

(54) INTENSITY TRANSFORM AUGMENTATION SYSTEM AND METHODS FOR USE THEREWITH

(71) Applicant: Enlitic, Inc., San Francisco, CA (US)

(72) Inventors: Kevin Lyman, Fords, NJ (US); Li Yao, San Francisco, CA (US); Eric C. Poblenz, Palo Alto, CA (US); Jordan Prosky, San Francisco, CA (US); Ben Covington, Berkeley, CA (US); Anthony Upton, Malvern (AU)

(73) Assignee: Enlitic, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/336,648

(22) Filed: Jun. 2, 2021

(65) Prior Publication Data

US 2021/0295966 A1 Sep. 23, 2021

Related U.S. Application Data

(63) Continuation of application No. 16/360,275, filed on Mar. 21, 2019, now Pat. No. 11,056,220.

(Continued)

(51) Int. Cl.
*G06Q 10/0631* (2023.01)
*G16H 10/60* (2018.01)
(Continued)

(52) U.S. Cl.
CPC ..... *G06Q 10/06315* (2013.01); *A61B 5/7264* (2013.01); *G06F 3/0482* (2013.01);
(Continued)

(58) Field of Classification Search
CPC ........ G16H 10/60; G16H 10/20; G16H 15/00; G16H 30/20; G16H 30/40; G16H 40/20;
(Continued)

(56) References Cited

U.S. PATENT DOCUMENTS 6,466,687 B1 10/2002 Uppaluri
6,524,246 B1 2/2003 Kelly
(Continued)

FOREIGN PATENT DOCUMENTS

CN 106295139 A 1/2017
CN 106551704 A 4/2017
(Continued)

OTHER PUBLICATIONS

Andersch, Michael; Inference: the Next Step in GPU-Accelerated Deep Learning; https://devblogs.nvidia.com/parallelforall/inference-next-step-gpu-accelerated-deep-learning/; Nov. 11, 2015; 7 pages.

(Continued)

*Primary Examiner* — Xuemei G Chen
(74) *Attorney, Agent, or Firm* — Cochran Freund & Young LLC

(57) ABSTRACT

An intensity transform augmentation system is operable to generate a plurality of sets of augmented images by performing a set of intensity transformation functions on each of a training set of medical scans. Each of the set of intensity transformation functions are based on density properties of corresponding anatomy feature present in the training set of medical scans. A computer vision model is generated by performing a training step on the plurality of sets of augmented images, where each augmented image of a set of augmented images is assigned same output label data based on a corresponding one of the training set of medical scans. Inference data is generated by performing an inference function on a new medical scan by utilizing the computer (Continued)

vision model on the new medical scan. The inference data is transmitted to a client device for display via a display device.

20 Claims, 30 Drawing Sheets

Related U.S. Application Data

(60) Provisional application No. 62/770,334, filed on Nov. 21, 2018.

(51) Int. Cl.

| | |
|---|---|
| *G16H 30/40* | (2018.01) |
| *G16H 15/00* | (2018.01) |
| *G06T 5/00* | (2006.01) |
| *G06T 5/50* | (2006.01) |
| *G06T 7/00* | (2017.01) |
| *G06T 11/00* | (2006.01) |
| *G06N 5/04* | (2023.01) |
| *G16H 30/20* | (2018.01) |
| *G06N 20/00* | (2019.01) |
| *G06F 9/54* | (2006.01) |
| *G06T 7/187* | (2017.01) |
| *G06T 7/11* | (2017.01) |
| *G06F 3/0482* | (2013.01) |
| *G06T 3/40* | (2006.01) |
| *A61B 5/00* | (2006.01) |
| *G16H 50/20* | (2018.01) |
| *G06F 21/62* | (2013.01) |
| *G06Q 20/14* | (2012.01) |
| *G16H 40/20* | (2018.01) |
| *G06F 3/0484* | (2022.01) |
| *G16H 10/20* | (2018.01) |
| *G06N 5/045* | (2023.01) |
| *G06T 7/10* | (2017.01) |
| *G06T 11/20* | (2006.01) |
| *G06F 16/245* | (2019.01) |
| *G06T 7/44* | (2017.01) |
| *G06N 20/20* | (2019.01) |
| *H04L 67/12* | (2022.01) |
| *H04L 67/01* | (2022.01) |
| *G06V 10/82* | (2022.01) |
| *G06F 18/40* | (2023.01) |
| *G06F 18/214* | (2023.01) |
| *G06F 18/21* | (2023.01) |
| *G06F 18/2115* | (2023.01) |
| *G06F 18/2415* | (2023.01) |
| *G06V 10/25* | (2022.01) |
| *G06V 30/19* | (2022.01) |
| *G06V 10/764* | (2022.01) |
| *G06V 40/16* | (2022.01) |
| *G06V 10/22* | (2022.01) |
| *G16H 50/70* | (2018.01) |
| *G06T 7/70* | (2017.01) |
| *G16H 50/30* | (2018.01) |
| *A61B 5/055* | (2006.01) |
| *A61B 6/03* | (2006.01) |
| *A61B 8/00* | (2006.01) |
| *A61B 6/00* | (2006.01) |
| *G06Q 50/22* | (2018.01) |
| *G06F 40/295* | (2020.01) |
| *G06F 18/24* | (2023.01) |
| *G06F 18/2111* | (2023.01) |
| *G06V 30/194* | (2022.01) |

(52) U.S. Cl.
CPC ............ *G06F 3/0484* (2013.01); *G06F 9/542* (2013.01); *G06F 16/245* (2019.01); *G06F 18/214* (2023.01); *G06F 18/217* (2023.01); *G06F 18/2115* (2023.01); *G06F 18/2415* (2023.01); *G06F 18/41* (2023.01); *G06F 21/6254* (2013.01); *G06N 5/04* (2013.01); *G06N 5/045* (2013.01); *G06N 20/00* (2019.01); *G06N 20/20* (2019.01); *G06Q 20/14* (2013.01); *G06T 3/40* (2013.01); *G06T 5/002* (2013.01); *G06T 5/008* (2013.01); *G06T 5/50* (2013.01); *G06T 7/0012* (2013.01); *G06T 7/0014* (2013.01); *G06T 7/10* (2017.01); *G06T 7/11* (2017.01); *G06T 7/187* (2017.01); *G06T 7/44* (2017.01); *G06T 7/97* (2017.01); *G06T 11/001* (2013.01); *G06T 11/006* (2013.01); *G06T 11/206* (2013.01); *G06V 10/225* (2022.01); *G06V 10/25* (2022.01); *G06V 10/764* (2022.01); *G06V 10/82* (2022.01); *G06V 30/19173* (2022.01); *G06V 40/171* (2022.01); *G16H 10/20* (2018.01); *G16H 10/60* (2018.01); *G16H 15/00* (2018.01); *G16H 30/20* (2018.01); *G16H 30/40* (2018.01); *G16H 40/20* (2018.01); *G16H 50/20* (2018.01); *H04L 67/01* (2022.05); *H04L 67/12* (2013.01); *A61B 5/055* (2013.01); *A61B 6/032* (2013.01); *A61B 6/5217* (2013.01); *A61B 8/4416* (2013.01); *G06F 18/2111* (2023.01); *G06F 18/24* (2023.01); *G06F 40/295* (2020.01); *G06Q 50/22* (2013.01); *G06T 7/70* (2017.01); *G06T 2200/24* (2013.01); *G06T 2207/10048* (2013.01); *G06T 2207/10081* (2013.01); *G06T 2207/10088* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30004* (2013.01); *G06T 2207/30008* (2013.01); *G06T 2207/30016* (2013.01); *G06T 2207/30061* (2013.01); *G06V 30/194* (2022.01); *G06V 2201/03* (2022.01); *G16H 50/30* (2018.01); *G16H 50/70* (2018.01)

(58) Field of Classification Search
CPC ........ G16H 50/20; G16H 50/30; G16H 50/70; G16H 50/50; A61B 5/7264; A61B 5/055; A61B 6/032; A61B 6/5217; A61B 8/4416; A61B 5/7267; A61B 6/563; A61B 6/5211; A61B 6/5258; A61B 8/5207; A61B 8/5215; A61B 8/5269; A61B 6/5205; G06F 3/0482; G06F 3/0484; G06F 9/542; G06F 16/245; G06F 21/6254; G06F 40/295; G06K 9/6231; G06K 9/6254; G06K 9/6256; G06K 9/6262; G06K 9/6277; G06K 9/6229; G06K 9/6267; G06K 9/6278; G06N 5/04; G06N 5/045; G06N 20/00; G06N 20/20; G06N 3/0454; G06N 3/084; G06N 7/005; G06N 20/10; G06Q 10/06315; G06Q 20/14; G06Q 50/22; G06Q 20/145; G06T 3/40; G06T 5/002; G06T 5/008; G06T 5/50; G06T 7/0012; G06T 7/0014; G06T 7/10; G06T 7/11; G06T 7/187; G06T 7/44; G06T 7/97; G06T 11/001; G06T 11/006; G06T 11/206; G06T 7/70; G06T 2200/24; G06T 2207/10048; G06T 2207/10081; G06T 2207/10088; G06T
2207/10116; G06T 2207/10132; G06T
2207/20076; G06T 2207/20081; G06T
2207/20084; G06T 2207/30004; G06T
2207/30008; G06T 2207/30016; G06T
2207/30061; G06T 2207/10072; G06V
10/225; G06V 10/82; G06V 30/194;
G06V 2201/03; G06V 10/25; G06V
10/764; G06V 30/19173; G06V 40/171;
H04L 67/01; H04L 67/12

See application file for complete search history.

(56) References Cited

U.S. PATENT DOCUMENTS

| | | |
|---|---|---|
| 6,819,790 B2 | 11/2004 | Suzuki |
| 6,937,776 B2 | 8/2005 | Li |
| 7,123,762 B2 | 10/2006 | Giger |
| 7,418,123 B2 | 8/2008 | Giger |
| 7,813,822 B1 | 10/2010 | Hoffberg |
| 8,121,362 B2 | 2/2012 | Zhan |
| 8,303,505 B2 | 11/2012 | Webler |
| 8,331,637 B2 | 12/2012 | Bar-Aviv |
| 8,379,950 B2 | 2/2013 | Ye |
| 8,600,133 B2 | 12/2013 | Buelow et al. |
| 8,885,898 B2 | 11/2014 | Liu et al. |
| 9,165,360 B1 | 10/2015 | Bates |
| 9,349,178 B1 | 5/2016 | Itu |
| 9,501,863 B1 | 11/2016 | Fram |
| 9,569,736 B1 | 2/2017 | Ghesu |
| 9,579,518 B2 | 2/2017 | Gertner |
| 9,760,978 B1 | 9/2017 | Lu |
| 9,792,682 B2 | 10/2017 | Gluncic |
| 10,019,654 B1 | 7/2018 | Pisoni |
| 10,140,421 B1 | 11/2018 | Bernard |
| 10,304,198 B2 | 5/2019 | Yan |
| 10,340,041 B2 | 7/2019 | Chan |
| 10,540,554 B2 | 1/2020 | Guo |
| 2002/0186818 A1 | 12/2002 | Arnaud |
| 2003/0016850 A1 | 1/2003 | Kaufman |
| 2004/0064029 A1 | 4/2004 | Summers |
| 2004/0147840 A1 | 7/2004 | Duggirala |
| 2004/0181431 A1 | 9/2004 | Kuth |
| 2004/0252870 A1 | 12/2004 | Reeves |
| 2005/0027566 A1 | 2/2005 | Haskell |
| 2005/0207630 A1 | 9/2005 | Chan |
| 2005/0283450 A1 | 12/2005 | Matsugu |
| 2006/0122480 A1 | 6/2006 | Luo |
| 2007/0004980 A1 | 1/2007 | Warner |
| 2008/0004505 A1 | 1/2008 | Kapit |
| 2008/0015418 A1 | 1/2008 | Jarrell |
| 2008/0021834 A1 | 1/2008 | Holla |
| 2008/0205717 A1 | 8/2008 | Reeves |
| 2008/0243539 A1 | 10/2008 | Barish et al. |
| 2008/0267483 A1 | 10/2008 | Zhan |
| 2009/0177495 A1 | 7/2009 | Abousy |
| 2009/0222388 A1 | 9/2009 | Hua |
| 2009/0228299 A1 | 9/2009 | Kangarloo |
| 2010/0010587 A1 | 1/2010 | Skelton |
| 2010/0088117 A1 | 4/2010 | Belden |
| 2010/0278405 A1 | 11/2010 | Kakadiaris |
| 2011/0122241 A1 | 5/2011 | Wang |
| 2012/0130734 A1 | 5/2012 | White |
| 2013/0124527 A1 | 5/2013 | Lee |
| 2014/0177947 A1 | 6/2014 | Krizhevsky |
| 2014/0219500 A1 | 8/2014 | Moehrle |
| 2014/0328517 A1 | 11/2014 | Gluncic |
| 2014/0341471 A1 | 11/2014 | Ono et al. |
| 2015/0031979 A1 | 1/2015 | Rappaport et al. |
| 2015/0063667 A1 | 3/2015 | Sprencz |
| 2015/0230773 A1 | 8/2015 | Cho |
| 2015/0254843 A1 | 9/2015 | Brown |
| 2015/0305706 A1 | 10/2015 | Kanik |
| 2016/0019695 A1 | 1/2016 | Chukka |
| 2016/0027175 A1 | 1/2016 | Kim et al. |
| 2016/0048972 A1 | 2/2016 | Kam |
| 2016/0104281 A1 | 4/2016 | Grady |
| 2016/0174902 A1 | 6/2016 | Georgescu |
| 2016/0203281 A1 | 7/2016 | Zalis |
| 2016/0260211 A1 | 9/2016 | Gillies |
| 2016/0314588 A1 | 10/2016 | Harper |
| 2016/0343127 A1 | 11/2016 | Miller |
| 2016/0350914 A1 | 12/2016 | Champlin |
| 2016/0350919 A1 | 12/2016 | Steigauf |
| 2016/0364862 A1 | 12/2016 | Reicher |
| 2017/0004619 A1 | 1/2017 | Liang |
| 2017/0024517 A1 | 1/2017 | Biegert |
| 2017/0068780 A1 | 3/2017 | Dobrean |
| 2017/0109881 A1 | 4/2017 | Avendi |
| 2017/0116497 A1 | 4/2017 | Georgescu |
| 2017/0262962 A1* | 9/2017 | Rad .................. G06T 5/20 |
| 2017/0304732 A1 | 10/2017 | Velic |
| 2017/0330320 A1 | 11/2017 | Lynch |
| 2017/0337343 A1 | 11/2017 | Kakadiaris |
| 2018/0012411 A1* | 1/2018 | Richey ............... G06T 19/006 |
| 2018/0025255 A1 | 1/2018 | Poole |
| 2018/0033144 A1 | 2/2018 | Risman |
| 2018/0060535 A1 | 3/2018 | Reicher |
| 2018/0060691 A1 | 3/2018 | Bernal |
| 2018/0114092 A1* | 4/2018 | Huang ............... G06T 7/0002 |
| 2018/0114595 A1 | 4/2018 | Stern |
| 2018/0204111 A1 | 7/2018 | Zadeh |
| 2018/0260793 A1* | 9/2018 | Li ................... G06Q 40/08 |
| 2018/0286037 A1 | 10/2018 | Zaharchuk |
| 2018/0315182 A1 | 11/2018 | Rapaka |
| 2018/0342055 A1 | 11/2018 | Lyman |
| 2018/0373999 A1 | 12/2018 | Xu |
| 2019/0056496 A1 | 2/2019 | Sakai |
| 2019/0122360 A1 | 4/2019 | Zhang |
| 2019/0142519 A1 | 5/2019 | Siemionow |
| 2019/0197358 A1 | 6/2019 | Madani |
| 2019/0294961 A1 | 9/2019 | Zuev |
| 2019/0295440 A1 | 9/2019 | Hadad |
| 2019/0303686 A1* | 10/2019 | Guo .................. G06K 9/6201 |
| 2019/0378278 A1 | 12/2019 | Bose |
| 2019/0385056 A1 | 12/2019 | Girard |
| 2020/0020097 A1 | 1/2020 | Do |
| 2020/0037962 A1 | 2/2020 | Shanbhag |
| 2020/0085382 A1 | 3/2020 | Taerum |
| 2020/0167930 A1 | 5/2020 | Wang |
| 2020/0226462 A1 | 7/2020 | Maddison |
| 2020/0250794 A1 | 8/2020 | Zimmer |
| 2020/0302168 A1 | 9/2020 | Vo |
| 2020/0320682 A1 | 10/2020 | Alexander |
| 2020/0342206 A1 | 10/2020 | Jobin |
| 2020/0364501 A1 | 11/2020 | Herz |
| 2020/0364856 A1 | 11/2020 | Nicolase |
| 2020/0380675 A1 | 12/2020 | Golden |

FOREIGN PATENT DOCUMENTS

| | | |
|---|---|---|
| GB | 2457022 A | 8/2009 |
| KR | 1020100014065 A | 2/2010 |

OTHER PUBLICATIONS

Attaluri, et al.; Efficient and Accurate Abnormality Mining from Radiology Reports with Customized False Positive Reduction: arXiv:1810.000967v1; Oct. 1, 2018.

Choi, Y., Chiu, C. Y. I., & Sontag, D. (2016). Learning low-dimensional representations of medical concepts. AMIA Summits on Translational Science Proceedings, 2016, 41. (Year: 2016).

International Searching Authority; International Search Report and Written Opinion; International Application No. PCT/US2018/032927; dated Sep. 14, 2018; 9 pgs.

Jamie A. Weydert, MD, Barry R. De Young, MD and Michael B. Cohen, MD, A preliminary Diagnosis Service Provides Prospective Blinded Dual-Review of All General Surgical Pathology Cases in an Academic Practice, 2005, Am J Surg Pathol, vol. 29, pp. 801-805 (Year: 2005).

(56) References Cited

OTHER PUBLICATIONS

Long, Jonathan, Evan Shelhamer, and Trevor Darrell. "Fully convolutional networks for semantic segmentation." Proceedings of the IEEE conference on computer vision and pattern recognition. 2015. (Year: 2015).

Minnaar, Alex; Deep Learning Basics: Neural Networks, Backpropagation and Stochastic Gradient Descent; http://alexminnaar.com/deep-learning-basics-neural-networks-backpropagation-and-stochastic-gradient-descent.html Feb. 14, 2015; 11 pages.

Olah, Christopher; Calculus on Computational Graphs: Backpropagation; http://colah.github.io/posts/2015-08-Backprop/; Aug. 31, 2015; 7 pages.

Pham, A.-D., Neveol, A., Lavergne, T., Yasunaga, D., Clement, 0., Meyer, G., . . . Burgun, A. (2014). Natural language processing of radiology reports for the detection of thromboembolic diseases and clinically relevant incidental findings. BMC Bioinformatics, 15(1). doi: 10.1186/1471-2105-15-266 (Year: 2014).

Pons, E., Braun, L. M. M., Hunink, M. G. M., & Kors, J. A. (2016). Natural Language Processing in Radiology: a Systematic Review. Radiology, 279(2), 329-343. doi: 10.1148/radiol.16142770.

Pre Conference Proceedings of the 7th MICCAI BraTS Challenge (2018); BraTS Multimodal Brain Tumor Segmentation Challenge; Granada, Spain; Sep. 16, 2018; 578 pages.

Reid, Stuart; 10 misconceptions about Neural Networks; http://www.turingfinance.com/misconceptions-about-neural-networks/; May 8, 2014; 24 pages.

S. Ted Sandler, Regularlized Learning with Feature Networks (Year: 2010).

What Not to Include in a Medical Record. (Jun. 6, 2012). Retrieved from https://www.texmed.org/Template.aspx?id=1741. (Year: 2012).

Wikipedia: Backpropagation; https://en.wikipedia.org/wiki/Backpropagation#Assumptions_about_the_loss_function; downloaded from the internet on 18/15/18; 12 pages.

Wikipedia; Convolutional neural network; https://en.wikipedia.org/wiki/Convolutional_neural_network#Pooling_layer; downloaded from the internet on Jan. 15, 2018; 21 pages.

Yao, Li, et al. "Weakly supervised medical diagnosis and localization from multiple resolutions." arXiv preprint arXiv: 1803.07703 (2018). (Year: 2018).

Yoo Jae Chern, Remote medical-diagnosis system and method. 2010. Translated by IP.com (Year 2010).

\* cited by examiner

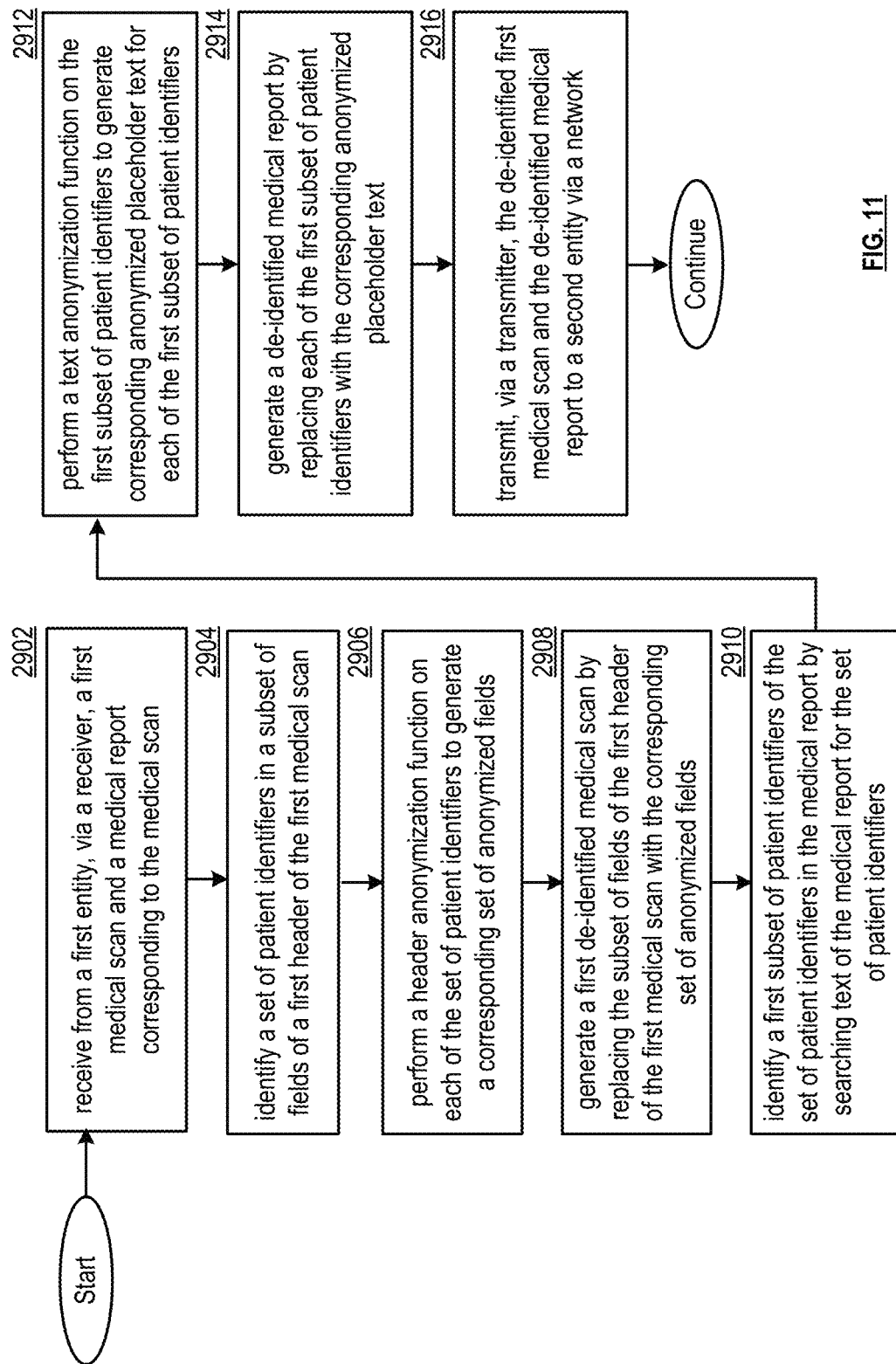

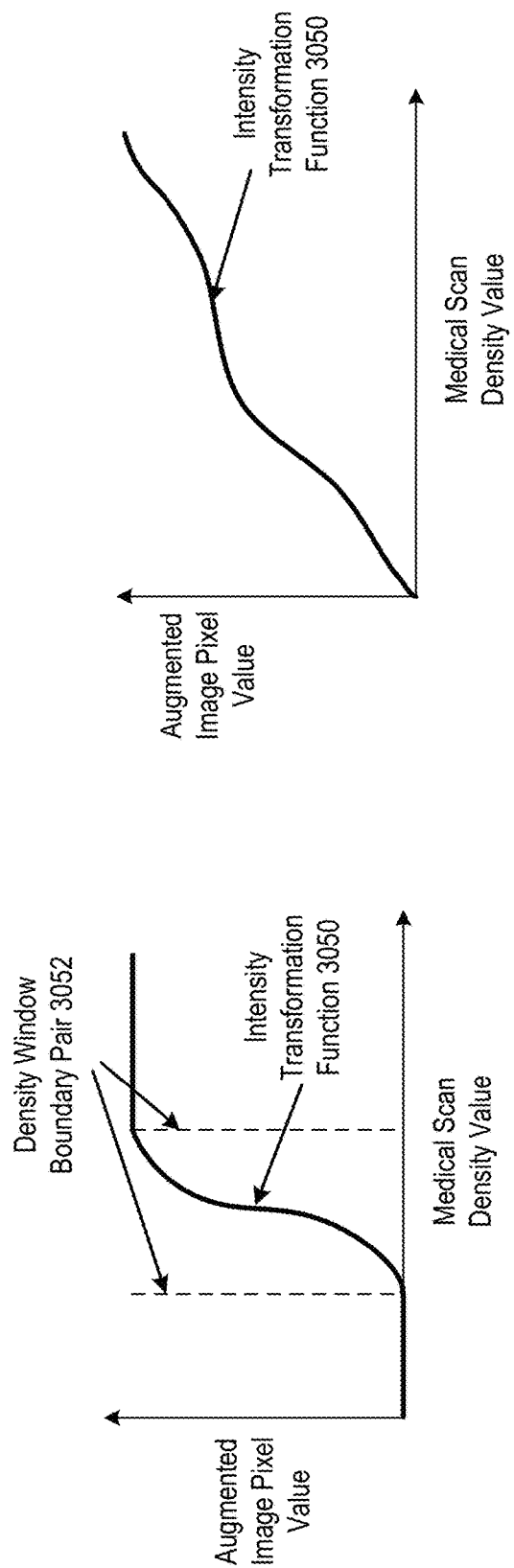
FIG. 12D
FIG. 12E
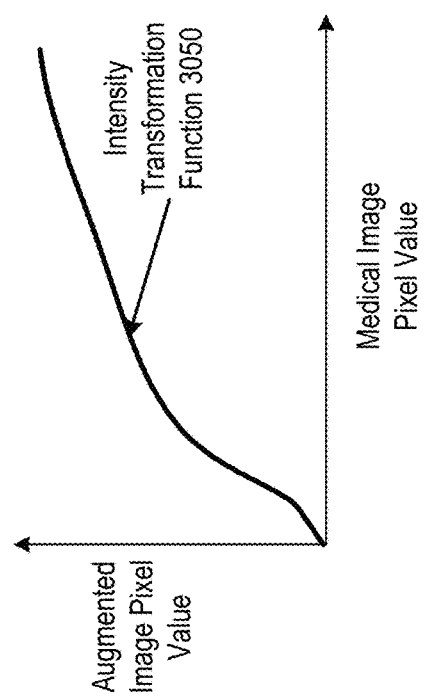
FIG. 12F

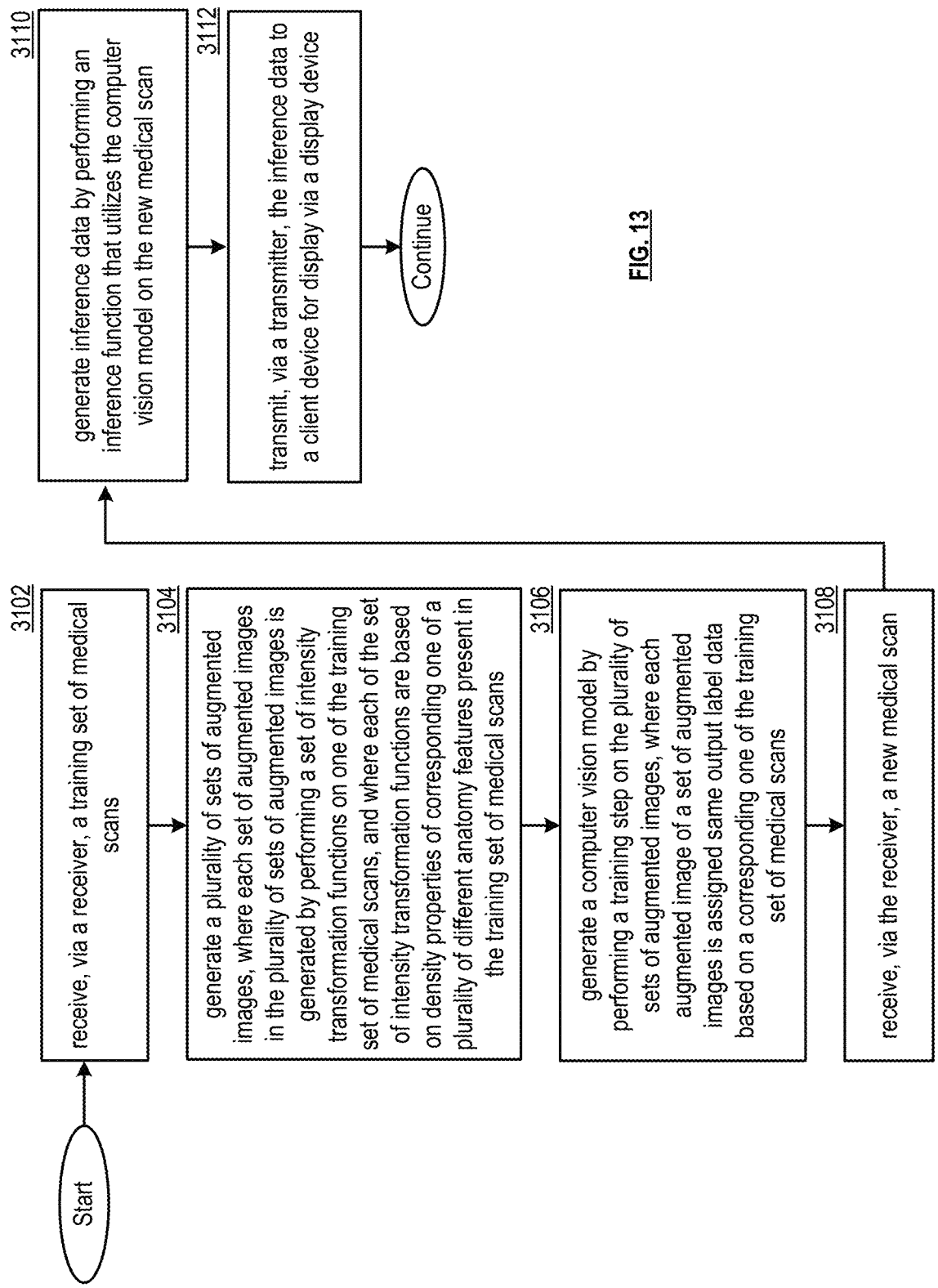

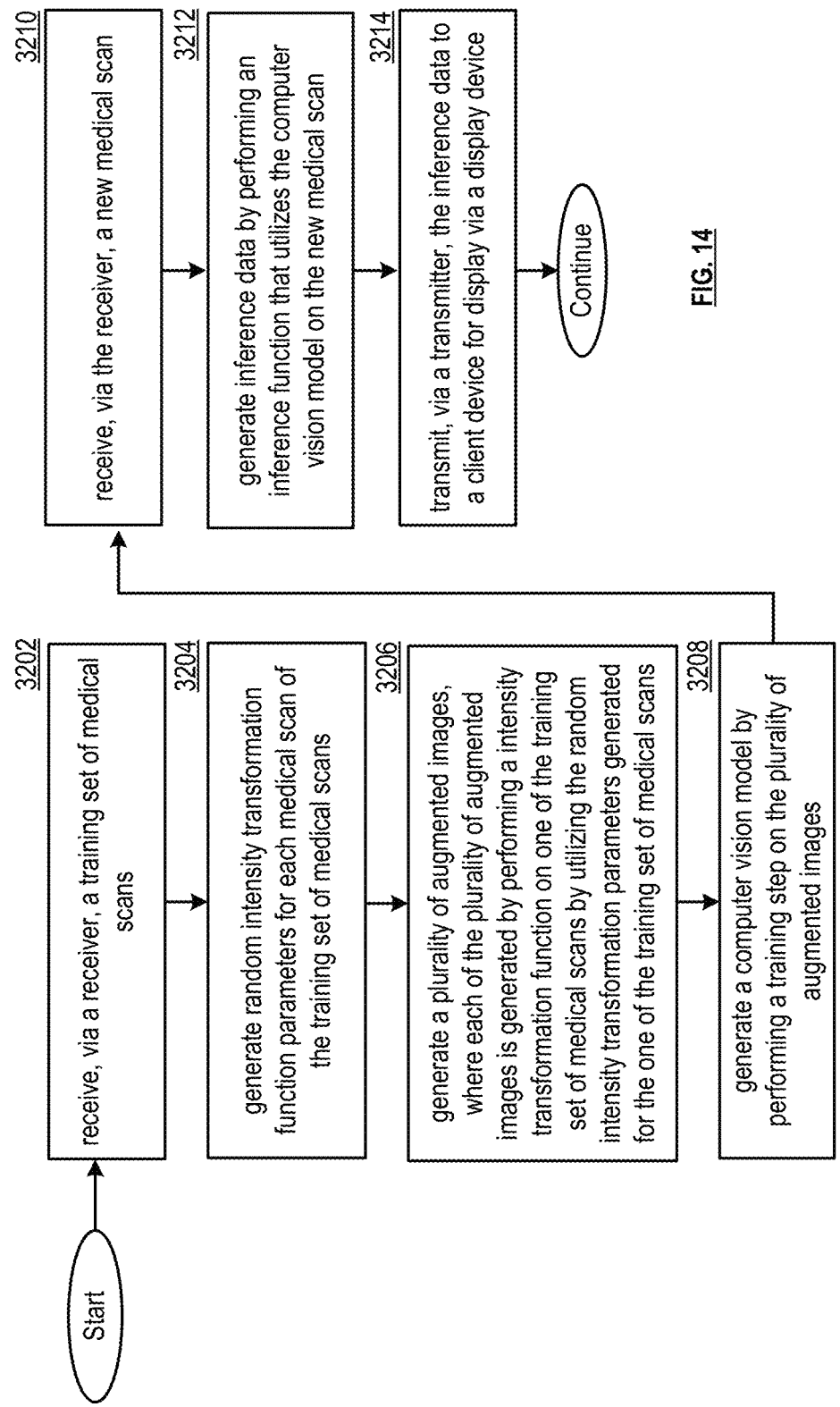

INTENSITY TRANSFORM AUGMENTATION SYSTEM AND METHODS FOR USE THEREWITH

CROSS REFERENCE TO RELATED APPLICATIONS

The present U.S. Utility patent application claims priority pursuant to 35 U.S.C. § 120 as a continuation of U.S. Utility application Ser. No. 16/360,275, entitled "UTILIZING DENSITY PROPERTIES OF ANATOMICAL FEATURES IN AN INTENSITY TRANSFORM AUGMENTATION SYSTEM", filed Mar. 21, 2019, which claims priority pursuant to 35 U.S.C. § 119(e) to U.S. Provisional Application No. 62/770,334, entitled "LESION TRACKING SYSTEM", filed Nov. 21, 2018, both of which are hereby incorporated herein by reference in their entirety and made part of the present U.S. Utility patent application for all purposes.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND

Technical Field

This invention relates generally to medical imaging devices and knowledge-based systems used in conjunction with client/server network architectures.

Description of Related Art

BRIEF DESCRIPTION OF THE SEVERAL VIEWS OF THE DRAWING(S)

Figure 12A:
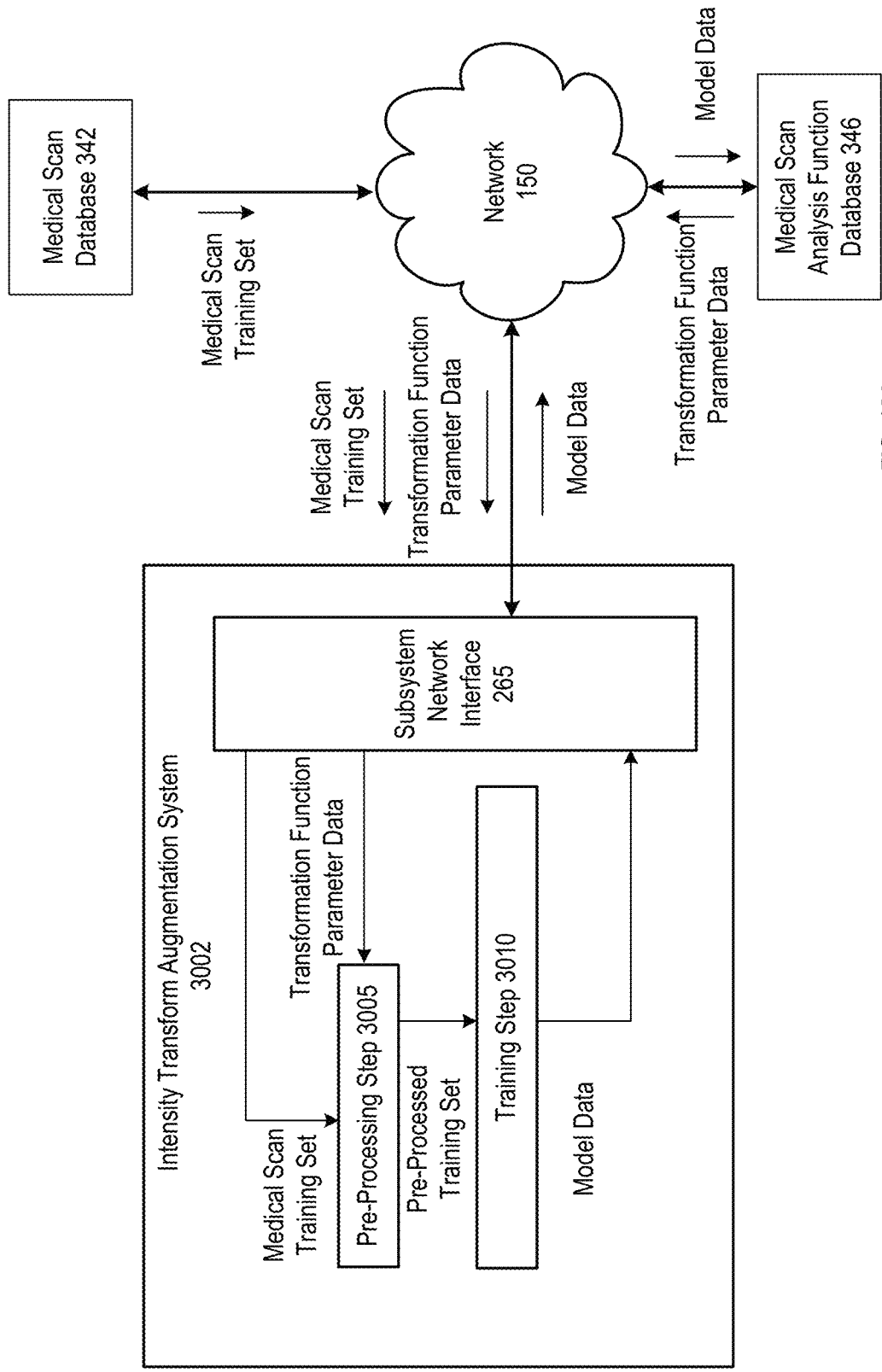
Figure 12B:
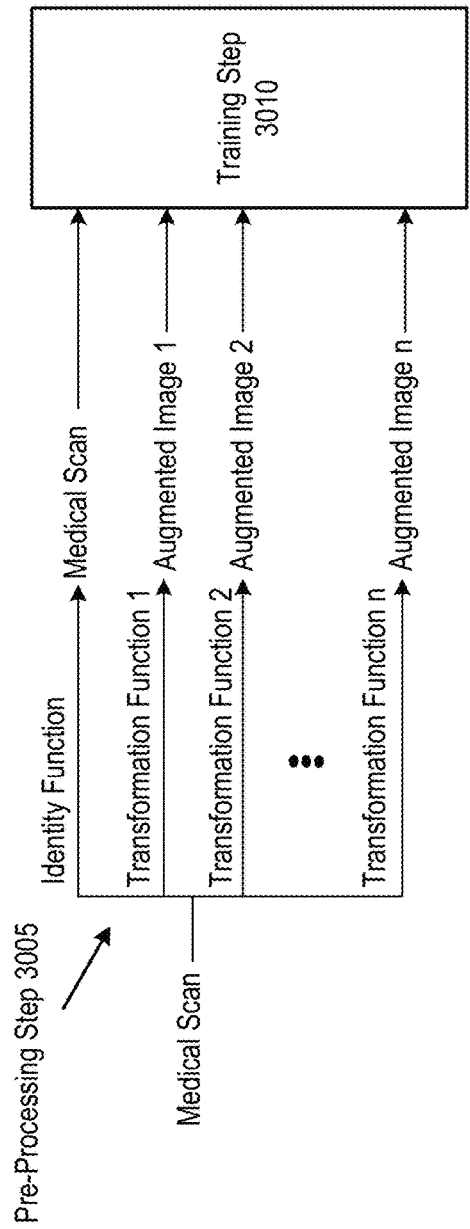
Figure 12C:
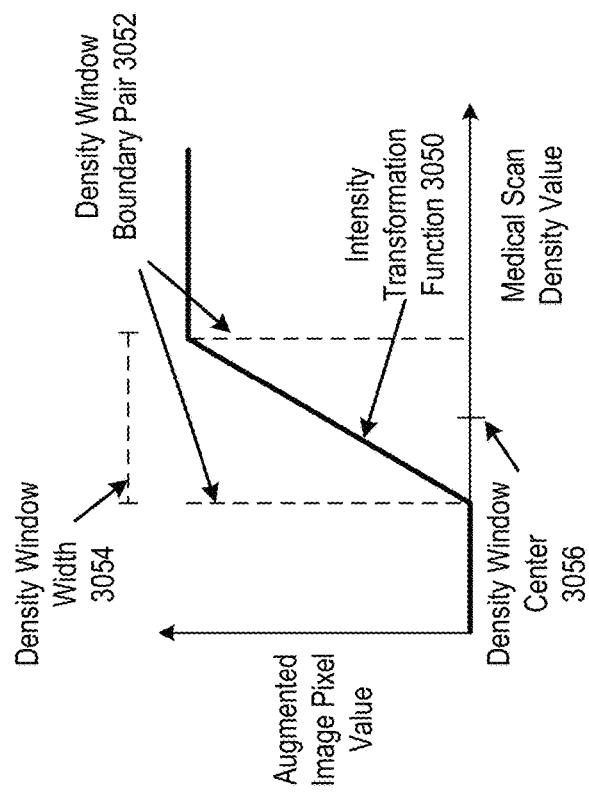
Figure 12G:
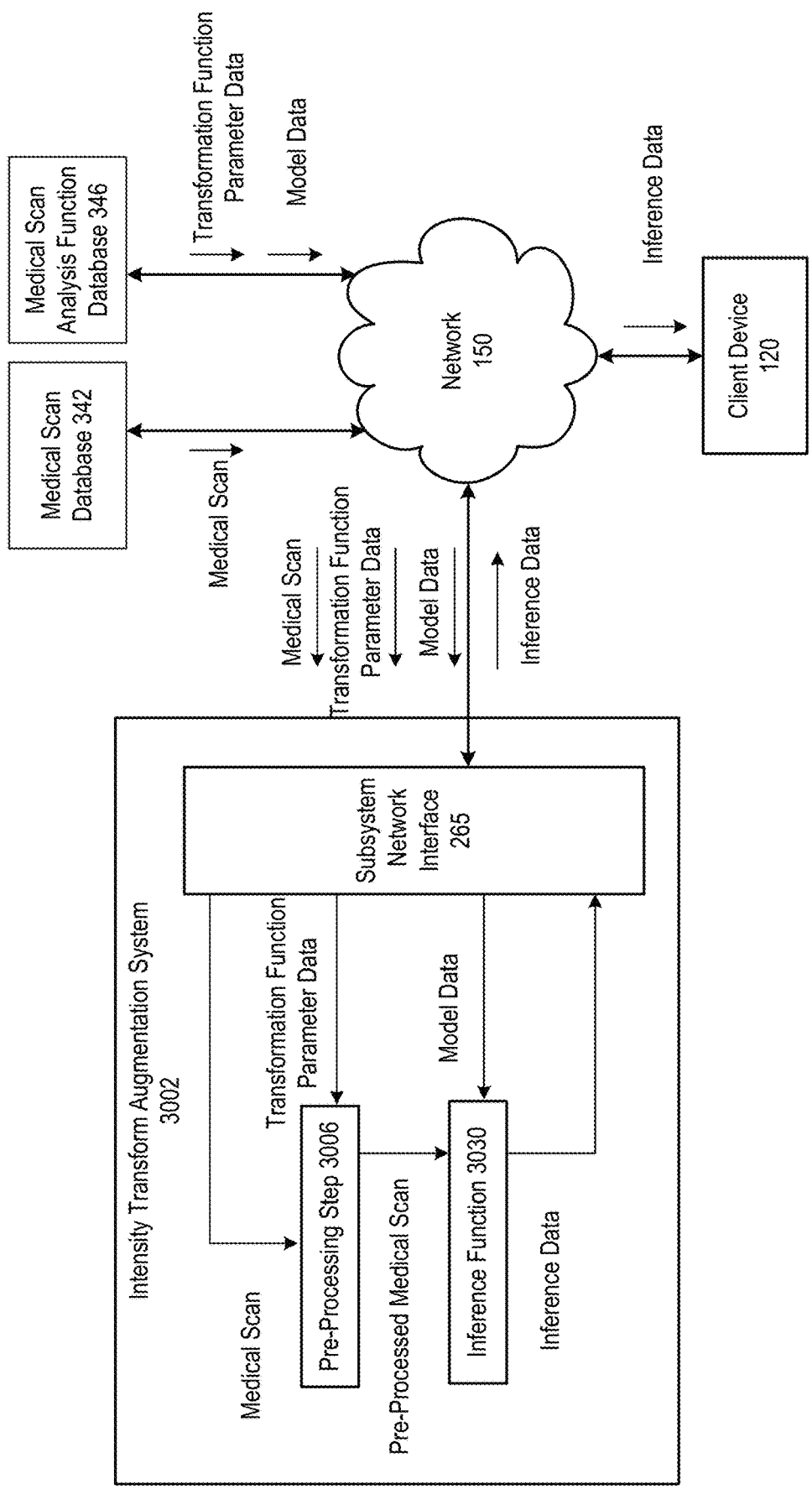
Figure 12H:
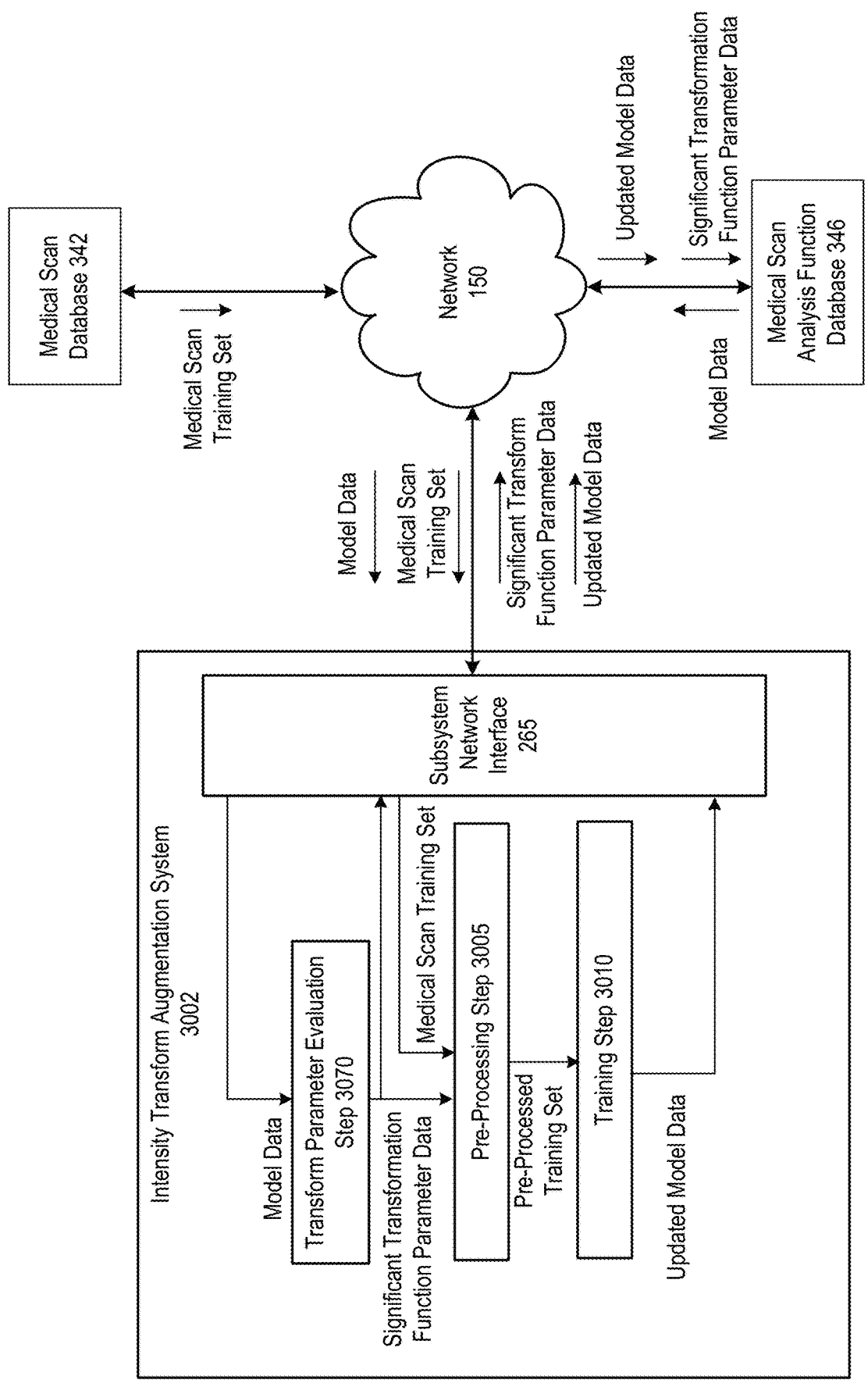
Figure 15:
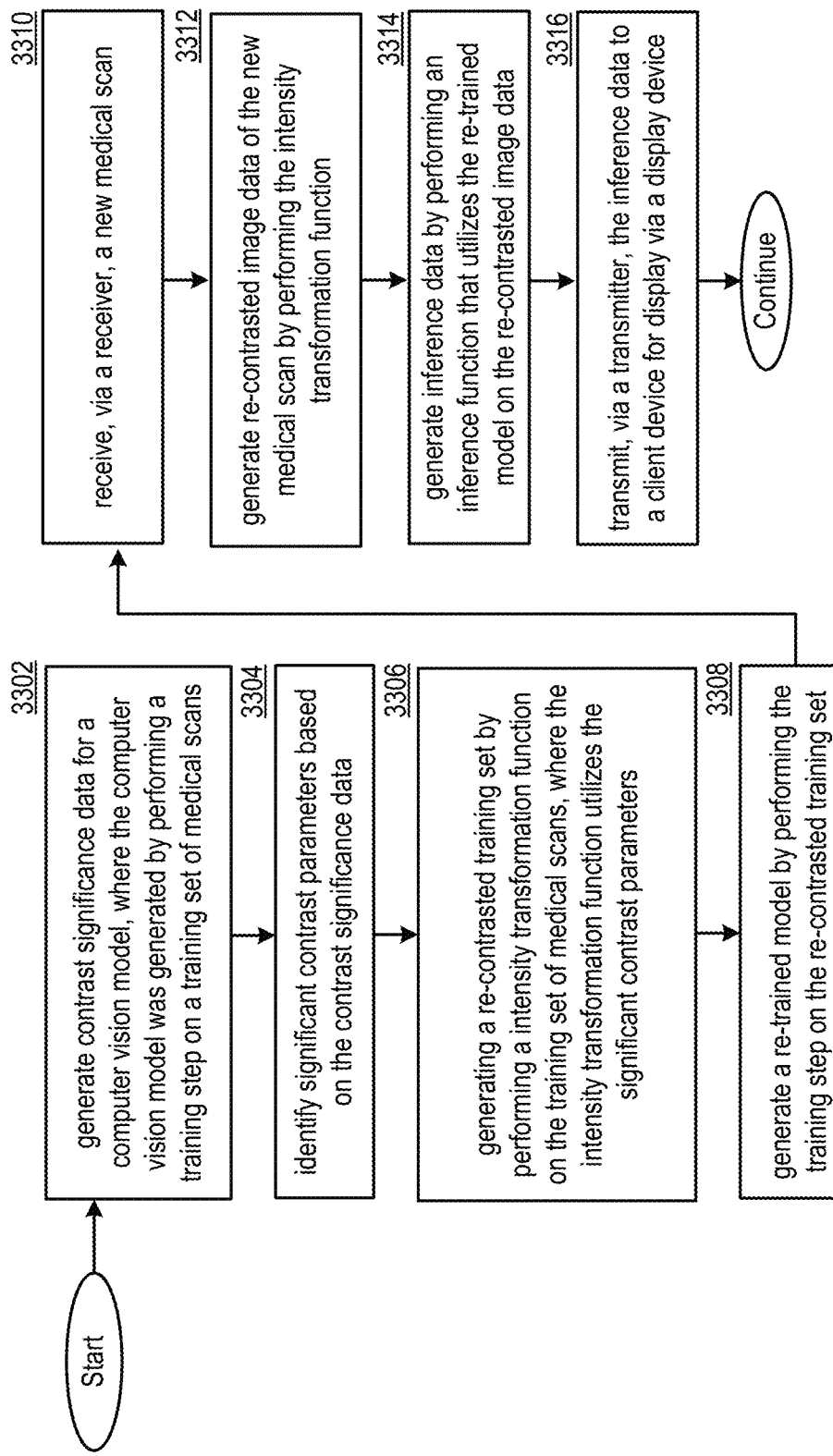

FIG. 11 presents a flowchart illustrating a method for execution by a de-identification system in accordance with various embodiments;

FIG. 12A is a schematic block diagram of an intensity transform augmentation system in accordance with various embodiments;

FIG. 12B illustrates an example of a pre-processing step utilized by an intensity transform augmentation system in accordance with various embodiments;

FIGS. 12C-12F illustrate example embodiments of intensity transformation functions utilized by an intensity transform augmentation system in accordance with various embodiments;

FIG. 12G is a schematic block diagram of an intensity transform augmentation system in accordance with various embodiments;

FIG. 12H is a schematic block diagram of an intensity transform augmentation system in accordance with various embodiments;

FIG. 13 presents a flowchart illustrating a method for execution by an intensity transform augmentation system in accordance with various embodiments;

FIG. 14 presents a flowchart illustrating a method for execution by an intensity transform augmentation system in accordance with various embodiments; and FIG. 15 presents a flowchart illustrating a method for execution by a contrast parameter learning system in accordance with various embodiments.

DETAILED DESCRIPTION

The present U.S. Utility patent application is related to U.S. Utility application Ser. No. 15/627,644, entitled "MEDICAL SCAN ASSISTED REVIEW SYSTEM", filed 20 Jun. 2017, which claims priority pursuant to 35 U.S.C. § 119(e) to U.S. Provisional Application No. 62/511,150, entitled "MEDICAL SCAN ASSISTED REVIEW SYSTEM AND METHODS", filed 25 May 2017, both of which are hereby incorporated herein by reference in their entirety and made part of the present U.S. Utility patent application for all purposes.

Figure 1:
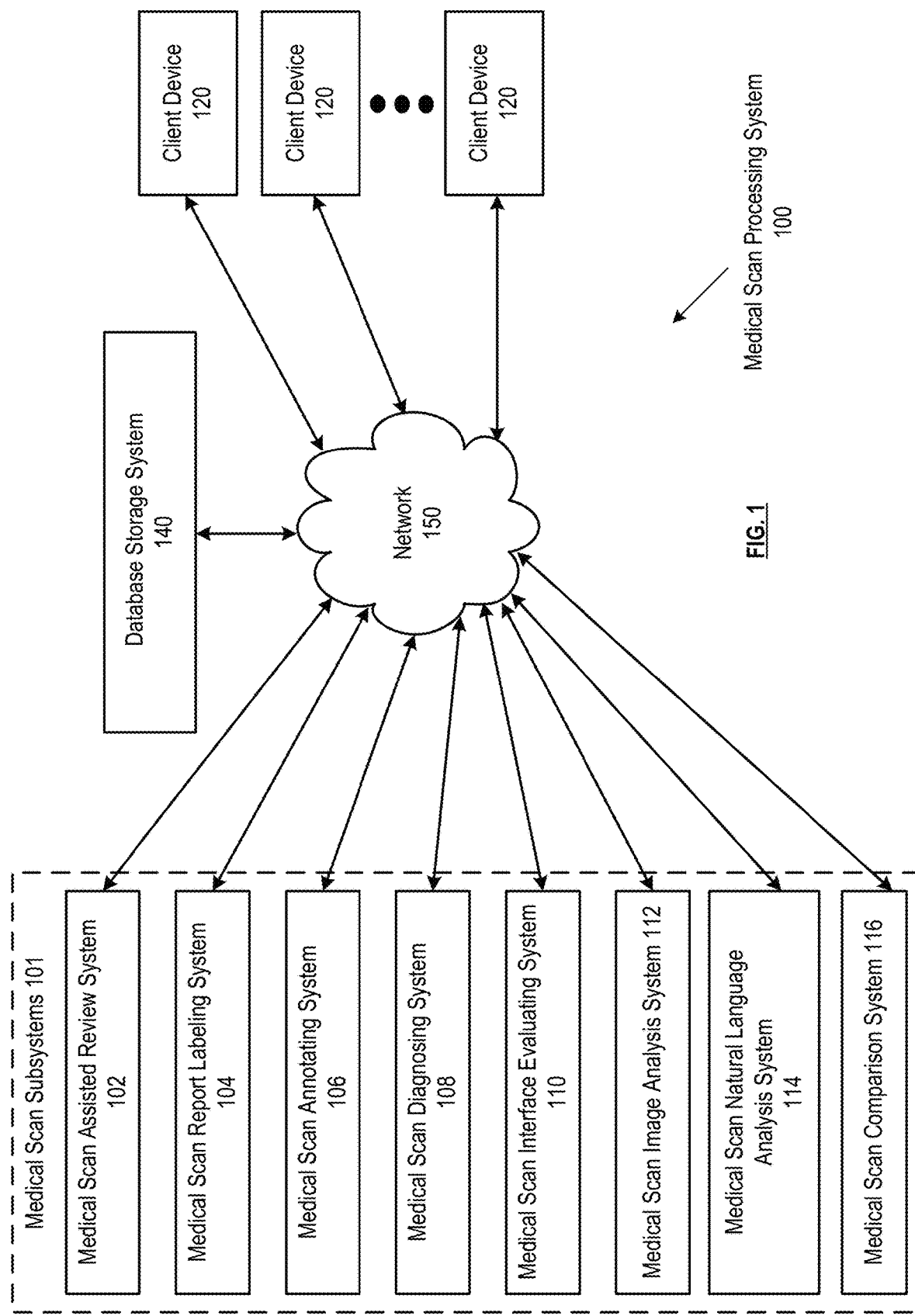
FIG. 1 is a schematic block diagram of an embodiment.

FIG. 1 presents a medical scan processing system 100, which can include one or more medical scan subsystems 101 that communicate bidirectionally with one or more client devices 120 via a wired and/or wireless network 150. The medical scan subsystems 101 can include a medical scan assisted review system 102, medical scan report labeling system 104, a medical scan annotator system 106, a medical scan diagnosing system 108, a medical scan interface feature evaluator system 110, a medical scan image analysis system 112, a medical scan natural language analysis system 114, and/or a medical scan comparison system 116. Some or all of the subsystems 101 can utilize the same processing devices, memory devices, and/or network interfaces, for example, running on a same set of shared servers connected to network 150. Alternatively or in addition, some or all of the subsystems 101 be assigned their own processing devices, memory devices, and/or network interfaces, for example, running separately on different sets of servers connected to network 150. Some or all of the subsystems 101 can interact directly with each other, for example, where one subsystem's output is transmitted directly as input to another subsystem via network 150. Network 150 can include one or more wireless and/or wired communication systems; one or more non-public intranet systems and/or public internet systems; and/or one or more local area networks (LAN) and/or wide area networks (WAN).

The medical scan processing system 100 can further include a database storage system 140, which can include one or more servers, one or more memory devices of one or more subsystems 101, and/or one or more other memory devices connected to network 150. The database storage system 140 can store one or more shared databases and/or one or more files stored on one or more memory devices that include database entries as described herein. The shared databases and/or files can each be utilized by some or all of the subsystems of the medical scan processing system, allowing some or all of the subsystems and/or client devices to retrieve, edit, add, or delete entries to the one or more databases and/or files.

The one or more client devices 120 can each be associated with one or more users of one or more subsystems of the medical scan processing system. Some or all of the client devices can be associated with hospitals or other medical institutions and/or associated with medical professionals, employees, or other individual users for example, located at one or more of the medical institutions. Some of the client devices 120 can correspond to one or more administrators of one or more subsystems of the medical scan processing system, allowing administrators to manage, supervise, or override functions of one or more subsystems for which they are responsible.

Some or all of the subsystems 101 of the medical scan processing system 100 can include a server that presents a website for operation via a browser of client devices 120. Alternatively or in addition, each client device can store application data corresponding to some or all subsystems, for example, a subset of the subsystems that are relevant to the user in a memory of the client device, and a processor of the client device can display the interactive interface based on instructions in the interface data stored in memory. For example, the website presented by a subsystem can operate via the application. Some or all of the websites presented can correspond to multiple subsystems, for example, where the multiple subsystems share the server presenting the website. Furthermore, the network 150 can be configured for secure and/or authenticated communications between the medical scan subsystems 101, the client devices 120 and the database storage system 140 to protect the data stored in the database storage system and the data communicated between the medical scan subsystems 101, the client devices 120 and the database storage system 140 from unauthorized access.

The medical scan assisted review system 102 can be used to aid medical professionals or other users in diagnosing, triaging, classifying, ranking, and/or otherwise reviewing medical scans by presenting a medical scan for review by a user by transmitting medical scan data of a selected medical scan and/or interface feature data of selected interface features of to a client device 120 corresponding to a user of the medical scan assisted review system for display via a display device of the client device. The medical scan assisted review system 102 can generate scan review data for a medical scan based on user input to the interactive interface displayed by the display device in response to prompts to provide the scan review data, for example, where the prompts correspond to one or more interface features.

The medical scan assisted review system 102 can be operable to receive, via a network, a medical scan for review. Abnormality annotation data can be generated by identifying one or more of abnormalities in the medical scan by utilizing a computer vision model that is trained on a plurality of training medical scans. The abnormality annotation data can include location data and classification data for each of the plurality of abnormalities and/or data that facilitates the visualization of the abnormalities in the scan image data. Report data including text describing each of the plurality of abnormalities is generated based on the abnormality data. The visualization and the report data, which can collectively be displayed annotation data, can be transmitted to a client device. A display device associated with the client device can display the visualization in conjunction with the medical scan via an interactive interface, and the display device can further display the report data via the interactive interface.

In various embodiments, longitudinal data, such as one or more additional scans of longitudinal data 433 of the medical scan or of similar scans, can be displayed in conjunction with the medical scan automatically, or in response to the user electing to view longitudinal data via user input. For example, the medical scan assisted review system can retrieve a previous scan or a future scan for the patient from a patient database or from the medical scan database automatically or in response to the user electing to view past patient data. One or more previous scans can be displayed in one or more corresponding windows adjacent to the current medical scan. For example, the user can select a past scan from the longitudinal data for display. Alternatively or in addition, the user can elect longitudinal parameters such as amount of time elapsed, scan type, electing to select the most recent and/or least recent scan, electing to select a future scan, electing to select a scan at a date closest to the scan, or other criteria, and the medical scan assisted review system can automatically select a previous scan that compares most favorably to the longitudinal parameters. The selected additional scan can be displayed in an adjacent window alongside the current medical scan. In some embodiments, multiple additional scans will be selected and can be displayed in multiple adjacent windows.

In various embodiments, a first window displaying an image slice 412 of the medical scan and an adjacent second window displaying an image slice of a selected additional scan will display image slices 412 determined to correspond with the currently displayed slice 412 of the medical scan. As described with respect to selecting a slice of a selected similar medical scan for display, this can be achieved based on selecting the image slice with a matching slice number, based on automatically determining the image slice that most closely matches the anatomical region corresponding to the currently displayed slice of the current scan, and/or based on determining the slice in the previous scan with the most similar view of the abnormality as the currently displayed slice. The user can use a single scroll bar or other single user input indication to jump to a different image slice, and the multiple windows can simultaneously display the same numbered image slice, or can scroll or jump by the same number of slices if different slice numbers are initially displayed. In some embodiments, three or more adjacent windows corresponding to the medical scan and two or more additional scans are displayed, and can all be controlled with the single scroll bar in a similar fashion.

The medical scan assisted review system 102 can automatically detect previous states of the identified abnormalities based on the abnormality data, such as the abnormality location data. The detected previous states of the identified abnormality can be circled, highlighted, or otherwise indicated in their corresponding window. The medical scan assisted review system 102 can retrieve classification data for the previous state of the abnormality by retrieving abnormality annotation data 442 of the similar abnormality mapped to the previous scan from the medical scan database 342. This data may not be assigned to the previous scan, and the medical scan assisted review system can automatically determine classification or other diagnosis data for the previous medical scan by utilizing the medical scan image analysis system as discussed. Alternatively or in addition, some or all of the abnormality classification data 445 or other diagnosis data 440 for the previous scan can be assigned values determined based on the abnormality classification data or other diagnosis data determined for the current scan. Such abnormality classification data 445 or other diagnosis data 440 determined for the previous scan can be mapped to the previous scan, and or mapped to the longitudinal data 433, in the database and/or transmitted to a responsible entity via the network.

The medical assisted review system can automatically generate state change data such as a change in size, volume, malignancy, or other changes to various classifiers of the abnormality. This can be achieved by automatically comparing image data of one or more previous scans and the current scan and/or by comparing abnormality data of the previous scan to abnormality data of the current scan. In some embodiments, such metrics can be calculated by utilizing the medical scan similarity analysis function, for example, where the output of the medical scan similarity analysis function such as the similarity score indicates distance, error, or other measured discrepancy in one or more abnormality classifier categories 444 and/or abnormality pattern categories 446. This calculated distance, error, or other measured discrepancy in each category can be used to quantify state change data, indicate a new classifier in one or more categories, to determine if a certain category has become more or less severe, or otherwise determine how the abnormality has changed over time. In various embodiments, this data can be displayed in one window, for example, where an increase in abnormality size is indicated by overlaying or highlighting an outline of the current abnormality over the corresponding image slice of the previous abnormality, or vice versa. In various embodiments where several past scans are available, such state change data can be determined over time, and statistical data showing growth rate changes over time or malignancy changes over time can be generated, for example, indicating if a growth rate is lessening or worsening over time. Image slices corresponding to multiple past scans can be displayed in sequence, for example, where a first scroll bar allows a user to scroll between image slice numbers, and a second scroll bar allows a user to scroll between the same image slice over time. In various embodiments the abnormality data, heat map data, or other interface features will be displayed in conjunction with the image slices of the past image data.

The medical scan report labeling system 104 can be used to automatically assign medical codes to medical scans based on user identified keywords, phrases, or other relevant medical condition terms of natural text data in a medical scan report of the medical scan, identified by users of the medical scan report labeling system 104. The medical scan report labeling system 104 can be operable to transmit a medical report that includes natural language text to a first client device for display. Identified medical condition term data can be received from the first client device in response. An alias mapping pair in a medical label alias database can be identified by determining that a medical condition term of the alias mapping pair compares favorably to the identified medical condition term data. A medical code that corresponds to the alias mapping pair and a medical scan that corresponds to the medical report can be transmitted to a second client device of an expert user for display, and accuracy data can be received from the second client device in response. The medical code is mapped to the first medical scan in a medical scan database when the accuracy data indicates that the medical code compares favorably to the medical scan.

The medical scan annotator system 106 can be used to gather annotations of medical scans based on review of the medical scan image data by users of the system such as radiologists or other medical professionals. Medical scans that require annotation, for example, that have been triaged from a hospital or other triaging entity, can be sent to multiple users selected by the medical scan annotator system 106, and the annotations received from the multiple medical professionals can be processed automatically by a processing system of the medical scan annotator system, allowing the medical scan annotator system to automatically determine a consensus annotation of each medical scan. Furthermore, the users can be automatically scored by the medical scan annotator system based on how closely their annotation matches to the consensus annotation or some other truth annotation, for example, corresponding to annotations of the medical scan assigned a truth flag. Users can be assigned automatically to annotate subsequent incoming medical scans based on their overall scores and/or based on categorized scores that correspond to an identified category of the incoming medical scan.

The medical scan annotator system 106 can be operable to select a medical scan for transmission via a network to a first client device and a second client device for display via an interactive interface, and annotation data can be received from the first client device and the second client device in response. Annotation similarity data can be generated by comparing the first annotation data to the second annotation data, and consensus annotation data can be generated based on the first annotation data and the second annotation data in response to the annotation similarity data indicating that the difference between the first annotation data and the second annotation data compares favorably to an annotation discrepancy threshold. The consensus annotation data can be mapped to the medical scan in a medical scan database.

A medical scan diagnosing system 108 can be used by hospitals, medical professionals, or other medical entities to automatically produce inference data for given medical scans by utilizing computer vision techniques and/or natural language processing techniques. This automatically generated inference data can be used to generate and/or update diagnosis data or other corresponding data of corresponding medical scan entries in a medical scan database. The medical scan diagnosing system can utilize a medical scan database, user database, and/or a medical scan analysis function database by communicating with the database storage system 140 via the network 150, and/or can utilize another medical scan database, user database, and/or function database stored in local memory.

The medical scan diagnosing system 108 can be operable to receive a medical scan. Diagnosis data of the medical scan can be generated by performing a medical scan inference function on the medical scan. The first medical scan can be transmitted to a first client device associated with a user of the medical scan diagnosing system in response to the diagnosis data indicating that the medical scan corresponds to a non-normal diagnosis. The medical scan can be displayed to the user via an interactive interface displayed by a display device corresponding to the first client device. Review data can be received from the first client device, where the review data is generated by the first client device in response to a prompt via the interactive interface. Updated diagnosis data can be generated based on the review data. The updated diagnosis data can be transmitted to a second client device associated with a requesting entity.

A medical scan interface feature evaluating system 110 can be used evaluate proposed interface features or currently used interface features of an interactive interface to present medical scans for review by medical professionals or other users of one or more subsystems 101. The medical scan interface feature evaluator system 110 can be operable to generate an ordered image-to-prompt mapping by selecting a set of user interface features to be displayed with each of an ordered set of medical scans. The set of medical scans and the ordered image-to-prompt mapping can be transmitted to a set of client devices. A set of responses can be generated by each client device in response to sequentially displaying each of the set of medical scans in conjunction with a mapped user interface feature indicated in the ordered image-to-prompt mapping via a user interface. Response score data can be generated by comparing each response to truth annotation data of the corresponding medical scan. Interface feature score data corresponding to each user interface feature can be generated based on aggregating the response score data, and is used to generate a ranking of the set of user interface features.

A medical scan image analysis system 112 can be used to generate and/or perform one or more medical scan image analysis functions by utilizing a computer vision-based learning algorithm 1350 on a training set of medical scans with known annotation data, diagnosis data, labeling and/or medical code data, report data, patient history data, patient risk factor data, and/or other metadata associated with medical scans. These medical scan image analysis functions can be used to generate inference data for new medical scans that are triaged or otherwise require inferred annotation data, diagnosis data, labeling and/or medical code data, and/or report data. For example, some medical scan image analysis functions can correspond to medical scan inference functions of the medical scan diagnosing system or other medical scan analysis functions of a medical scan analysis function database. The medical scan image analysis functions can be used to determine whether or not a medical scan is normal, to detect the location of an abnormality in one or more slices of a medical scan, and/or to characterize a detected abnormality. The medical scan image analysis system can be used to generate and/or perform computer vision based medical scan image analysis functions utilized by other subsystems of the medical scan processing system as described herein, aiding medical professionals to diagnose patients and/or to generate further data and models to characterize medical scans. The medical scan image analysis system can include a processing system that includes a processor and a memory that stores executable instructions that, when executed by the processing system, facilitate performance of operations.

The medical scan image analysis system 112 can be operable to receive a plurality of medical scans that represent a three-dimensional anatomical region and include a plurality of cross-sectional image slices. A plurality of three-dimensional subregions corresponding to each of the plurality of medical scans can be generated by selecting a proper subset of the plurality of cross-sectional image slices from each medical scan, and by further selecting a two-dimensional subregion from each proper subset of cross-sectional image slices. A learning algorithm can be performed on the plurality of three-dimensional subregions to generate a neural network. Inference data corresponding to a new medical scan received via the network can be generated by performing an inference algorithm on the new medical scan by utilizing the neural network. An inferred abnormality can be identified in the new medical scan based on the inference data.

The medical scan natural language analysis system 114 can determine a training set of medical scans with medical codes determined to be truth data. Corresponding medical reports and/or other natural language text data associated with a medical scan can be utilized to train a medical scan natural language analysis function by generating a medical report natural language model. The medical scan natural language analysis function can be utilized to generate inference data for incoming medical reports for other medical scans to automatically determine corresponding medical codes, which can be mapped to corresponding medical scans. Medical codes assigned to medical scans by utilizing the medical report natural language model can be utilized by other subsystems, for example, to train other medical scan analysis functions, to be used as truth data to verify annotations provided via other subsystems, to aid in diagnosis, or otherwise be used by other subsystems as described herein.

A medical scan comparison system 116 can be utilized by one or more subsystems to identify and/or display similar medical scans, for example, to perform or determine function parameters for a medical scan similarity analysis function, to generate or retrieve similar scan data, or otherwise compare medical scan data. The medical scan comparison system 116 can also utilize some or all features of other subsystems as described herein. The medical scan comparison system 116 can be operable to receive a medical scan via a network and can generate similar scan data. The similar scan data can include a subset of medical scans from a medical scan database and can be generated by performing an abnormality similarity function, such as medical scan similarity analysis function, to determine that a set of abnormalities included in the subset of medical scans compare favorably to an abnormality identified in the medical scan. At least one cross-sectional image can be selected from each medical scan of the subset of medical scans for display on a display device associated with a user of the medical scan comparison system in conjunction with the medical scan.

Figure 2A:
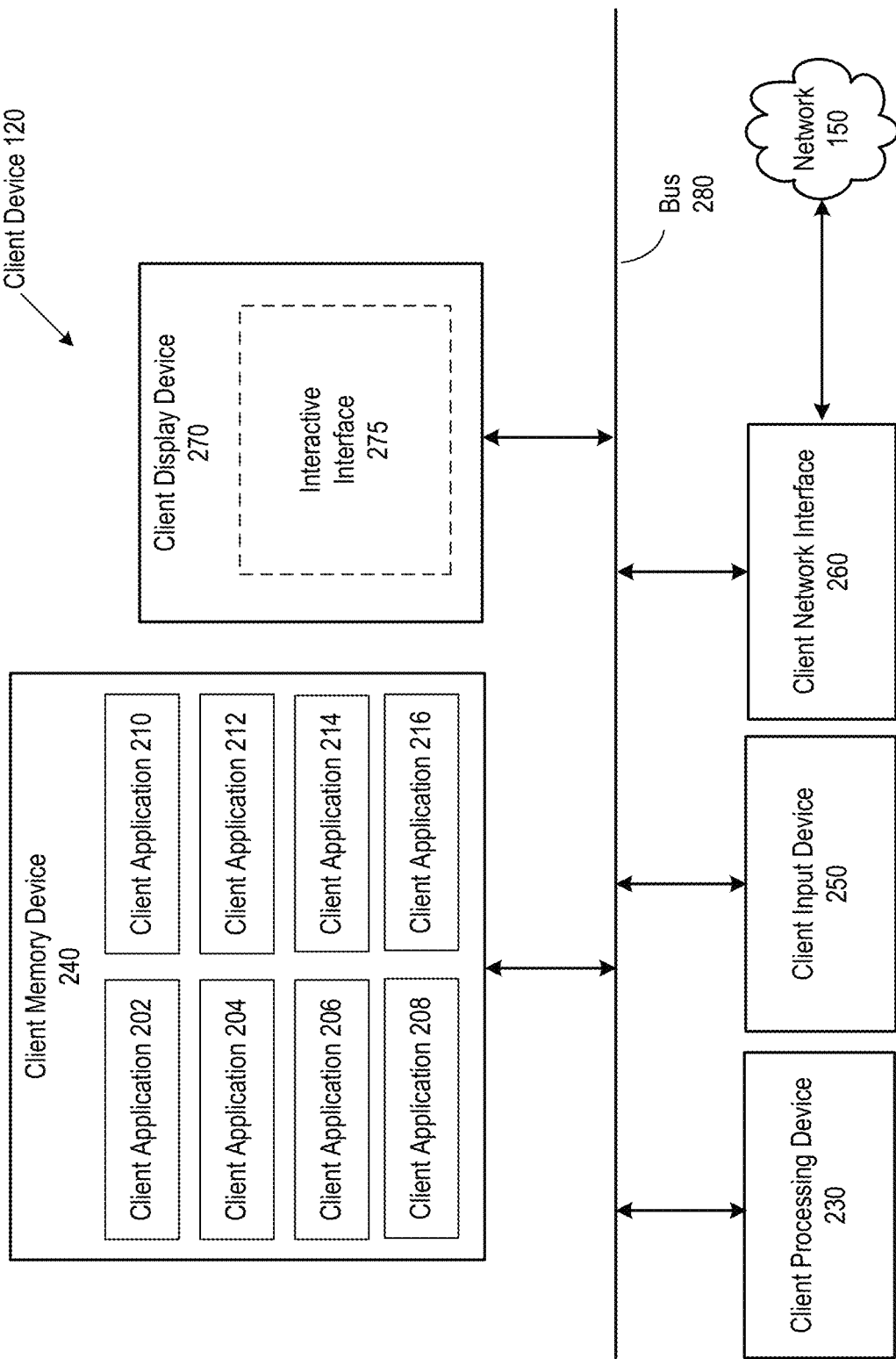
FIG. 2A is a schematic block diagram of a client device in accordance with various embodiments.

FIG. 2A presents an embodiment of client device 120. Each client device 120 can include one or more client processing devices 230, one or more client memory devices 240, one or more client input devices 250, one or more client network interfaces 260 operable to more support one or more communication links via the network 150 indirectly and/or directly, and/or one or more client display devices 270, connected via bus 280. Client applications 202, 204, 206, 208, 210, 212, 214, and/or 216 correspond to subsystems 102, 104, 106, 108, 110, 112, 114, and/or 116 of the medical scan processing system respectfully. Each client device 120 can receive the application data from the corresponding subsystem via network 150 by utilizing network interface 260, for storage in the one or more memory devices 240. In various embodiments, some or all client devices 120 can include a computing device associated with a radiologist, medical entity, or other user of one or more subsystems as described herein.

The one or more processing devices 230 can display interactive interface 275 on the one or more client display devices 270 in accordance with one or more of the client applications 202, 204, 206, 208, 210, 212, 214, and/or 216, for example, where a different interactive interface 275 is displayed for some or all of the client applications in accordance with the website presented by the corresponding subsystem 102, 104, 106, 108, 110, 112, 114 and/or 116. The user can provide input in response to menu data or other prompts presented by the interactive interface via the one or more client input devices 250, which can include a microphone, mouse, keyboard, touchscreen of display device 270 itself or other touchscreen, and/or other device allowing the user to interact with the interactive interface. The one or more processing devices 230 can process the input data and/or send raw or processed input data to the corresponding subsystem, and/or can receive and/or generate new data in response for presentation via the interactive interface 275 accordingly, by utilizing network interface 260 to communicate bidirectionally with one or more subsystems and/or databases of the medical scan processing system via network 150.

Figure 2B:
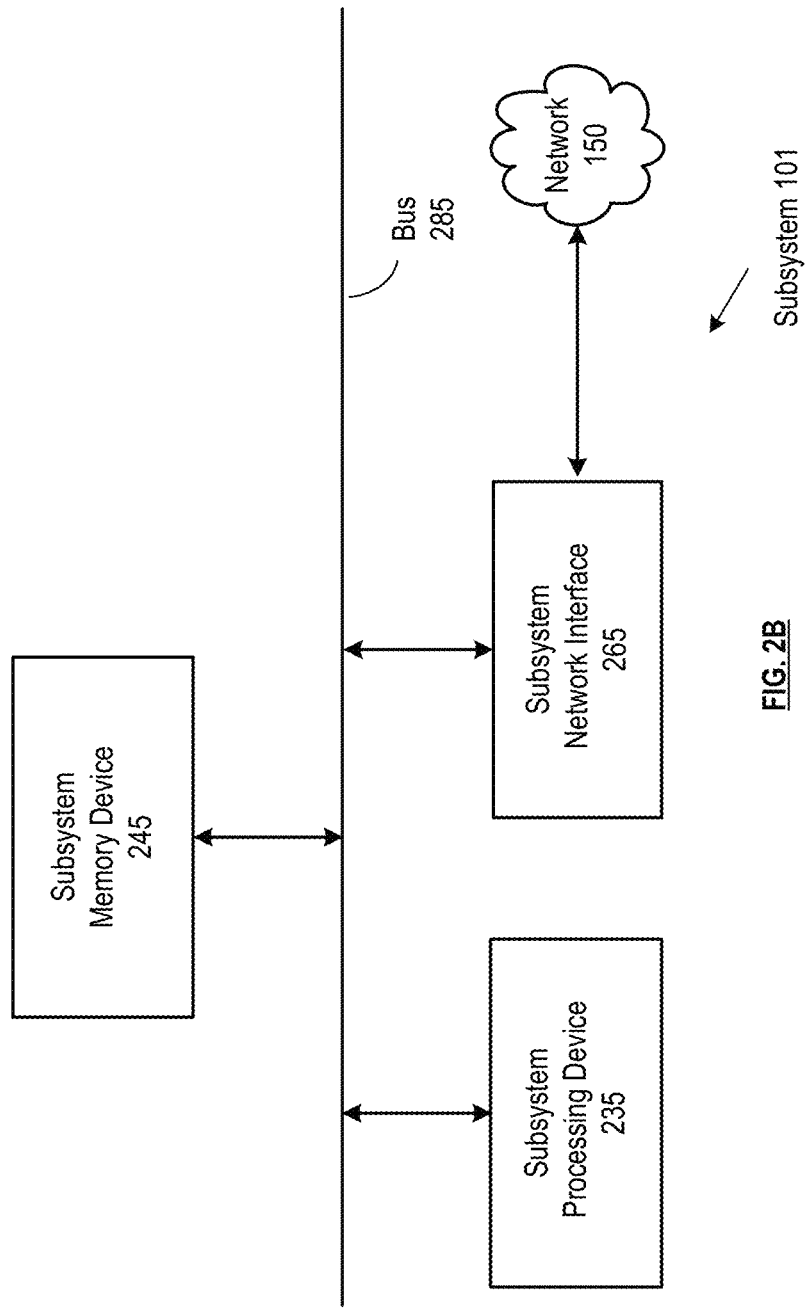
FIG. 2B is a schematic block diagram of one or more subsystems in accordance with various embodiments.

FIG. 2B presents an embodiment of a subsystem 101, which can be utilized in conjunction with subsystem 102, 104, 106, 108, 110, 112, 114 and/or 116. Each subsystem 101 can include one or more subsystem processing devices 235, one or more subsystem memory devices 245, and/or one or more subsystem network interfaces 265, connected via bus 285. The subsystem memory devices 245 can store executable instructions that, when executed by the one or more subsystem processing devices 235, facilitate performance of operations by the subsystem 101, as described for each subsystem herein.

Figure 3:
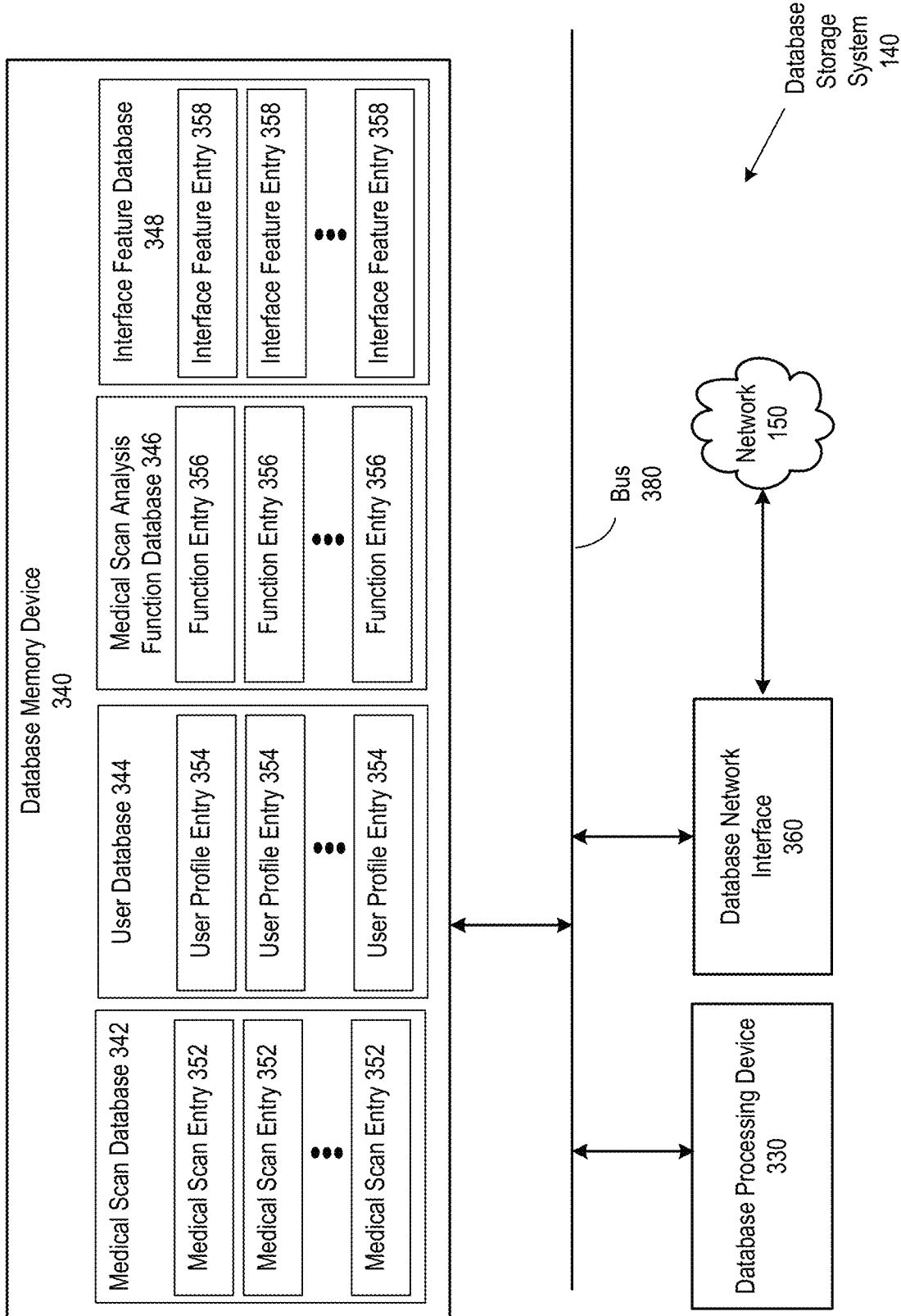
FIG. 3 is a schematic block diagram of a database storage system in accordance with various embodiments.

FIG. 3 presents an embodiment of the database storage system 140. Database storage system 140 can include at least one database processing device 330, at least one database memory device 340, and at least one database network interface 360, operable to more support one or more communication links via the network 150 indirectly and/or directly, all connected via bus 380. The database storage system 140 can store one or more databases the at least one memory 340, which can include a medical scan database 342 that includes a plurality medical scan entries 352, a user database 344 that includes a plurality of user profile entries 354, a medical scan analysis function database 346 that includes a plurality of medical scan analysis function entries 356, an interface feature database 348 can include a plurality of interface feature entries 358, and/or other databases that store data generated and/or utilized by the subsystems 101. Some or all of the databases 342, 344, 346 and/or 348 can consist of multiple databases, can be stored relationally or non-relationally, and can include different types of entries and different mappings than those described herein. A database entry can include an entry in a relational table or entry in a non-relational structure. Some or all of the data attributes of an entry 352, 354, 356, and/or 358 can refer to data included in the entry itself or that is otherwise mapped to an identifier included in the entry and can be retrieved from, added to, modified, or deleted from the database storage system 140 based on a given identifier of the entry. Some or all of the databases 342, 344, 346, and/or 348 can instead be stored locally by a corresponding subsystem, for example, if they are utilized by only one subsystem.

The processing device 330 can facilitate read/write requests received from subsystems and/or client devices via the network 150 based on read/write permissions for each database stored in the at least one memory device 340. Different subsystems can be assigned different read/write permissions for each database based on the functions of the subsystem, and different client devices 120 can be assigned different read/write permissions for each database. One or more client devices 120 can correspond to one or more administrators of one or more of the databases stored by the database storage system, and database administrator devices can manage one or more assigned databases, supervise assess and/or efficiency, edit permissions, or otherwise oversee database processes based on input to the client device via interactive interface 275.

Figure 4A:
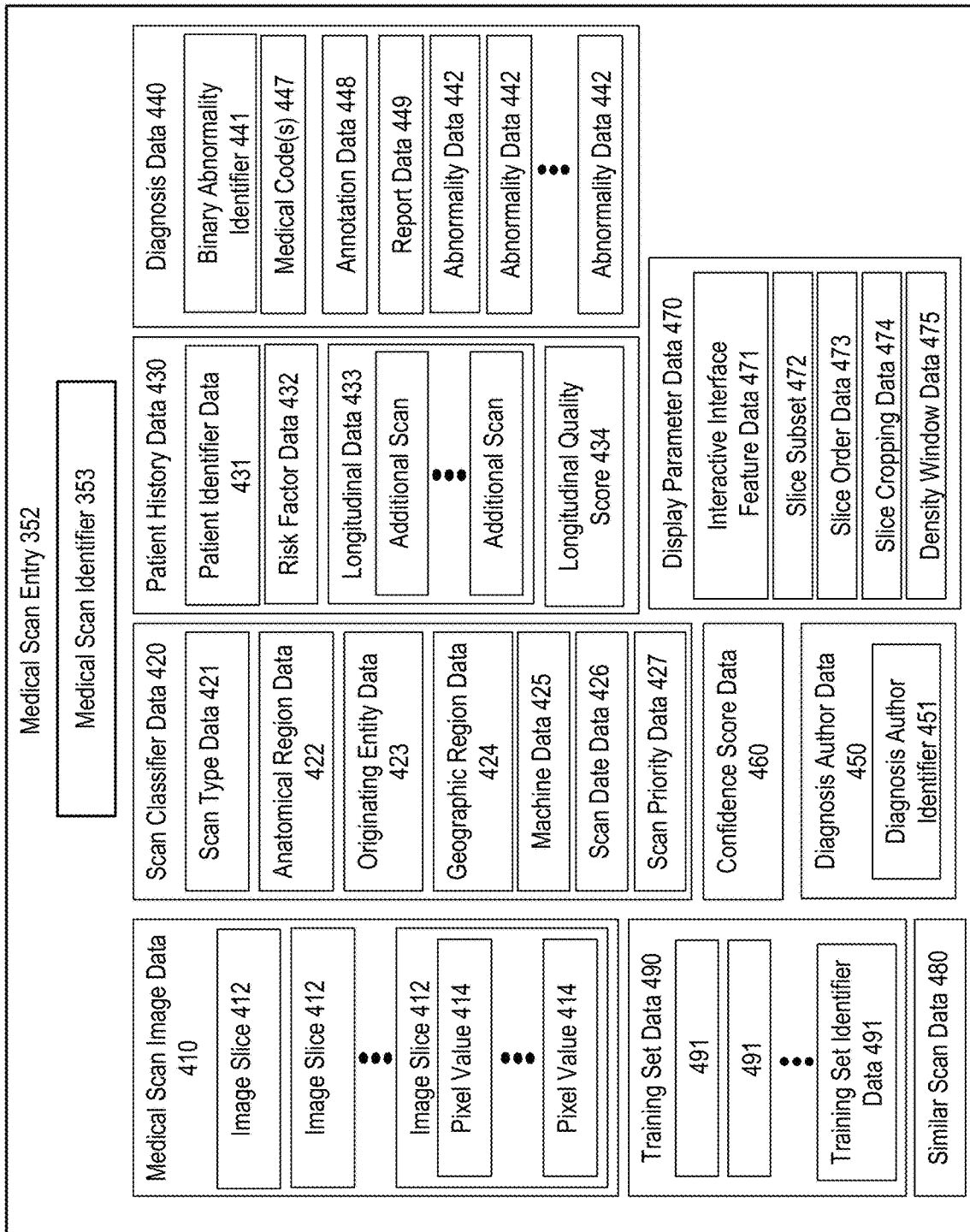
FIG. 4A is schematic block diagram of a medical scan entry in accordance with various embodiments.

FIG. 4A presents an embodiment of a medical scan entry 352, stored in medical scan database 342, included in metadata of a medical scan, and/or otherwise associated with a medical scan. A medical scan can include imaging data corresponding to a CT scan, x-ray, MRI, PET scan, Ultrasound, EEG, mammogram, or other type of radiological scan or medical scan taken of an anatomical region of a human body, animal, organism, or object and further can include metadata corresponding to the imaging data. Some or all of the medical scan entries can be formatted in accordance with a Digital Imaging and Communications in Medicine (DICOM) format or other standardized image format, and some or more of the fields of the medical scan entry 352 can be included in a DICOM header or other standardized header of the medical scan. Medical scans can be awaiting review or can have already been reviewed by one or more users or automatic processes and can include tentative diagnosis data automatically generated by a subsystem, generated based on user input, and/or generated from another source. Some medical scans can include final, known diagnosis data generated by a subsystem and/or generated based on user input, and/or generated from another source, and can included in training sets used to train processes used by one or more subsystems such as the medical scan image analysis system 112 and/or the medical scan natural language analysis system 114.

Some medical scans can include one or more abnormalities, which can be identified by a user or can be identified automatically. Abnormalities can include nodules, for example malignant nodules identified in a chest CT scan. Abnormalities can also include and/or be characterized by one or more abnormality pattern categories such as such as cardiomegaly, consolidation, effusion, emphysema, and/or fracture, for example identified in a chest x-ray. Abnormalities can also include any other unknown, malignant or benign feature of a medical scan identified as not normal. Some scans can contain zero abnormalities, and can be identified as normal scans. Some scans identified as normal scans can include identified abnormalities that are classified as benign, and include zero abnormalities classified as either unknown or malignant. Scans identified as normal scans may include abnormalities that were not detected by one or more subsystems and/or by an originating entity. Thus, some scans may be improperly identified as normal. Similarly, scans identified to include at least one abnormality may include at least one abnormality that was improperly detected as an abnormality by one or more subsystems and/or by an originating entity. Thus, some scans may be improperly identified as containing abnormalities.

Each medical scan entry 352 can be identified by its own medical scan identifier 353, and can include or otherwise map to medical scan image data 410, and metadata such as scan classifier data 420, patient history data 430, diagnosis data 440, annotation author data 450, confidence score data 460, display parameter data 470, similar scan data 480, training set data 490, and/or other data relating to the medical scan. Some or all of the data included in a medical scan entry 352 can be used to aid a user in generating or editing diagnosis data 440, for example, in conjunction with the medical scan assisted review system 102, the medical scan report labeling system 104, and/or the medical scan annotator system 106. Some or all of the data included in a medical scan entry 352 can be used to allow one or more subsystems 101, such as automated portions of the medical scan report labeling system 104 and/or the medical scan diagnosing system 108, to automatically generate and/or edit diagnosis data 440 or other data the medical scan. Some or all of the data included in a medical scan entry 352 can be used to train some or all medical scan analysis functions of the medical scan analysis function database 346 such as one or more medical scan image analysis functions, one or more medical scan natural language analysis functions, one or more medical scan similarity analysis functions, one or more medical report generator functions, and/or one or more medical report analysis functions, for example, in conjunction with the medical scan image analysis system 112, the medical scan natural language analysis system 114, and/or the medical scan comparison system 116.

The medical scan entries 352 and the associated data as described herein can also refer to data associated with a medical scan that is not stored by the medical scan database, for example, that is uploaded by a client device for direct transmission to a subsystem, data generated by a subsystem and used as input to another subsystem or transmitted directly to a client device, data stored by a Picture Archive and Communication System (PACS) communicating with the medical scan processing system 100, or other data associated with a medical scan that is received and or generated without being stored in the medical scan database 342. For example, some or all of the structure and data attributes described with respect to a medical scan entry 352 can also correspond to structure and/or data attribute of data objects or other data generated by and/or transmitted between subsystems and/or client devices that correspond to a medical scan. Herein, any of the data attributes described with respect to a medical scan entry 352 can also correspond to data extracted from a data object generated by a subsystem or client device or data otherwise received from a subsystem, client device, or other source via network 150 that corresponds to a medical scan.

The medical scan image data 410 can include one or more images corresponding to a medical scan. The medical scan image data 410 can include one or more image slices 412, for example, corresponding to a single x-ray image, a plurality of cross-sectional, tomographic images of a scan such as a CT scan, or any plurality of images taken from the same or different point at the same or different angles. The medical scan image data 410 can also indicate an ordering of the one or more image slices 412. Herein, a "medical scan" can refer a full scan of any type represented by medical scan image data 410. Herein, an "image slice" can refer to one of a plurality of cross-sectional images of the medical scan image data 410, one of a plurality of images taken from different angles of the medical scan image data 410, and/or the single image of the medical scan image data 410 that includes only one image. Furthermore "plurality of image slices" can refer to all of the images of the associated medical scan, and refers to only a single image if the medical scan image data 410 includes only one image. Each image slice 412 can include a plurality of pixel values 414 mapped to each pixel of the image slice. Each pixel value can correspond to a density value, such as a Hounsfield value or other measure of density. Pixel values can also correspond to a grayscale value, a RGB (Red-Green-Blue) or other color value, or other data stored by each pixel of an image slice 412.

Scan classifier data 420 can indicate classifying data of the medical scan. Scan classifier data can include scan type data 421, for example, indicating the modality of the scan. The scan classifier data can indicate that the scan is a CT scan, x-ray, MRI, PET scan, Ultrasound, EEG, mammogram, or other type of scan. Scan classifier data 420 can also include anatomical region data 422, indicating for example, the scan is a scan of the chest, head, right knee, or other anatomical region. Scan classifier data can also include originating entity data 423, indicating the hospital where the scan was taken and/or a user that uploaded the scan to the system. If the originating entity data corresponds to a user of one or more subsystems 101, the originating entity data can include a corresponding user profile identifier and/or include other data from the user profile entry 354 of the user. Scan classifier data 420 can include geographic region data 424, indicating a city, state, and/or country from which the scan originated, for example, based on the user data retrieved from the user database 344 based on the originating entity. Scan classifier data can also include machine data 425, which can include machine identifier data, machine model data, machine calibration data, and/or contrast agent data, for example based on imaging machine data retrieved from the user database 344 based on the originating entity data 423. The scan classifier data 420 can include scan date data 426 indicating when the scan was taken. The scan classifier data 420 can include scan priority data 427, which can indicate a priority score, ranking, number in a queue, or other priority data with regard to triaging and/or review. A priority score, ranking, or queue number of the scan priority data 427 can be generated by automatically by a subsystem based on the scan priority data 427, based on a severity of patient symptoms or other indicators in the risk factor data 432, based on a priority corresponding to the originating entity, based on previously generated diagnosis data 440 for the scan, and/or can be assigned by the originating entity and/or a user of the system.

The scan classifier data 420 can include other classifying data not pictured in FIG. 4A. For example, a set of scans can include medical scan image data 410 corresponding to different imaging planes. The scan classifier data can further include imaging plane data indicating one or more imaging planes corresponding to the image data. For example, the imaging plane data can indicate the scan corresponds to the axial plane, sagittal plane, or coronal plane. A single medical scan entry 352 can include medical scan image data 410 corresponding multiple planes, and each of these planes can be tagged appropriately in the image data. In other embodiments, medical scan image data 410 corresponding to each plane can be stored as separate medical scan entries 352, for example, with a common identifier indicating these entries belong to the same set of scans.

Alternatively or in addition, the scan classifier data 420 can include sequencing data. For example, a set of scans can include medical scan image data 410 corresponding to different sequences. The scan classifier data can further include sequencing data indicating one or more of a plurality of sequences of the image data corresponds to, for example, indicating whether an MRI scan corresponds to a T2 sequence, a T1 sequence, a T1 sequence with contrast, a diffusion sequence, a FLAIR sequence, or other MRI sequence. A single medical scan entry 352 can include medical scan image data 410 corresponding to multiple sequences, and each of these sequences can be tagged appropriately in the entry. In other embodiments, medical scan image data 410 corresponding to each sequence can be stored as separate medical scan entries 352, for example, with a common identifier indicating these entries belong to the same set of scans.

Alternatively or in addition, the scan classifier data 420 can include an image quality score. This score can be determined automatically by one or more subsystems 101, and/or can be manually assigned the medical scan. The image quality score can be based on a resolution of the image data 410, where higher resolution image data is assigned a more favorable image quality score than lower resolution image data. The image quality score can be based on whether the image data 410 corresponds to digitized image data received directly from the corresponding imaging machine, or corresponds to a hard copy of the image data that was later scanned in. In some embodiments, the image quality score can be based on a detected corruption, and/or detected external factor that determined to negatively affect the quality of the image data during the capturing of the medical scan and/or subsequent to the capturing of the medical scan. In some embodiments, the image quality score can be based on detected noise in the image data, where a medical scan with a higher level of detected noise can receive a less favorable image quality score than a medical scan with a lower level of detected noise. Medical scans with this determined corruption or external factor can receive a less favorable image quality score than medical scans with no detected corruption or external factor.

In some embodiments, the image quality score can be based on include machine data 425. In some embodiments, one or more subsystems can utilize the image quality score to flag medical scans with image quality scores that fall below an image quality threshold. The image quality threshold can be the same or different for different subsystems, medical scan modalities, and/or anatomical regions. For example, the medical scan image analysis system can automatically filter training sets based on selecting only medical scans with image quality scores that compare favorably to the image quality threshold. As another example, one or more subsystems can flag a particular imaging machine and/or hospital or other medical entity that have produced at least a threshold number and/or percentage of medical scan with image quality scores that compare unfavorably to the image quality threshold. As another example, a de-noising algorithm can be automatically utilized to clean the image data when the image quality score compares unfavorably to the image quality threshold. As another example, the medical scan image analysis system can select a particular medical image analysis function from a set of medical image analysis functions to utilize on a medical scan to generate inference data for the medical scan. Each of this set of medical image analysis function can be trained on different levels of image quality, and the selected image analysis function can be selected based on the determined image quality score falling within a range of image quality scores the image analysis function was trained on and/or is otherwise suitable for.

The patient history data 430 can include patient identifier data 431 which can include basic patient information such as name or an identifier that may be anonymized to protect the confidentiality of the patient, age, and/or gender. The patient identifier data 431 can also map to a patient entry in a separate patient database stored by the database storage system, or stored elsewhere. The patient history data can include patient risk factor data 432 which can include previous medical history, family medical history, smoking and/or drug habits, pack years corresponding to tobacco use, environmental exposures, patient symptoms, etc. The patient history data 430 can also include longitudinal data 433, which can identify one or more additional medical scans corresponding to the patient, for example, retrieved based on patient identifier data 431 or otherwise mapped to the patient identifier data 431. Some or all additional medical scans can be included in the medical scan database, and can be identified based on their corresponding identifiers medical scan identifiers 353. Some or all additional medical scans can be received from a different source and can otherwise be identified. Alternatively or in addition, the longitudinal data can simply include some or all relevant scan entry data of a medical scan entry 352 corresponding to the one or more additional medical scans. The additional medical scans can be the same type of scan or different types of scans. Some or all of the additional scans may correspond to past medical scans, and/or some or all of the additional scans may correspond to future medical scans. The longitudinal data 433 can also include data received and/or determined at a date after the scan such as final biopsy data, or some or all of the diagnosis data 440. The patient history data can also include a longitudinal quality score 434, which can be calculated automatically by a subsystem, for example, based on the number of additional medical scans, based on how many of the additional scans in the file were taken before and/or after the scan based on the scan date data 426 of the medical scan and the additional medical scans, based on a date range corresponding to the earliest scan and corresponding to the latest scan, based on the scan types data 421 these scans, and/or based on whether or not a biopsy or other final data is included. As used herein, a "high" longitudinal quality score refers to a scan having more favorable longitudinal data than that with a "low" longitudinal quality score.

Diagnosis data 440 can include data that indicates an automated diagnosis, a tentative diagnosis, and/or data that can otherwise be used to support medical diagnosis, triage, medical evaluation and/or other review by a medical professional or other user. The diagnosis data 440 of a medical scan can include a binary abnormality identifier 441 indicating whether the scan is normal or includes at least one abnormality. In some embodiments, the binary abnormality identifier 441 can be determined by comparing some or all of confidence score data 460 to a threshold, can be determined by comparing a probability value to a threshold, and/or can be determined by comparing another continuous or discrete value indicating a calculated likelihood that the scan contains one or more abnormalities to a threshold. In some embodiments, non-binary values, such as one or more continuous or discrete values indicating a likelihood that the scan contains one or more abnormalities, can be included in diagnosis data 440 in addition to, or instead of, binary abnormality identifier 441. One or abnormalities can be identified by the diagnosis data 440, and each identified abnormality can include its own set of abnormality annotation data 442. Alternatively, some or all of the diagnosis data 440 can indicate and/or describe multiple abnormalities, and thus will not be presented for each abnormality in the abnormality annotation data 442. For example, the report data 449 of the diagnosis data 440 can describe all identified abnormalities, and thus a single report can be included in the diagnosis.

Figure 4B:
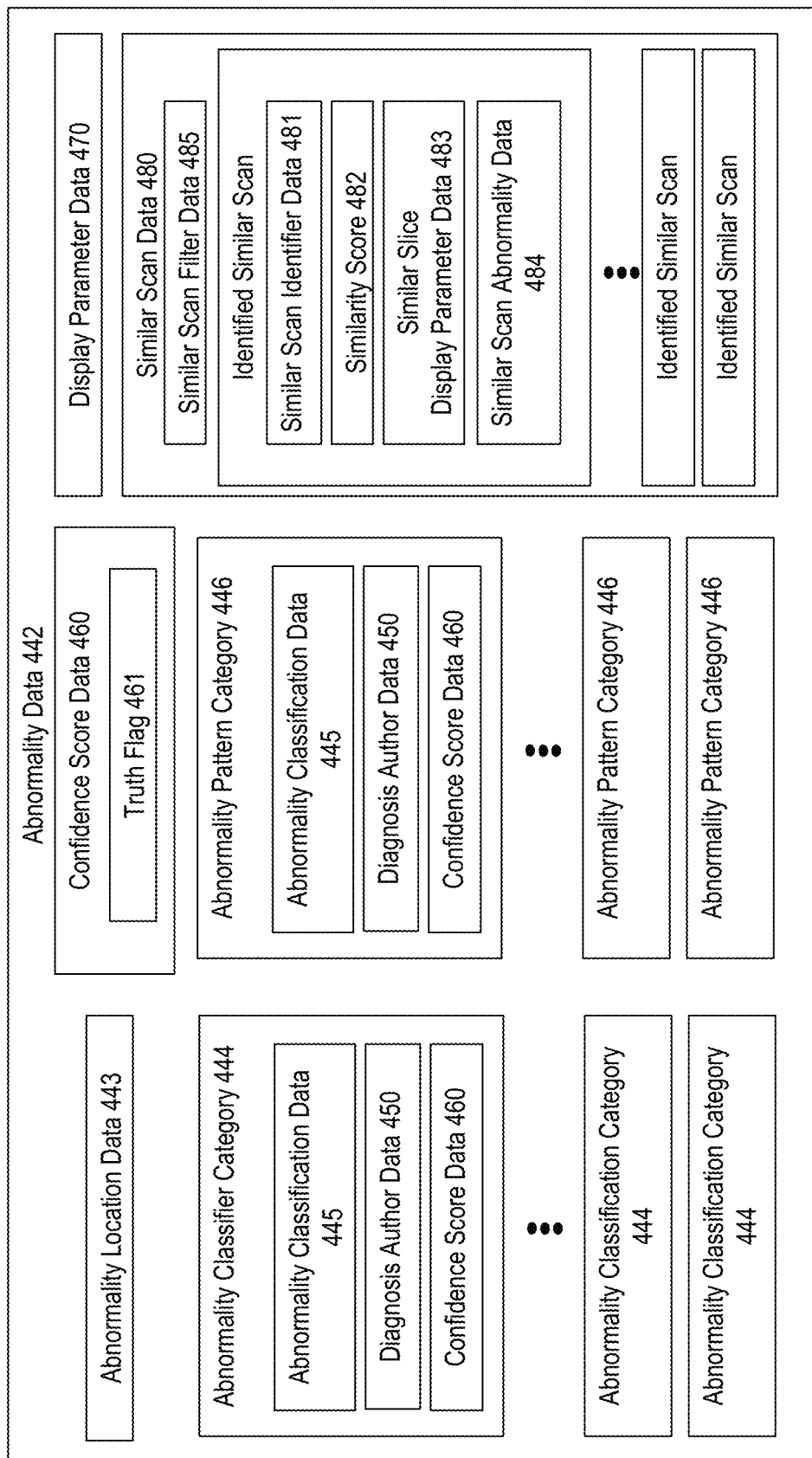
FIG. 4B is a schematic block diagram of abnormality data in accordance with various embodiments.

FIG. 4B presents an embodiment of the abnormality annotation data 442. The abnormality annotation data 442 for each abnormality can include abnormality location data 443, which can include an anatomical location and/or a location specific to pixels, image slices, coordinates or other location information identifying regions of the medical scan itself. The abnormality annotation data 442 can include abnormality classification data 445 which can include binary, quantitative, and/or descriptive data of the abnormality as a whole, or can correspond to one or more abnormality classifier categories 444, which can include size, volume, pre-post contrast, doubling time, calcification, components, smoothness, spiculation, lobulation, sphericity, internal structure, texture, or other categories that can classify and/or otherwise characterize an abnormality. Abnormality classifier categories 444 can be assigned a binary value, indicating whether or not such a category is present. For example, this binary value can be determined by comparing some or all of confidence score data 460 to a threshold, can be determined by comparing a probability value to a threshold, and/or can be determined by comparing another continuous or discrete value indicating a calculated likelihood that a corresponding abnormality classifier category 444 is present to a threshold, which can be the same or different threshold for each abnormality classifier category 444. In some embodiments, abnormality classifier categories 444 can be assigned one or more non-binary values, such as one or more continuous or discrete values indicating a likelihood that the corresponding classifier category 444 is present.

The abnormality classifier categories 444 can also include a malignancy category, and the abnormality classification data 445 can include a malignancy rating such as a Lung-RADS score, a Fleischner score, and/or one or more calculated values that indicate malignancy level, malignancy severity, and/or probability of malignancy. Alternatively or in addition, the malignancy category can be assigned a value of "yes", "no", or "maybe". The abnormality classifier categories 444 can also include abnormality pattern categories 446 such as cardiomegaly, consolidation, effusion, emphysema, and/or fracture, and the abnormality classification data 445 for each abnormality pattern category 446 can indicate whether or not each of the abnormality patterns is present.

The abnormality classifier categories can correspond to Response Evaluation Criteria in Solid Tumors (RECIST) eligibility and/or RECIST evaluation categories. For example, an abnormality classifier category 444 corresponding to RECIST eligibility can have corresponding abnormality classification data 445 indicating a binary value "yes" or "no", and/or can indicate if the abnormality is a "target lesion" and/or a "non-target lesion." As another example, an abnormality classifier category 444 corresponding to a RECIST evaluation category can be determined based on longitudinal data 433 and can have corresponding abnormality classification data 445 that includes one of the set of possible values "Complete Response", "Partial Response", "Stable Disease", or "Progressive Disease."

The diagnosis data 440 as a whole, and/or the abnormality annotation data 442 for each abnormality, can include custom codes or datatypes identifying the binary abnormality identifier 441, abnormality location data 443 and/or some or all of the abnormality classification data 445 of one or more abnormality classifier categories 444. Alternatively or in addition, some or all of the abnormality annotation data 442 for each abnormality and/or other diagnosis data 440 can be presented in a DICOM format or other standardized image annotation format, and/or can be extracted into custom datatypes based on abnormality annotation data originally presented in DICOM format. Alternatively or in addition, the diagnosis data 440 and/or the abnormality annotation data 442 for each abnormality can be presented as one or more medical codes 447 such as SNOMED codes, Current Procedure Technology (CPT) codes, ICD-9 codes, ICD-10 codes, or other standardized medical codes used to label or otherwise describe medical scans.

Alternatively or in addition, the diagnosis data 440 can include natural language text data 448 annotating or otherwise describing the medical scan as a whole, and/or the abnormality annotation data 442 can include natural language text data 448 annotating or otherwise describing each corresponding abnormality. In some embodiments, some or all of the diagnosis data 440 is presented only as natural language text data 448. In some embodiments, some or all of the diagnosis data 440 is automatically generated by one or more subsystems based on the natural language text data 448, for example, without utilizing the medical scan image data 410, for example, by utilizing one or more medical scan natural language analysis functions trained by the medical scan natural language analysis system 114. Alternatively or in addition, some embodiments, some or all of the natural language text data 448 is generated automatically based on other diagnosis data 440 such as abnormality annotation data 442, for example, by utilizing a medical scan natural language generating function trained by the medical scan natural language analysis system 114.

The diagnosis data can include report data 449 that includes at least one medical report, which can be formatted to include some or all of the medical codes 447, some or all of the natural language text data 448, other diagnosis data 440, full or cropped images slices formatted based on the display parameter data 470 and/or links thereto, full or cropped images slices or other data based on similar scans of the similar scan data 480 and/or links thereto, full or cropped images or other data based on patient history data 430 such as longitudinal data 433 and/or links thereto, and/or other data or links to data describing the medical scan and associated abnormalities. The diagnosis data 440 can also include finalized diagnosis data corresponding to future scans and/or future diagnosis for the patient, for example, biopsy data or other longitudinal data 433 determined subsequently after the scan. The medical report of report data 449 can be formatted based on specified formatting parameters such as font, text size, header data, bulleting or numbering type, margins, file type, preferences for including one or more full or cropped image slices 412, preferences for including similar medical scans, preferences for including additional medical scans, or other formatting to list natural language text data and/or image data, for example, based on preferences of a user indicated in the originating entity data 423 or other responsible user in the corresponding report formatting data.

Annotation author data 450 can be mapped to the diagnosis data for each abnormality, and/or mapped to the scan as a whole. This can include one or more annotation author identifiers 451, which can include one or more user profile identifiers of a user of the system, such as an individual medical professional, medical facility and/or medical entity that uses the system. Annotation author data 450 can be used to determine the usage data of a user profile entry 354. Annotation author data 450 can also include one or more medical scan analysis function identifiers 357 or other function identifier indicating one or more functions or other processes of a subsystem responsible for automatically generating and/or assisting a user in generating some or all of the diagnosis data, for example an identifier of a particular type and/or version of a medical scan image analysis functions that was used by the medical scan diagnosing system 108 used to generate part or all of the diagnosis data 440 and/or an interface feature identifier, indicating an one or more interface features presented to a user to facilitate entry of and/or reviewing of the diagnosis data 440. The annotation author data can also simply indicate, for one or more portions of the diagnosis data 440, if this portion was generated by a human or automatically generated by a subsystem of the medical scan processing system.

In some embodiments, if a medical scan was reviewed by multiple entities, multiple, separate diagnosis data entries 440 can be included in the medical scan entry 352, mapped to each diagnosis author in the annotation author data 450. This allows different versions of diagnosis data 440 received from multiple entities. For example, annotation author data of a particular medical scan could indicate that the annotation data was written by a doctor at medical entity A, and the medical code data was generated by user Y by utilizing the medical scan report labeling system 104, which was confirmed by expert user X. The annotation author data of another medical scan could indicate that the medical code was generated automatically by utilizing version 7 of the medical scan image analysis function relating to chest x-rays, and confirmed by expert user X. The annotation author data of another medical scan could indicate that the location and a first malignancy rating were generated automatically by utilizing version 7 of the medical scan image analysis function relating to chest x-rays, and that a second malignancy rating was entered by user Z. In some embodiments, one of the multiple diagnosis entries can include consensus annotation data, for example, generated automatically by a subsystem such as the medical scan annotating system 106 based on the multiple diagnosis data 440, based on confidence score data 460 of each of the multiple diagnosis data 440, and/or based on performance score data of a corresponding user, a medical scan analysis function, or an interface feature, identified in the annotation author data for each corresponding one of the multiple diagnosis data 440.

Confidence score data 460 can be mapped to some or all of the diagnosis data 440 for each abnormality, and/or for the scan as a whole. This can include an overall confidence score for the diagnosis, a confidence score for the binary indicator of whether or not the scan was normal, a confidence score for the location a detected abnormality, and/or confidence scores for some or all of the abnormality classifier data. This may be generated automatically by a subsystem, for example, based on the annotation author data and corresponding performance score of one or more identified users and/or subsystem attributes such as interactive interface types or medical scan image analysis functions indicated by the annotation author data. In the case where multiple diagnosis data entries 440 are included from different sources, confidence score data 460 can be computed for each entry and/or an overall confidence score, for example, corresponding to consensus diagnosis data, can be based on calculated distance or other error and/or discrepancies between the entries, and/or can be weighted on the confidence score data 460 of each entry. In various embodiments, the confidence score data 460 can include a truth flag 461 indicating the diagnosis data is considered as "known" or "truth", for example, flagged based on user input, flagged automatically based on the author data, and/or flagged automatically based on the calculated confidence score of the confidence score data exceeding a truth threshold. As used herein, a "high" confidence score refers to a greater degree or more favorable level of confidence than a "low" confidence score.

Display parameter data 470 can indicate parameters indicating an optimal or preferred display of the medical scan by an interactive interface 275 and/or formatted report for each abnormality and/or for the scan as a whole. Some or all of the display parameter data can have separate entries for each abnormality, for example, generated automatically by a subsystem 101 based on the abnormality annotation data 442. Display parameter data 470 can include interactive interface feature data 471, which can indicate one or more selected interface features associated with the display of abnormalities and/or display of the medical scan as a whole, and/or selected interface features associated with user interaction with a medical scan, for example, based on categorized interface feature performance score data and a category associated with the abnormality and/or with the medical scan itself. The display parameter data can include a slice subset 472, which can indicate a selected subset of the plurality of image slices that includes a single image slice 412 or multiple image slices 412 of the medical scan image data 410 for display by a user interface. The display parameter data 470 can include slice order data 473 that indicates a selected custom ordering and/or ranking for the slice subset 472, or for all of the slices 412 of the medical scan. The display parameter data 470 can include slice cropping data 474 corresponding to some or all of the slice subset 472, or all of the image slices 412 of the medical scan, and can indicating a selected custom cropped region of each image slice 412 for display, or the same selected custom cropped region for the slice subset 472 or for all slices 412. The display parameter data can include density window data 475, which can indicate a selected custom density window for display of the medical scan as a whole, a selected custom density window for the slices subset 472, and/or selected custom density windows for each of the image slices 412 of the slice subset 472, and/or for each image slice 412 of the medical scan. The density window data 475 can indicate a selected upper density value cut off and a selected lower density value cut off, and/or can include a selected deterministic function to map each density value of a pixel to a grayscale value based on the preferred density window. The interactive interface feature data 471, slice subset 472, slice order data 473, slice cropping data 474, and/or the density window data 475 can be selected via user input and/or generated automatically by one or more subsystems 101, for example, based on the abnormality annotation data 442 and/or based on performance score data of different interactive interface versions.

Similar scan data 480 can be mapped to each abnormality, or the scan as a whole, and can include similar scan identifier data 481 corresponding to one or more identified similar medical scans, for example, automatically identified by a subsystem 101, for example, by applying a similar scan identification step of the medical scan image analysis system 112 and/or applying medical scan similarity analysis function to some or all of the data stored in the medical scan entry of the medical scan, and/or to some or all corresponding data of other medical scans in the medical scan database. The similar scan data 480 can also correspond to medical scans received from another source. The stored similarity data can be used to present similar cases to users of the system and/or can be used to train medical scan image analysis functions or medical scan similarity analysis functions.

Each identified similar medical scan can have its own medical scan entry 352 in the medical scan database 342 with its own data, and the similar scan identifier data 481 can include the medical scan identifier 353 each similar medical scan. Each identified similar medical scan can be a scan of the same scan type or different scan type than medical scan.

The similar scan data 480 can include a similarity score 482 for each identified similar scan, for example, generated based on some or all of the data of the medical scan entry 352 for medical scan and based on some or all of the corresponding data of the medical scan entry 352 for the identified similar medical scan. For example, the similarity score 482 can be generated based on applying a medical scan similarity analysis function to the medical image scan data of medical scans and 402, to some or all of the abnormality annotation data of medical scans and 402, and/or to some or all of the patient history data 430 of medical scans and 402 such as risk factor data 432. As used herein, a "high" similarity score refers a higher level of similarity that a "low" similarity score.

The similar scan data 480 can include its own similar scan display parameter data 483, which can be determined based on some or all of the display parameter data 470 of the identified similar medical scan. Some or all of the similar scan display parameter data 483 can be generated automatically by a subsystem, for example, based on the display parameter data 470 of the identified similar medical scan, based on the abnormality annotation data 442 of the medical scan itself and/or based on display parameter data 470 of the medical scan itself. Thus, the similar scan display parameter data 483 can be the same or different than the display parameter data 470 mapped to the identified similar medical scan and/or can be the same or different than the display parameter data 470 of the medical scan itself. This can be utilized when displaying similar scans to a user via interactive interface 275 and/or can be utilized when generating report data 449 that includes similar scans, for example, in conjunction with the medical scan assisted review system 102.

The similar scan data 480 can include similar scan abnormality data 484, which can indicate one of a plurality of abnormalities of the identified similar medical scan and its corresponding abnormality annotation data 442. For example, the similarity scan abnormality data 484 can include an abnormality pair that indicates one of a plurality of abnormalities of the medical scan, and indicates one of a plurality of abnormalities of the identified similar medical scan, for example, that was identified as the similar abnormality.

The similar scan data 480 can include similar scan filter data 485. The similar scan filter data can be generated automatically by a subsystem, and can include a selected ordered or un-ordered subset of all identified similar scans of the similar scan data 480, and/or a ranking of all identified similar scans. For example, the subset can be selected and/or some or all identified similar scans can be ranked based on each similarity score 482, and/or based on other factors such as based on a longitudinal quality score 434 of each identified similar medical scan.

The training set data 490 can indicate one or more training sets that the medical scan belongs to. For example, the training set data can indicate one or more training set identifiers 491 indicating one or more medical scan analysis functions that utilized the medical scan in their training set, and/or indicating a particular version identifier 641 of the one or more medical scan analysis functions that utilized the medical scan in their training set. The training set data 490 can also indicate which portions of the medical scan entry were utilized by the training set, for example, based on model parameter data 623 of the corresponding medical scan analysis functions. For example, the training set data 490 can indicate that the medical scan image data 410 was included in the training set utilized to train version X of the chest x-ray medical scan image analysis function, or that the natural language text data 448 of this medical scan was used to train version Y of the natural language analysis function.

Figure 5A:
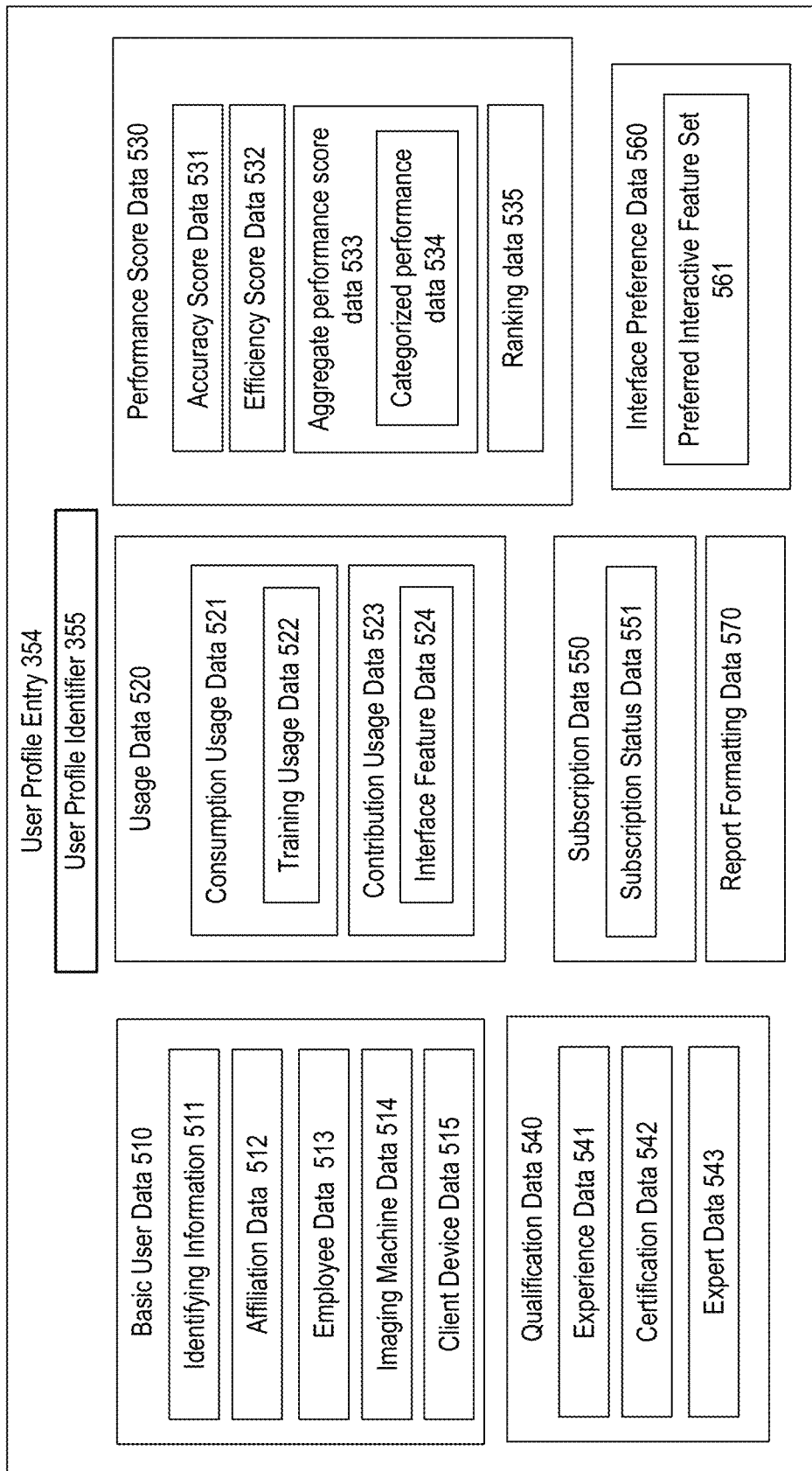
FIG. 5A is a schematic block diagram of a user profile entry in accordance with various embodiments.

FIG. 5A presents an embodiment of a user profile entry 354, stored in user database 344 or otherwise associated with a user. A user can correspond to a user of one or more of the subsystems such as a radiologist, doctor, medical professional, medical report labeler, administrator of one or more subsystems or databases, or other user that uses one or more subsystems 101. A user can also correspond to a medical entity such as a hospital, medical clinic, establishment that utilizes medical scans, establishment that employs one or more of the medical professionals described, an establishment associated with administering one or more subsystems, or other entity. A user can also correspond to a particular client device 120 or account that can be accessed one or more medical professionals or other employees at the same or different medical entities. Each user profile entry can have a corresponding user profile identifier 355.

A user profile entry 354 can include basic user data 510, which can include identifying information 511 corresponding to the user such as a name, contact information, account/login/password information, geographic location information such as geographic region data 424, and/or other basic information. Basic user data 510 can include affiliation data 512, which can list one or more medical entities or other establishments the user is affiliated with, for example, if the user corresponds to a single person such as a medical professional, or if the user corresponds to a hospital in a network of hospitals. The affiliation data 512 can include one or more corresponding user profile identifiers 355 and/or basic user data 510 if the corresponding affiliated medical entity or other establishment has its own entry in the user database. The user identifier data can include employee data 513 listing one or more employees, such as medical professionals with their own user profile entries 354, for example, if the user corresponds to a medical entity or supervising medical professional of other medical professional employees, and can list a user profile identifier 355 and/or basic user data 510 for each employee. The basic user data 510 can also include imaging machine data 514, which can include a list of machines affiliated with the user which can include machine identifiers, model information, calibration information, scan type information, or other data corresponding to each machine, for example, corresponding to the machine data 425. The user profile entry can include client device data 515, which can include identifiers for one or more client devices associated with the user, for example, allowing subsystems 101 to send data to a client device 120 corresponding to a selected user based on the client device data and/or to determine a user that data was received by determining the client device from which the data was received.

The user profile entry can include usage data 520 which can include identifying information for a plurality of usages by the user in conjunction with using one or more subsystems 101. This can include consumption usage data 521, which can include a listing of, or aggregate data associated with, usages of one or more subsystems by the user, for example, where the user is utilizing the subsystem as a service. For example, the consumption usage data 521 can correspond to each instance where diagnosis data was sent to the user for medical scans provided to the user in conjunction with the medical scan diagnosing system 108 and/or the medical scan assisted review system 102. Some or all of consumption usage data 521 can include training usage data 522, corresponding to usage in conjunction with a certification program or other user training provided by one or more subsystems. The training usage data 522 can correspond to each instance where diagnosis feedback data was provided by user for a medical scan with known diagnosis data, but diagnosis feedback data is not utilized by a subsystem to generate, edit, and/or confirm diagnosis data 440 of the medical scan, as it is instead utilized to train a user and/or determine performance data for a user.

Usage data 520 can include contribution usage data 523, which can include a listing of, or aggregate data associated with, usages of one or more subsystems 101 by the user, for example, where the user is generating and/or otherwise providing data and/or feedback that can is utilized by the subsystems, for example, to generate, edit, and/or confirm diagnosis data 440 and/or to otherwise populate, modify, or confirm portions of the medical scan database or other subsystem data. For example, the contribution usage data 523 can correspond to diagnosis feedback data received from user, used to generate, edit, and/or confirm diagnosis data. The contribution usage data 523 can include interactive interface feature data 524 corresponding to the interactive interface features utilized with respect to the contribution.

The consumption usage data 521 and/or the contribution usage data 523 can include medical scan entry 352 whose entries the user utilized and/or contributed to, can indicate one or more specific attributes of a medical scan entry 352 that a user utilized and/or contributed to, and/or a log of the user input generated by a client device of the user in conjunction with the data usage. The contribution usage data 523 can include the diagnosis data that the user may have generated and/or reviewed, for example, indicated by, mapped to, and/or used to generate the annotation author data 450 of corresponding medical scan entries 352. Some usages may correspond to both consumption usage of the consumption usage data 521 and contribution usage of the contribution usage data 523. The usage data 520 can also indicate one or more subsystems 101 that correspond to each consumption and/or contribution.

The user profile entry can include performance score data 530. This can include one or more performance scores generated based on the contribution usage data 523 and/or training usage data 522. The performance scores can include separate performance scores generated for every contribution in the contribution usage data 523 and/or training usage data 522 and/or generated for every training consumption usages corresponding to a training program. As used herein, a "high" performance score refers to a more favorable performance or rating than a "low" performance score.

The performance score data can include accuracy score data 531, which can be generated automatically by a subsystem for each contribution, for example, based on comparing diagnosis data received from a user to data to known truth data such as medical scans with a truth flag 461, for example, retrieved from the corresponding medical scan entry 352 and/or based on other data corresponding to the medical scan, for example, received from an expert user that later reviewed the contribution usage data of the user and/or generated automatically by a subsystem. The accuracy score data 531 can include an aggregate accuracy score generated automatically by a subsystem, for example, based on the accuracy data of multiple contributions by the user over time.

The performance data can also include efficiency score data 532 generated automatically by a subsystem for each contribution based on an amount of time taken to complete a contribution, for example, from a time the request for a contribution was sent to the client device to a time that the contribution was received from the client device, based on timing data received from the client device itself, and/or based on other factors. The efficiency score can include an aggregate efficiency score, which can be generated automatically by a subsystem based on the individual efficiency scores over time and/or based on determining a contribution completion rate, for example based on determining how many contributions were completed in a fixed time window.

Aggregate performance score data 533 can be generated automatically by a subsystem based on the aggregate efficiency and/or accuracy data. The aggregate performance data can include categorized performance data 534, for example, corresponding to different scan types, different anatomical regions, different subsystems, different interactive interface features and/or display parameters. The categorized performance data 534 can be determined automatically by a subsystem based on the scan type data 421 and/or anatomical region data 422 of the medical scan associated with each contribution, one or more subsystems 101 associated with each contribution, and/or interactive interface feature data 524 associated with each contribution. The aggregate performance data can also be based on performance score data 530 of individual employees if the user corresponds to a medical entity, for example, retrieved based on user profile identifiers 355 included in the employee data 513. The performance score data can also include ranking data 535, which can include an overall ranking or categorized rankings, for example, generated automatically by a subsystem or the database itself based on the aggregate performance data.

In some embodiments, aggregate data for each user can be further broken down based on scores for distinct scan categories, for example, based on the scan classifier data 420, for example, where a first aggregate data score is generated for a user "A" based on scores from all knee x-rays, and a second aggregate data score is generated for user A based on scores from all chest CT scans. Aggregate data for each user can be further based on scores for distinct diagnosis categories, where a first aggregate data score is generated for user A based on scores from all normal scans, and a second aggregate data score is generated for user A based on scores from all scans that contain an abnormality. This can be further broken down, where a first aggregate score is generated for user A based on all scores from scans that contain an abnormality of a first type and/or in a first anatomical location, and a second aggregate score is generated for A based on all scores from scans that contain an abnormality of a second type and/or in a second location. Aggregate data for each user can be further based on affiliation data, where a ranking is generated for a medical professional "B" based on scores from all medical professionals with the same affiliation data, and/or where a ranking is generated for a hospital "C" based on scores for all hospitals, all hospitals in the same geographical region, etc. Aggregate data for each user can be further based on scores for interface features, where a first aggregate data score is generated for user A based on scores using a first interface feature, and a second aggregate data score is generated for user A based on scores using a first interface feature.

The user profile entry can include qualification data 540. The qualification data can include experience data 541 such as education data, professional practice data, number of years practicing, awards received, etc. The qualification data 540 can also include certification data 542 corresponding to certifications earned based on contributions to one or more subsystems, for example, assigned to users automatically by a subsystem based on the performance score data 530 and/or based on a number of contributions in the contribution usage data 523 and/or training usage data 522. For example, the certifications can correspond to standard and/or recognized certifications to train medical professionals and/or incentivize medical professionals to use the system. The qualification data 540 can include expert data 543. The expert data 543 can include a binary expert identifier, which can be generated automatically by a subsystem based on experience data 541, certification data 542, and/or the performance score data 530, and can indicate whether the user is an expert user. The expert data 543 can include a plurality of categorized binary expert identifiers corresponding to a plurality of qualification categories corresponding to corresponding to scan types, anatomical regions, and/or the particular subsystems. The categorized binary expert identifiers can be generated automatically by a subsystem based on the categorized performance data 534 and/or the experience data 541. The categories be ranked by performance score in each category to indicate particular specialties. The expert data 543 can also include an expert ranking or categorized expert ranking with respect to all experts in the system.

The user profile entry can include subscription data 550, which can include a selected one of a plurality of subscription options that the user has subscribed to. For example, the subscription options can correspond to allowed usage of one or more subsystems, such as a number of times a user can utilize a subsystem in a month, and/or to a certification program, for example paid for by a user to receive training to earn a subsystem certification of certification data 542. The subscription data can include subscription expiration information, and/or billing information. The subscription data can also include subscription status data 551, which can for example indicate a number of remaining usages of a system and/or available credit information. For example, the remaining number of usages can decrease and/or available credit can decrease in response to usages that utilize one or more subsystems as a service, for example, indicated in the consumption usage data 521 and/or training usage data 522. In some embodiments, the remaining number of usages can increase and/or available credit can increase in response to usages that correspond to contributions, for example, based on the contribution usage data 523. An increase in credit can be variable, and can be based on a determined quality of each contribution, for example, based on the performance score data 530 corresponding to the contribution where a higher performance score corresponds to a higher increase in credit, based on scan priority data 427 of the medical scan where contributing to higher priority scans corresponds to a higher increase in credit, or based on other factors.

The user profile entry 354 can include interface preference data 560. The interface preference data can include a preferred interactive interface feature set 561, which can include one or more interactive interface feature identifiers and/or one or more interactive interface version identifiers of interface feature entries 358 and/or version identifiers of the interface features. Some or all of the interface features of the preferred interactive interface feature set 561 can correspond to display parameter data 470 of medical scans. The preferred interactive interface feature set 561 can include a single interactive feature identifier for one or more feature types and/or interface types, and/or can include a single interactive interface version identifier for one or more interface categories. The preferred interactive interface feature set 561 can include a ranking of multiple features for the same feature type and/or interface type. The ranked and/or unranked preferred interactive interface feature set 561 can be generated based on user input to an interactive interface of the client device to select and/or rank some or all of the interface features and/or versions. Some or all of the features and/or versions of the preferred interactive feature set can be selected and/or ranked automatically by a subsystem such as the medical scan interface evaluator system, for example based on interface feature performance score data and/or feature popularity data. Alternatively or in addition, the performance score data 530 can be utilized by a subsystem to automatically determine the preferred interactive feature set, for example, based on the scores in different feature-based categories of the categorized performance data 534.

The user profile entry 354 can include report formatting data 570, which can indicate report formatting preferences indicated by the user. This can include font, text size, header data, bulleting or numbering type, margins, file type, preferences for including one or more full or cropped image slices 412, preferences for including similar medical scans, preferences for including additional medical scans in reports, or other formatting preference to list natural language text data and/or image data corresponding to each abnormality. Some or all of the report formatting data 570 can be based on interface preference data 560. The report formatting data 570 can be used by one or more subsystems to automatically generate report data 449 of medical scans based on the preferences of the requesting user.

Figure 5B:
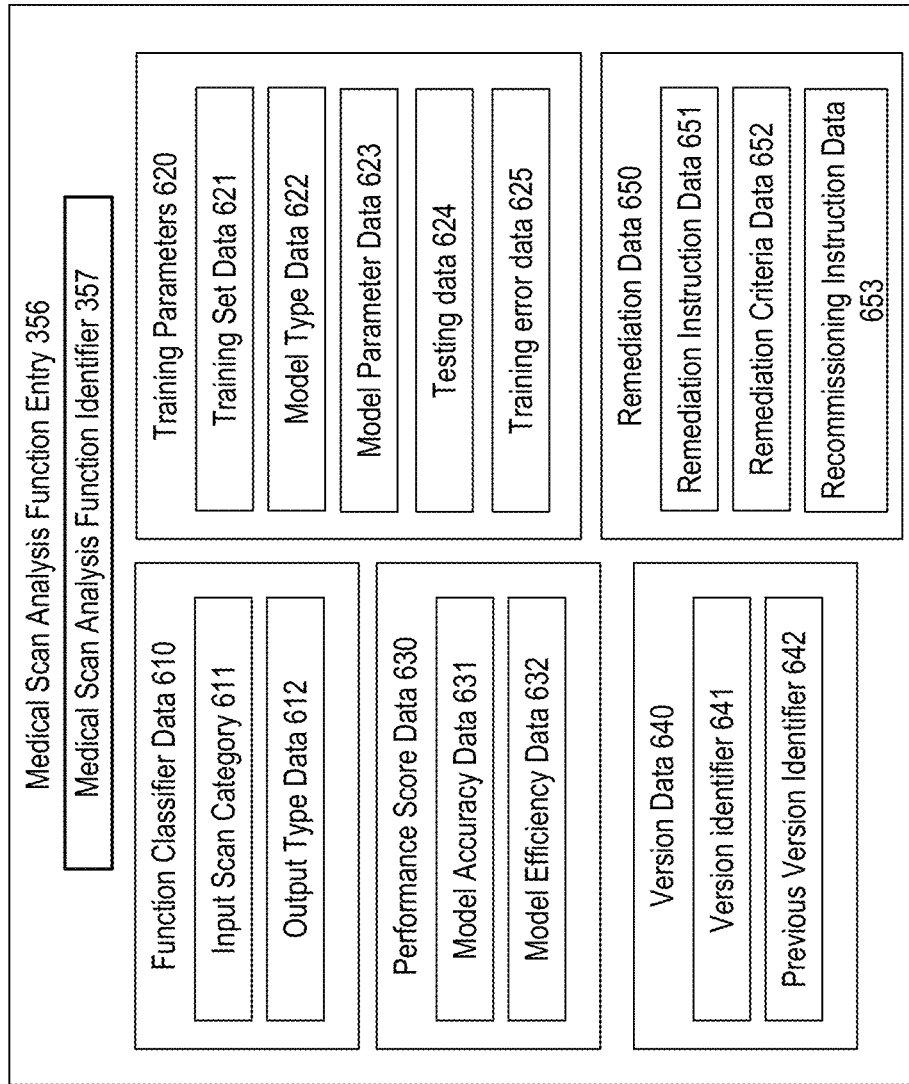
FIG. 5B is a schematic block diagram of a medical scan analysis function entry in accordance with various embodiments.

FIG. 5B presents an embodiment of a medical scan analysis function entry 356, stored in medical scan analysis function database 346 or otherwise associated with one of a plurality of medical scan analysis functions trained by and/or utilized by one or more subsystems 101. For example, a medical scan analysis function can include one or more medical scan image analysis functions trained by the medical scan image analysis system 112; one or more medical scan natural language analysis functions trained by the medical scan natural language analysis system 114; one or more medical scan similarity analysis function trained by the medical scan image analysis system 112, the medical scan natural language analysis system 114, and/or the medical scan comparison system 116; one or more medical report generator functions trained by the medical scan natural language analysis system 114 and/or the medical scan image analysis system 112, and/or the medical report analysis function trained by the medical scan natural language analysis system 114. Some or all of the medical scan analysis functions can correspond to medical scan inference functions of the medical scan diagnosing system 108, the de-identification function and/or the inference functions utilized by a medical picture archive integration system as discussed in conjunction with FIGS. 8A-8F, or other functions and/or processes described herein in conjunction with one or more subsystems 101. Each medical scan analysis function entry 356 can include a medical scan analysis function identifier 357.

A medical scan analysis function entry 356 can include function classifier data 610. Function classifier data 610 can include input and output types corresponding to the function. For example the function classifier data can include input scan category 611 that indicates which types of scans can be used as input to the medical scan analysis function. For example, input scan category 611 can indicate that a medical scan analysis function is for chest CT scans from a particular hospital or other medical entity. The input scan category 611 can include one or more categories included in scan classifier data 420. In various embodiments, the input scan category 611 corresponds to the types of medical scans that were used to train the medical scan analysis function. Function classifier data 610 can also include output type data 612 that characterizes the type of output that will be produced by the function, for example, indicating that a medical scan analysis function is used to generate medical codes 447. The input scan category 611 can also include information identifying which subsystems 101 are responsible for running the medical scan analysis function.

A medical scan analysis function entry 356 can include training parameters 620. This can include training set data 621, which can include identifiers for the data used to train the medical scan analysis function, such as a set of medical scan identifiers 353 corresponding to the medical scans used to train the medical scan analysis function, a list of medical scan reports and corresponding medical codes used to train the medical scan analysis function, etc. Alternatively or in addition to identifying particular scans of the training set, the training set data 621 can identify training set criteria, such as necessary scan classifier data 420, necessary abnormality locations, classifiers, or other criteria corresponding to abnormality annotation data 442, necessary confidence score data 460, for example, indicating that only medical scans with diagnosis data 440 assigned a truth flag 461 or with confidence score data 460 otherwise comparing favorably to a training set confidence score threshold are included, a number of medical scans to be included and proportion data corresponding to different criteria, or other criteria used to populate a training set with data of medical scans. Training parameters 620 can include model type data 622 indicating one or more types of model, methods, and/or training functions used to determine the medical scan analysis function by utilizing the training set 621. Training parameters 620 can include model parameter data 623 that can include a set of features of the training data selected to train the medical scan analysis function, determined values for weights corresponding to selected input and output features, determined values for model parameters corresponding to the model itself, etc. The training parameter data can also include testing data 624, which can identify a test set of medical scans or other data used to test the medical scan analysis function. The test set can be a subset of training set 621, include completely separate data than training set 621, and/or overlap with training set 621. Alternatively or in addition, testing data 624 can include validation parameters such as a percentage of data that will be randomly or pseudo-randomly selected from the training set for testing, parameters characterizing a cross validation process, or other information regarding testing. Training parameters 620 can also include training error data 625 that indicates a training error associated with the medical scan analysis function, for example, based on applying cross validation indicated in testing data 624.

A medical scan analysis function entry 356 can include performance score data 630. Performance data can include model accuracy data 631, for example, generated and/or updated based on the accuracy of the function when performed on new data. For example, the model accuracy data 631 can include or be calculated based on the model error for determined for individual uses, for example, generated by comparing the output of the medical scan analysis function to corresponding data generated by user input to interactive interface 275 in conjunction with a subsystem 101 and/or generated by comparing the output of the medical scan analysis function to medical scans with a truth flag 461. The model accuracy data 631 can include aggregate model accuracy data computed based on model error of individual uses of the function over time. The performance score data 630 can also include model efficiency data 632, which can be generated based on how quickly the medical scan analysis function performs, how much memory is utilized by medical scan analysis function, or other efficiency data relating to the medical scan analysis function. Some or all of the performance score data 630 can be based on training error data 625 or other accuracy and/or efficiency data determined during training and/or validation. As used herein, a "high" performance score refers to a more favorable performance or rating than a "low" performance score.

A medical scan analysis function entry 356 can include version data 640. The version data can include a version identifier 641. The version data can indicate one or more previous version identifiers 642, which can map to version identifiers 641 stored in other medical scan analysis function entry 356 that correspond to previous versions of the function. Alternatively or in addition, the version data can indicate multiple versions of the same type based on function classifier data 610, can indicate the corresponding order and/or rank of the versions, and/or can indicate training parameters 620 associated with each version.

A medical scan analysis function entry 356 can include remediation data 650. Remediation data 650 can include remediation instruction data 651 which can indicate the steps in a remediation process indicating how a medical scan analysis function is taken out of commission and/or reverted to a previous version in the case that remediation is necessary. The version data 640 can further include remediation criteria data 652, which can include threshold data or other criteria used to automatically determine when remediation is necessary. For example, the remediation criteria data 652 can indicate that remediation is necessary at any time where the model accuracy data and/or the model efficiency data compares unfavorably to an indicated model accuracy threshold and/or indicated model efficiency threshold. The remediation data 650 can also include recommissioning instruction data 653, identifying required criteria for recommissioning a medical scan analysis function and/or updating a medical scan analysis function. The remediation data 650 can also include remediation history, indicating one or more instances that the medical scan analysis function was taken out of commission and/or was recommissioned.

Figure 6A:
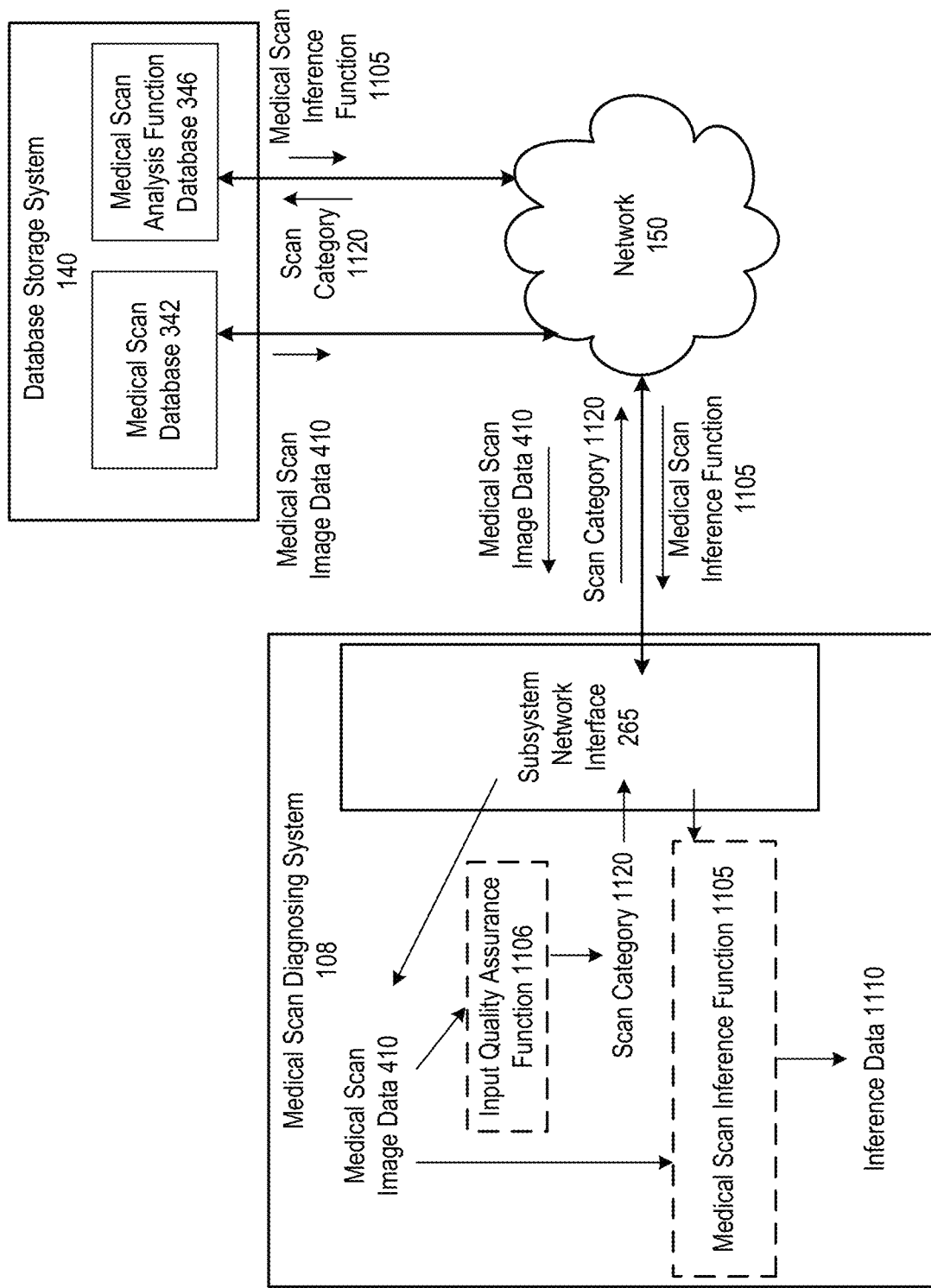
FIGS. 6A-6B are schematic block diagram of a medical scan diagnosing system in accordance with various embodiments.
Figure 6B:
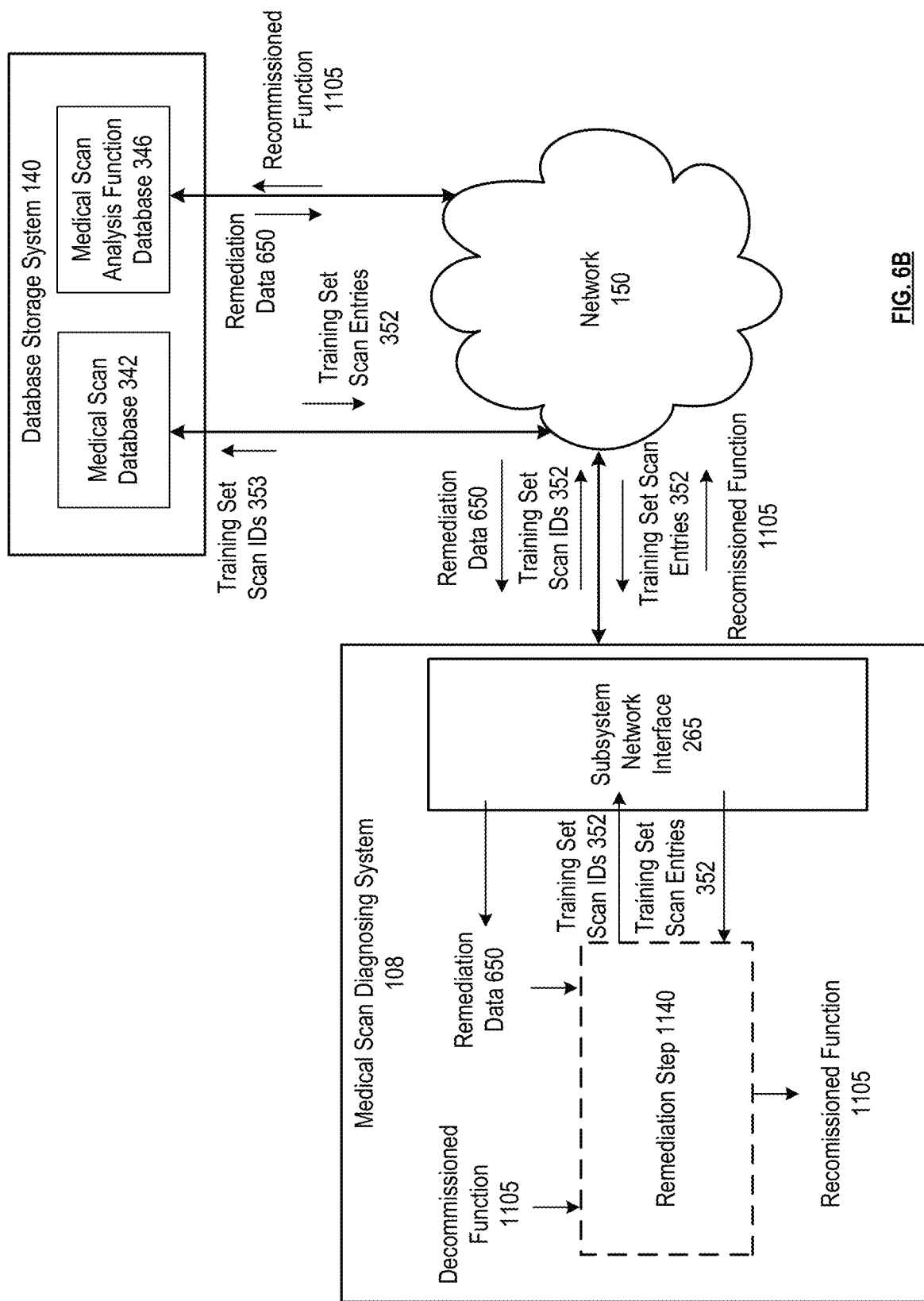

FIGS. 6A and 6B present an embodiment of a medical scan diagnosing system 108.

The medical scan diagnosing system 108 can generate inference data 1110 for medical scans by utilizing a set of medical scan inference functions 1105, stored and run locally, stored and run by another subsystem 101, and/or stored in the medical scan analysis function database 346, where the function and/or parameters of the function can be retrieved from the database by the medical scan diagnosing system. For example, the set of medical scan inference function 1105 can include some or all medical scan analysis functions described herein or other functions that generate inference data 1110 based on some or all data corresponding to a medical scan such as some or all data of a medical scan entry 352. Each medical scan inference function 1105 in the set can correspond to a scan category 1120, and can be trained on a set of medical scans that compare favorably to the scan category 1120. For example, each inference function can be trained on a set of medical scans of the one or more same scan classifier data 420, such as the same and/or similar scan types, same and/or similar anatomical regions locations, same and/or similar machine models, same and/or similar machine calibration, same and/or similar contrasting agent used, same and/or similar originating entity, same and/or similar geographical region, and/or other classifiers. Thus, the scan categories 1120 can correspond to one or more of a scan type, scan anatomical region data, hospital or other originating entity data, machine model data, machine calibration data, contrast agent data, geographic region data, and/or other scan classifying data 420. For example, a first medical scan inference function can be directed to characterizing knee x-rays, and a second medical scan inference function can be directed to chest CT scans. As another example, a first medical scan inference function can be directed to characterizing CT scans from a first hospital, and a second medical scan image analysis function can be directed to characterizing CT scans from a second hospital.

Training on these categorized sets separately can ensure each medical scan inference function 1105 is calibrated according to its scan category 1120, for example, allowing different inference functions to be calibrated on type specific, anatomical region specific, hospital specific, machine model specific, and/or region-specific tendencies and/or discrepancies. Some or all of the medical scan inference functions 1105 can be trained by the medical scan image analysis system and/or the medical scan natural language processing system, and/or some medical scan inference functions 1105 can utilize both image analysis and natural language analysis techniques to generate inference data 1110. For example, some or all of the inference functions can utilize image analysis of the medical scan image data 410 and/or natural language data extracted from abnormality annotation data 442 and/or report data 449 as input, and generate diagnosis data 440 such as medical codes 447 as output. Each medical scan inference function can utilize the same or different learning models to train on the same or different features of the medical scan data, with the same or different model parameters, for example indicated in the model type data 622 and model parameter data 623. Model type and/or parameters can be selected for a particular medical scan inference function based on particular characteristics of the one or more corresponding scan categories 1120, and some or all of the indicated in the model type data 622 and model parameter data 623 can be selected automatically by a subsystem during the training process based on the particular learned and/or otherwise determined characteristics of the one or more corresponding scan categories 1120.

As shown in FIG. 6A, the medical scan diagnosing system 108 can automatically select a medical scan for processing in response to receiving it from a medical entity via the network. Alternatively, the medical scan diagnosing system 108 can automatically retrieve a medical scan from the medical scan database that is selected based on a request received from a user for a particular scan and/or based on a queue of scans automatically ordered by the medical scan diagnosing system 108 or another subsystem based on scan priority data 427.

Once a medical scan to be processed is determined, the medical scan diagnosing system 108 can automatically select an inference function 1105 based on a determined scan category 1120 of the selected medical scan and based on corresponding inference function scan categories. The scan category 1120 of a scan can be determined based one some or all of the scan classifier data 420 and/or based on other metadata associated with the scan. This can include determining which one of the plurality of medical scan inference functions 1105 matches or otherwise compares favorably to the scan category 1120, for example, by comparing the scan category 1120 to the input scan category of the function classifier data 610.

Alternatively or in addition, the medical scan diagnosing system 108 can automatically determine which medical scan inference function 1105 is utilized based on an output preference that corresponding to a desired type of inference data 1110 that is outputted by an inference function 1105. The output preference designated by a user of the medical scan diagnosing system 108 and/or based on the function of a subsystem 101 utilizing the medical scan diagnosing system 108. For example, the set of inference functions 1105 can include inference functions that are utilized to indicate whether or not a medical scan is normal, to automatically identify at least one abnormality in the scan, to automatically characterize the at least one abnormality in the scan, to assign one or more medical codes to the scan, to generate natural language text data and/or a formatted report for the scan, and/or to automatically generate other diagnosis data such as some or all of diagnosis data 440 based on the medical scan. Alternatively or in addition, some inference functions can also be utilized to automatically generate confidence score data 460, display parameter data 470, and/or similar scan data 480. The medical scan diagnosing system 108 can compare the output preference to the output type data 612 of the medical scan inference function 1105 to determine the selected inference function 1105. For example, this can be used to decide between a first medical scan inference function that automatically generates medical codes and a second medical scan inference function that automatically generates natural language text for medical reports based on the desired type of inference data 1110.

Prior to performing the selected medical scan inference function 1105, the medical scan diagnosing system 108 can automatically perform an input quality assurance function 1106 to ensure the scan classifier data 420 or other metadata of the medical scan accurately classifies the medical scan such that the appropriate medical scan inference function 1105 of the appropriate scan category 1120 is selected. The input quality assurance function can be trained on, for example, medical scan image data 410 of plurality of previous medical scans with verified scan categories. Thus, the input quality assurance function 1106 can take medical scan image data 410 as input and can generate an inferred scan category as output. The inferred scan category can be compared to the scan category 1120 of the scan, and the input quality assurance function 1106 can determine whether or not the scan category 1120 is appropriate by determining whether the scan category 1120 compares favorably to the automatically generated inferred scan category. The input quality assurance function 1106 can also be utilized to reassign the generated inferred scan category to the scan category 1120 when the scan category 1120 compares favorably to the automatically generated inferred scan category. The input quality assurance function 1106 can also be utilized to assign the generated inferred scan category to the scan category 1120 for incoming medical scans that do not include any classifying data, and/or to add classifiers in scan classifier data 420 to medical scans missing one or more classifiers.

In various embodiments, upon utilizing the input quality assurance function 1106 to determine that the scan category 1120 determined by a scan classifier data 420 or other metadata is inaccurate, the medical scan diagnosing system 108 can transmit an alert and/or an automatically generated inferred scan category to the medical entity indicating that the scan is incorrectly classified in the scan classifier data 420 or other metadata. In some embodiments, the medical scan diagnosing system 108 can automatically update performance score data corresponding to the originating entity of the scan indicated in originating entity data 423, or another user or entity responsible for classifying the scan, for example, where a lower performance score is generated in response to determining that the scan was incorrectly classified and/or where a higher performance score is generated in response to determining that the scan was correctly classified.

In some embodiments, the medical scan diagnosing system 108 can transmit the medical scan and/or the automatically generated inferred scan category to a selected user. The user can be presented the medical scan image data 410 and/or other data of the medical scan via the interactive interface 275, for example, displayed in conjunction with the medical scan assisted review system 102. The interface can prompt the user to indicate the appropriate scan category 1120 and/or prompt the user to confirm and/or edit the inferred scan category, also presented to the user. For example, scan review data can be automatically generated to reflect the user generated and/or verified scan category 1120, This user indicated scan category 1120 can be utilized to select to the medical scan inference function 1105 and/or to update the scan classifier data 420 or other metadata accordingly. In some embodiments, for example, where the scan review data indicates that the selected user disagrees with the automatically generated inferred scan category created by the input quality assurance function 1106, the medical scan diagnosing system 108 can automatically update performance score data 630 of the input quality assurance function 1106 by generating a low performance score and/or determine to enter the remediation step 1140 for the input quality assurance function 1106.

The medical scan diagnosing system 108 can also automatically perform an output quality assurance step after a medical scan inference function 1105 has been performed on a medical scan to produce the inference data 1110, as illustrated in the embodiment presented in FIG. 6B. The output quality assurance step can be utilized to ensure that the selected medical scan inference function 1105 generated appropriate inference data 1110 based on expert feedback. The inference data 1110 generated by performing the selected medical scan inference function 1105 can be sent to a client device 120 of a selected expert user, such as an expert user in the user database selected based on categorized performance data and/or qualification data that corresponds to the scan category 1120 and/or the inference itself, for example, by selecting an expert user best suited to review an identified abnormality classifier category 444 and/or abnormality pattern category 446 in the inference data 1110 based on categorized performance data and/or qualification data of a corresponding user entry. The selected user can also correspond to a medical professional or other user employed at the originating entity and/or corresponding to the originating medical professional, indicated in the originating entity data 423.

FIG. 6B illustrates an embodiment of the medical scan diagnosing system 108 in conjunction with performing a remediation step 1140. The medical scan diagnosing system 108 can monitor the performance of the set of medical scan inference functions 1105, for example, based on evaluating inference accuracy data outputted by an inference data evaluation function and/or based monitoring on the performance score data 630 in the medical scan analysis function database, and can determine whether or not if the corresponding medical scan inference function 1105 is performing properly. This can include, for example, determining if a remediation step 1140 is necessary for a medical scan inference function 1105, for example, by comparing the performance score data 630 and/or inference accuracy data to remediation criteria data 652. Determining if a remediation step 1140 is necessary can also be based on receiving an indication from the expert user or another user that remediation is necessary for one or more identified medical scan inference functions 1105 and/or for all of the medical scan inference functions 1105.

In various embodiments, a remediation evaluation function is utilized to determine if a remediation step 1140 is necessary for medical scan inference function 1105. The remediation evaluation function can include determining that remediation is necessary when recent accuracy data and/or efficiency data of a particular medical scan inference function 1105 is below the normal performance level of the particular inference function. The remediation evaluation function can include determining that remediation is necessary when recent or overall accuracy data and/or efficiency data of a particular medical scan inference function 1105 is below a recent or overall average for all or similar medical scan inference functions 1105. The remediation evaluation function can include determining that remediation is necessary only after a threshold number of incorrect diagnoses are made. In various embodiments, multiple threshold number of incorrect diagnoses correspond to different diagnoses categories. For example, the threshold number of incorrect diagnoses for remediation can be higher for false negative diagnoses than false positive diagnoses. Similarly, categories corresponding to different diagnosis severities and/or rarities can have different thresholds, for example where a threshold number of more severe and/or more rare diagnoses that were inaccurate to necessitate remediation is lower than a threshold number of less severe and/or less rare diagnoses that were inaccurate.

The remediation step 1140 can include automatically updating an identified medical inference function 1105. This can include automatically retraining identified medical inference function 1105 on the same training set or on a new training set that includes new data, data with higher corresponding confidence scores, or data selected based on new training set criteria. The identified medical inference function 1105 can also be updated and/or changed based on the review data received from the client device. For example, the medical scan and expert feedback data can be added to the training set of the medical scan inference function 1105, and the medical scan inference function 1105 can be retrained on the updated training set. Alternatively or in addition, the expert user can identify additional parameters and/or rules in the expert feedback data based on the errors made by the inference function in generating the inference data 1110 for the medical scan, and these parameters and/or rules can be applied to update the medical scan inference function, for example, by updating the model type data 622 and/or model parameter data 623.

The remediation step 1140 can also include determining to split a scan category 1120 into two or more subcategories. Thus, two or more new medical scan inference functions 1105 can be created, where each new medical scan inference functions 1105 is trained on a corresponding training set that is a subset of the original training set and/or includes new medical scan data corresponding to the subcategory. This can allow medical scan inference functions 1105 to become more specialized and/or allow functions to utilize characteristics and/or discrepancies specific to the subcategory when generating inference data 1110. Similarly, a new scan category 1120 that was not previously represented by any of the medical scan inference functions 1105 can be added in the remediation step, and a new medical scan inference functions 1105 can be trained on a new set of medical scan data that corresponds to the new scan category 1120. Splitting a scan category and/or adding a scan category can be determined automatically by the medical scan diagnosing system 108 when performing the remediation step 1140, for example, based on performance score data 630. This can also be determined based on receiving instructions to split a category and/or add a new scan category from the expert user or other user of the system.

After a medical scan inference function 1105 is updated or created for the first time, the remediation step 1140 can further undergo a commissioning test, which can include rigorous testing of the medical scan inference function 1105 on a testing set, for example, based on the training parameters 620. For example, the commissioning test can be passed when the medical scan inference function 1105 generates a threshold number of correct inference data 1110 and/or the test can be passed if an overall or average discrepancy level between the inference data and the test data is below a set error threshold. The commissioning test can also evaluate efficiency, where the medical scan inference function 1105 only passes the commissioning test if it performs at or exceeds a threshold efficiency level. If the medical scan inference function 1105 fails the commissioning test, the model type and/or model parameters can be modified automatically or based on user input, and the medical scan inference function can be retested, continuing this process until the medical scan inference function 1105 passes the commissioning test.

The remediation step 1140 can include decommissioning the medical scan inference function 1105, for example, while the medical scan inference function is being retrained and/or is undergoing the commissioning test. Incoming scans to the medical scan diagnosing system 108 with a scan category 1120 corresponding to a decommissioned medical scan inference function 1105 can be sent directly to review by one or more users, for example, in conjunction with the medical scan annotator system 106. These user-reviewed medical scans and corresponding annotations can be included in an updated training set used to train the decommissioned medical scan inference function 1105 as part of the remediation step 1140. In some embodiments, previous versions of the plurality of medical scan image analysis functions can be stored in memory of the medical scan diagnosing system and/or can be determined based on the version data 640 of a medical scan inference function 1105. A previous version of a medical scan inference function 1105, such as most recent version or version with the highest performance score, can be utilized during the remediation step 1140 as an alternative to sending all medical scans to user review.

A medical scan inference function can also undergo the remediation step 1140 automatically in response to a hardware and/or software update on processing, memory, and/or other computing devices where the medical scan inference function 1105 is stored and/or performed. Different medical scan inference functions 1105 can be containerized on their own devices by utilizing a micro-service architecture, so hardware and/or software updates may only necessitate that one of the medical scan inference functions 1105 undergo the remediation step 1140 while the others remain unaffected. A medical scan inference function 1105 can also undergo the remediation step 1140 automatically in response to normal system boot-up, and/or periodically in fixed intervals. For example, in response to a scheduled or automatically detected hardware and/or software update, change, or issue, one or more medical scan inference functions 1105 affected by this hardware or software can be taken out of commission until they each pass the commissioning test. Such criteria can be indicated in the remediation criteria data 652.

The medical scan diagnosing system 108 can automatically manage usage data, subscription data, and/or billing data for the plurality of users corresponding to user usage of the system, for example, by utilizing, generating, and/or updating some or all of the subscription data of the user database. Users can pay for subscriptions to the system, which can include different subscription levels that can correspond to different costs. For example, a hospital can pay a monthly cost to automatically diagnose up to 100 medical scans per month. The hospital can choose to upgrade their subscription or pay per-scan costs for automatic diagnosing of additional scans received after the quota is reached and/or the medical scan diagnosing system 108 can automatically send medical scans received after the quota is reached to an expert user associated with the hospital. In various embodiments incentive programs can be used by the medical scan diagnosing system to encourage experts to review medical scans from different medical entities. For example, an expert can receive credit to their account and/or subscription upgrades for every medical scan reviewed, or after a threshold number of medical scans are reviewed. The incentive programs can include interactions by a user with other subsystems, for example, based on contributions made to medical scan entries via interaction with other subsystems.

Figure 7A:
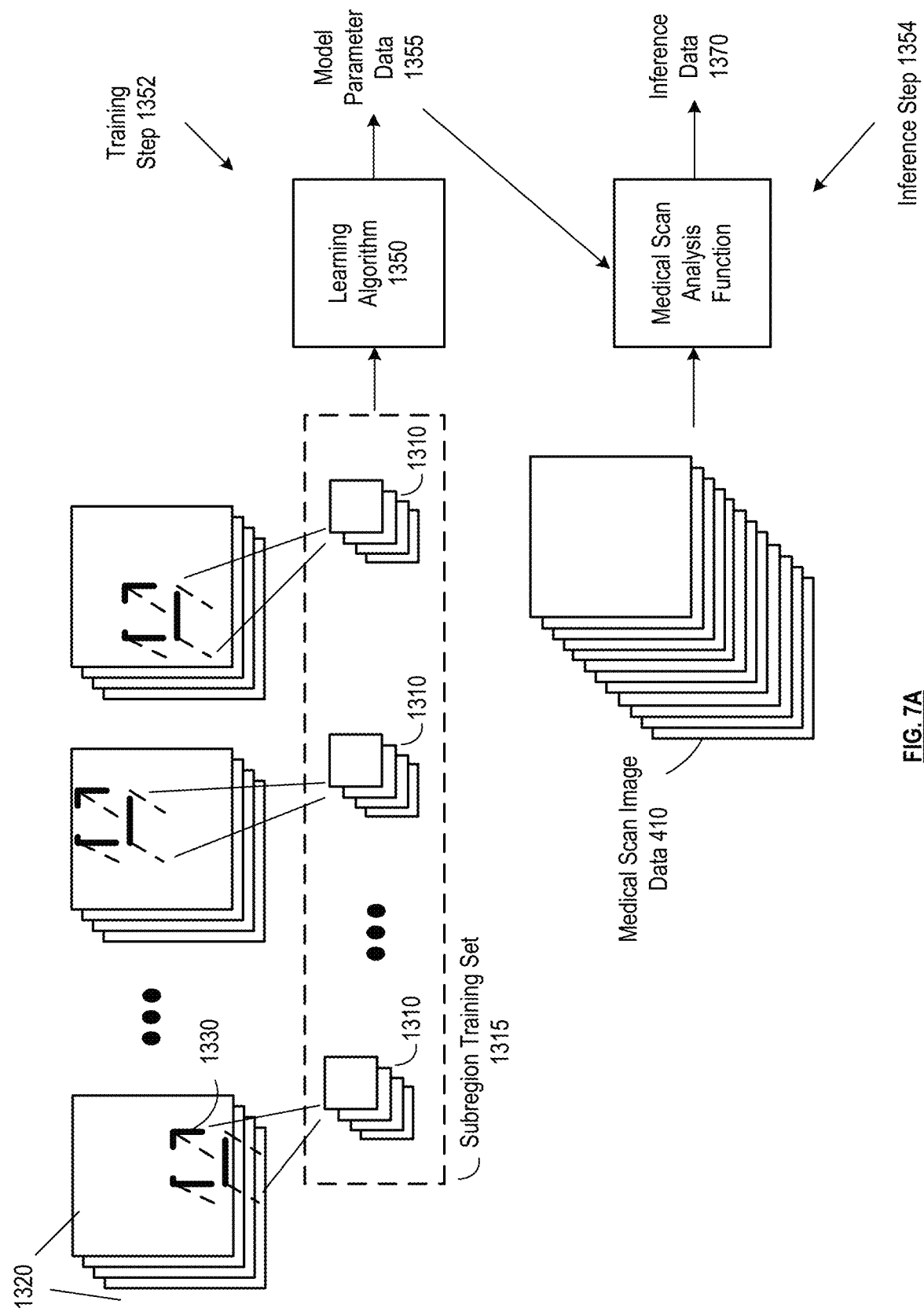
FIG. 7A is a flowchart representation of an inference step in accordance with various embodiments.

FIG. 7A presents an embodiment of a medical scan image analysis system 112. A training set of medical scans used to train one more medical scan image analysis functions can be received from one or more client devices via the network and/or can be retrieved from the medical scan database 342, for example, based on training set data 621 corresponding to medical scan image analysis functions. Training set criteria, for example, identified in training parameters 620 of the medical scan image analysis function, can be utilized to automatically identify and select medical scans to be included in the training set from a plurality of available medical scans. The training set criteria can be automatically generated based on, for example, previously learned criteria, and/or training set criteria can be received via the network, for example, from an administrator of the medical scan image analysis system. The training set criteria can include a minimum training set size. The training set criteria can include data integrity requirements for medical scans in the training set such as requiring that the medical scan is assigned a truth flag 461, requiring that performance score data for a hospital and/or medical professional associated with the medical scan compares favorably to a performance score threshold, requiring that the medical scan has been reviewed by at least a threshold number of medical professionals, requiring that the medical scan and/or a diagnosis corresponding to a patient file of the medical scan is older than a threshold elapsed time period, or based on other criteria intended to insure that the medical scans and associated data in the training set is reliable enough to be considered "truth" data. The training set criteria can include longitudinal requirements such the number of required subsequent medical scans for the patient, multiple required types of additional scans for the patient, and/or other patient file requirements.

The training set criteria can include quota and/or proportion requirements for one or more medical scan classification data. For example, the training set criteria can include meeting quota and/or proportion requirements for one or more scan types and/or human body location of scans, meeting quota or proportion requirements for a number of normal medical scans and a number of medicals scans with identified abnormalities, meeting quota and/or proportion requirements for a number of medical scans with abnormalities in certain locations and/or a number of medical scans with abnormalities that meet certain size, type, or other characteristics, meeting quota and/or proportion data for a number of medical scans with certain diagnosis or certain corresponding medical codes, and/or meeting other identified quota and/or proportion data relating to metadata, patient data, or other data associated with the medical scans.

In some embodiments, multiple training sets are created to generate corresponding medical scan image analysis functions, for example, corresponding to some or all of the set of medical scan inference functions 1105. Some or all training sets can be categorized based on some or all of the scan classifier data 420 as described in conjunction with the medical scan diagnosing system 108, where medical scans are included in a training set based on their scan classifier data 420 matching the scan category of the training set. In some embodiments, the input quality assurance function 1106 or another input check step can be performed on medical scans selected for each training set to confirm that their corresponding scan classifier data 420 is correct. In some embodiments, the input quality assurance function can correspond to its own medical scan image analysis function, trained by the medical scan image analysis system, where the input quality assurance function utilizes high level computer vision technology to determine a scan category 1120 and/or to confirm the scan classifier data 420 already assigned to the medical scan.

In some embodiments, the training set will be used to create a single neural network model, or other model corresponding to model type data 622 and/or model parameter data 623 of the medical scan image analysis function that can be trained on some or all of the medical scan classification data described above and/or other metadata, patient data, or other data associated with the medical scans. In other embodiments, a plurality of training sets will be created to generate a plurality of corresponding neural network models, where the multiple training sets are divided based on some or all of the medical scan classification data described above and/or other metadata, patient data, or other data associated with the medical scans. Each of the plurality of neural network models can be generated based on the same or different learning algorithm that utilizes the same or different features of the medical scans in the corresponding one of the plurality of training sets. The medical scan classifications selected to segregate the medical scans into multiple training sets can be received via the network, for example based on input to an administrator client device from an administrator. The medical scan classifications selected to segregate the medical scans can be automatically determined by the medical scan image analysis system, for example, where an unsupervised clustering algorithm is applied to the original training set to determine appropriate medical scan classifications based on the output of the unsupervised clustering algorithm.

In embodiments where the medical scan image analysis system is used in conjunction with the medical scan diagnosing system, each of the medical scan image analysis functions associated with each neural network model can correspond to one of the plurality of neural network models generated by the medical scan image analysis system. For example, each of the plurality of neural network models can be trained on a training set classified on scan type, scan human body location, hospital or other originating entity data, machine model data, machine calibration data, contrast agent data, geographic region data, and/or other scan classifying data as discussed in conjunction with the medical scan diagnosing system. In embodiments where the training set classifiers are learned, the medical scan diagnosing system can determine which of the medical scan image analysis functions should be applied based on the learned classifying criteria used to segregate the original training set.

A computer vision-based learning algorithm used to create each neural network model can include selecting a three-dimensional subregion 1310 for each medical scan in the training set. This three-dimensional subregion 1310 can correspond to a region that is "sampled" from the entire scan that may represent a small fraction of the entire scan. Recall that a medical scan can include a plurality of ordered cross-sectional image slices. Selecting a three-dimensional subregion 1310 can be accomplished by selecting a proper image slice subset 1320 of the plurality of cross-sectional image slices from each of the plurality of medical scans, and by further selecting a two-dimensional subregion 1330 from each of the selected subset of cross-sectional image slices of the each of the medical scans. In some embodiments, the selected image slices can include one or more non-consecutive image slices and thus a plurality of disconnected three-dimensional subregions will be created. In other embodiments, the selected proper subset of the plurality of image slices correspond to a set of consecutive image slices, as to ensure that a single, connected three-dimensional subregion is selected. In some embodiments, entire scans of the training set are used to train the neural network model. In such embodiment, as used herein, the three-dimensional subregion 1310 can refer to all of the medical scan image data 410 of a medical scan.

In some embodiments, a density windowing step can be applied to the full scan or the selected three-dimensional subregion. The density windowing step can include utilizing a selected upper density value cut off and/or a selected lower density value cut off, and masking pixels with higher values than the upper density value cut off and/or masking pixels with lower values than the lower density value cut off. The upper density value cut off and/or a selected lower density value cut off can be determined based on based on the range and/or distribution of density values included in the region that includes the abnormality, and/or based on the range and/or distribution of density values associated with the abnormality itself, based on user input to a subsystem, based on display parameter data associated with the medical scan or associated with medical scans of the same type, and/or can be learned in the training step. In some embodiments, a non-linear density windowing function can be applied to alter the pixel density values, for example, to stretch or compress contrast. In some embodiments, this density windowing step can be performed as a data augmenting step, to create additional training data for a medical scan in accordance with different density windows.

Having determined the subregion training set 1315 of three-dimensional subregions 1310 corresponding to the set of full medical scans in the training set, the medical scan image analysis system can complete a training step 1352 by performing a learning algorithm on the plurality of three-dimensional subregions to generate model parameter data 1355 of a corresponding learning model. The learning model can include one or more of a neural network, an artificial neural network, a convolutional neural network, a Bayesian model, a support vector machine model, a cluster analysis model, or other supervised or unsupervised learning model. The model parameter data 1355 can generated by performing the learning algorithm 1350, and the model parameter data 1355 can be utilized to determine the corresponding medical scan image analysis functions. For example, some or all of the model parameter data 1355 can be mapped to the medical scan analysis function in the model parameter data 623 or can otherwise define the medical scan analysis function.

The training step 1352 can include creating feature vectors for each three-dimensional subregion of the training set for use by the learning algorithm 1350 to generate the model parameter data 1355. The feature vectors can include the pixel data of the three-dimensional subregions such as density values and/or grayscale values of each pixel based on a determined density window. The feature vectors can also include other features as additional input features or desired output features, such as known abnormality data such as location and/or classification data, patient history data such as risk factor data or previous medical scans, diagnosis data, responsible medical entity data, scan machinery model or calibration data, contrast agent data, medical code data, annotation data that can include raw or processed natural language text data, scan type and/or anatomical region data, or other data associated with the image, such as some or all data of a medical scan entry 352. Features can be selected based on administrator instructions received via the network and/or can be determined based on determining a feature set that reduces error in classifying error, for example, by performing a cross-validation step on multiple models created using different feature sets. The feature vector can be split into an input feature vector and output feature vector. The input feature vector can include data that will be available in subsequent medical scan input, which can include for example, the three-dimensional subregion pixel data and/or patient history data. The output feature vector can include data that will be inferred in in subsequent medical scan input and can include single output value, such as a binary value indicating whether or not the medical scan include an abnormality or a value corresponding to one of a plurality of medical codes corresponding to the image. The output feature vector can also include multiple values which can include abnormality location and/or classification data, diagnosis data, or other output. The output feature vector can also include a determined upper density value cut off and/or lower density value cut off, for example, characterizing which pixel values were relevant to detecting and/or classifying an abnormality. Features included in the output feature vector can be selected to include features that are known in the training set, but may not be known in subsequent medical scans such as triaged scans to be diagnosed by the medical scan diagnosing system, and/or scans to be labeled by the medical scan report labeling system. The set of features in the input feature vector and output feature vector, as well as the importance of different features where each feature is assigned a corresponding weight, can also be designated in the model parameter data 1355.

Consider a medical scan image analysis function that utilizes a neural network. The neural network can include a plurality of layers, where each layer includes a plurality of neural nodes. Each node in one layer can have a connection to some or all nodes in the next layer, where each connection is defined by a weight value. Thus, the model parameter data 1355 can include a weight vector that includes weight values for every connection in the network. Alternatively or in addition, the model parameter data 1355 can include any vector or set of parameters associated with the neural network model, which can include an upper density value cut off and/or lower density value cut off used to mask some of the pixel data of an incoming image, kernel values, filter parameters, bias parameters, and/or parameters characterizing one or more of a plurality of convolution functions of the neural network model. The medical scan image analysis function can be utilized to produce the output vector as a function of the input feature vector and the model parameter data 1355 that characterizes the neural network model. In particular, the medical scan image analysis function can include performing a forward propagation step plurality of neural network layers to produce an inferred output vector based on the weight vector or other model parameter data 1355. Thus, the learning algorithm 1350 utilized in conjunction with a neural network model can include determining the model parameter data 1355 corresponding to the neural network model, for example, by populating the weight vector with optimal weights that best reduce output error.

In particular, determining the model parameter data 1355 can include utilizing a backpropagation strategy. The forward propagation algorithm can be performed on at least one input feature vector corresponding to at least one medical scan in the training set to propagate the at least one input feature vector through the plurality of neural network layers based on initial and/or default model parameter data 1355, such as an initial weight vector of initial weight values set by an administrator or chosen at random. The at least one output vector generated by performing the forward propagation algorithm on the at least one input feature vector can be compared to the corresponding at least one known output feature vector to determine an output error. Determining the output error can include, for example, computing a vector distance such as the Euclidian distance, or squared Euclidian distance, between the produced output vector and the known output vector, and/or determining an average output error such as an average Euclidian distance or squared Euclidian distance if multiple input feature vectors were employed. Next, gradient descent can be performed to determine an updated weight vector based on the output error or average output error. This gradient descent step can include computing partial derivatives for the error with respect to each weight, or other parameter in the model parameter data 1355, at each layer starting with the output layer. Chain rule can be utilized to iteratively compute the gradient with respect to each weight or parameter at each previous layer until all weight's gradients are computed. Next updated weights, or other parameters in the model parameter data 1355, are generated by updating each weight based on its corresponding calculated gradient. This process can be repeated on at least one input feature vector, which can include the same or different at least one feature vector used in the previous iteration, based on the updated weight vector and/or other updated parameters in the model parameter data 1355 to create a new updated weight vector and/or other new updated parameters in the model parameter data 1355. This process can continue to repeat until the output error converges, the output error is within a certain error threshold, or another criterion is reached to determine the most recently updated weight vector and/or other model parameter data 1355 is optimal or otherwise determined for selection.

Figure 7B:
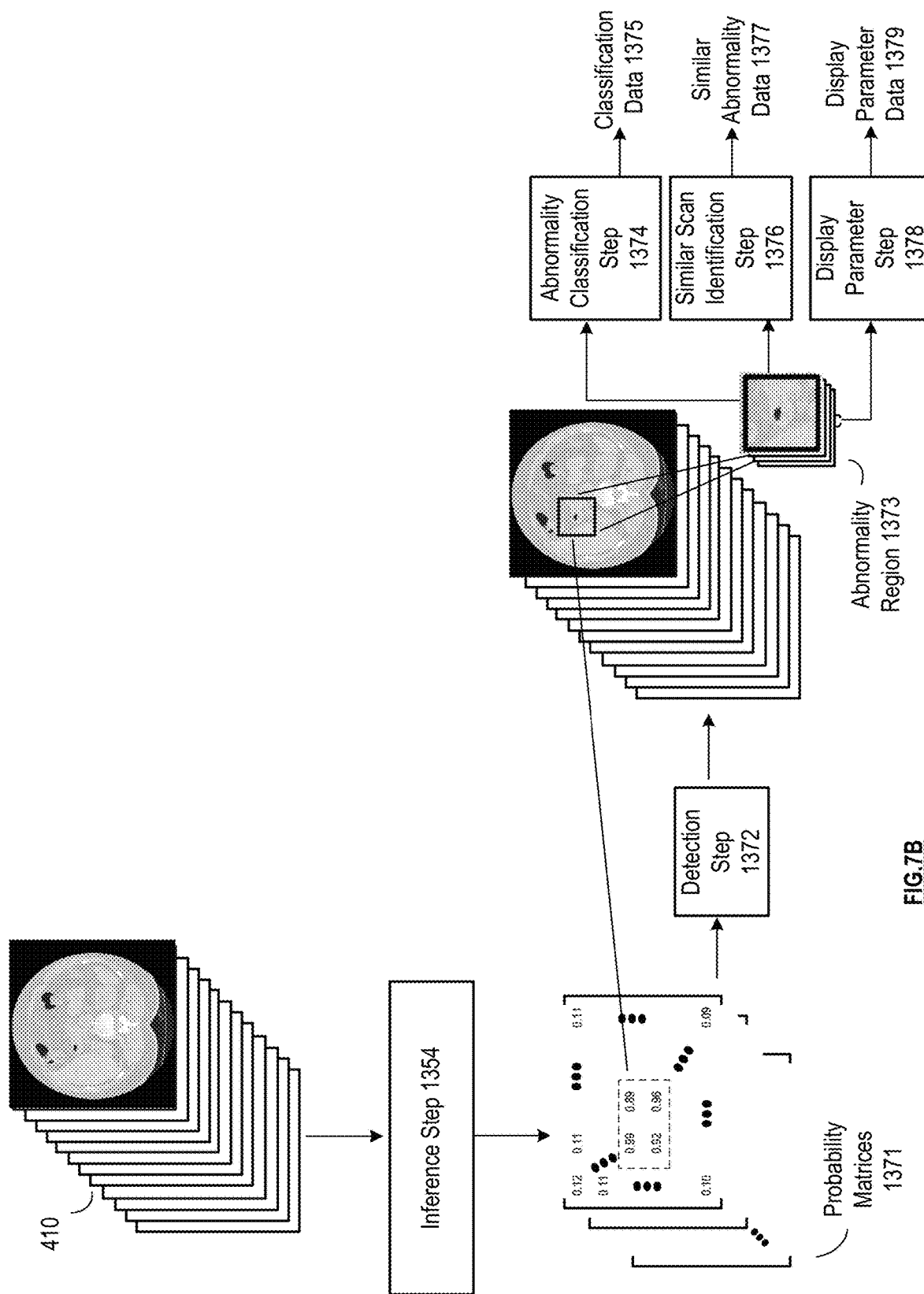
FIG. 7B is a flowchart representation of a detection step in accordance with various embodiments.

Having determined the medical scan neural network and its final other model parameter data 1355, an inference step 1354 can be performed on new medical scans to produce inference data 1370, such as inferred output vectors, as shown in FIG. 7B. The inference step can include performing the forward propagation algorithm to propagate an input feature vector through a plurality of neural network layers based on the final model parameter data 1355, such as the weight values of the final weight vector, to produce the inference data. This inference step 1354 can correspond to performing the medical scan image analysis function, as defined by the final model parameter data 1355, on new medical scans to generate the inference data 1370, for example, in conjunction with the medical scan diagnosing system 108 to generate inferred diagnosis data or other selected output data for triaged medical scans based on its corresponding the input feature vector.

The inference step 1354 can include applying the density windowing step to new medical scans. Density window cut off values and/or a non-linear density windowing function that are learned can be automatically applied when performing the inference step. For example, if the training step 1352 was used to determine optimal upper density value cut off and/or lower density value cut off values to designate an optimal density window, the inference step 1354 can include masking pixels of incoming scans that fall outside of this determined density window before applying the forward propagation algorithm. As another example, if learned parameters of one or more convolutional functions correspond to the optimal upper density value cut off and/or lower density value cut off values, the density windowing step is inherently applied when the forward propagation algorithm is performed on the new medical scans.

In some embodiments where a medical scan analysis function is defined by model parameter data 1355 corresponding to a neutral network model, the neural network model can be a fully convolutional neural network. In such embodiments, only convolution functions are performed to propagate the input feature vector through the layers of the neural network in the forward propagation algorithm. This enables the medical scan image analysis functions to process input feature vectors of any size. For example, as discussed herein, the pixel data corresponding to the three-dimensional subregions is utilized input to the forward propagation algorithm when the training step 1352 is employed to populate the weight vector and/or other model parameter data 1355. However, when performing the forward propagation algorithm in the inference step 1354, the pixel data of full medical scans can be utilized as input, allowing the entire scan to be processed to detect and/or classify abnormalities, or otherwise generate the inference data 1370. This may be a preferred embodiment over other embodiments where new scans must also be sampled by selecting a three-dimensional subregions and/or other embodiments where the inference step requires "piecing together" inference data 1370 corresponding to multiple three-dimensional subregions processed separately.

The inferred output vector of the inference data 1370 can include a plurality of abnormality probabilities mapped to a pixel location of each of a plurality of cross-sectional image slices of the new medical scan. For example, the inferred output vector can indicate a set of probability matrices 1371, where each matrix in the set corresponds to one of the plurality of image slices of the medical scan, where each matrix is a size corresponding to the number of pixels in each image slice, where each cell of each matrix corresponds to a pixel of the corresponding image slice, whose value is the abnormality probability of the corresponding pixel.

A detection step 1372 can include determining if an abnormality is present in the medical scan based on the plurality of abnormality probabilities. Determining if an abnormality is present can include, for example, determining that a cluster of pixels in the same region of the medical scan correspond to high abnormality probabilities, for example, where a threshold proportion of abnormality probabilities must meet or exceed a threshold abnormality probability, where an average abnormality probability of pixels in the region must meet or exceed a threshold abnormality probability, where the region that includes the cluster of pixels must be at least a certain size, etc. Determining if an abnormality is present can also include calculating a confidence score based on the abnormality probabilities and/or other data corresponding to the medical scan such as patient history data. The location of the detected abnormality can be determined in the detection step 1372 based on the location of the pixels with the high abnormality probabilities. The detection step can further include determining an abnormality region 1373, such as a two-dimensional subregion on one or more image slices that includes some or all of the abnormality. The abnormality region 1373 determined in the detection step 1372 can be mapped to the medical scan to populate some or all of the abnormality location data 443 for use by one or more other subsystems 101 and/or client devices 120. Furthermore, determining whether or not an abnormality exists in the detection step 1372 can be used to populate some or all of the diagnosis data 440 of the medical scan, for example, to indicate that the scan is normal or contains an abnormality in the diagnosis data 440.

An abnormality classification step 1374 can be performed on a medical scan in response to determining an abnormality is present. Classification data 1375 corresponding to one or more classification categories such as abnormality size, volume, pre-post contract, doubling time, calcification, components, smoothness, texture, diagnosis data, one or more medical codes, a malignancy rating such as a Lung-RADS score, or other classifying data as described herein can be determined based on the detected abnormality. The classification data 1375 generated by the abnormality classification step 1374 can be mapped to the medical scan to populate some or all of the abnormality classification data 445 of the corresponding abnormality classifier categories 444 and/or abnormality pattern categories 446 and/or to determine one or more medical codes 447 of the medical scan. The abnormality classification step 1374 can include performing an abnormality classification function on the full medical scan, or the abnormality region 1373 determined in the detection step 1372. The abnormality classification function can be based on another model trained on abnormality data such as a support vector machine model, another neural network model, or any supervised classification model trained on medical scans, or portions of medical scans, that include known abnormality classifying data to generate inference data for some or all of the classification categories. For example, the abnormality classification function can include another medical scan analysis function. Classification data 1375 in each of a plurality of classification categories can also be assigned their own calculated confidence score, which can also be generated by utilizing the abnormality classification function. Output to the abnormality classification function can also include at least one identified similar medical scan and/or at least one identified similar cropped image, for example, based on the training data. The abnormality classification step can also be included in the inference step 1354, where the inferred output vector or other inference data 1370 of the medical scan image analysis function includes the classification data 1375.

The abnormality classification function can be trained on full medical scans and/or one or more cropped or full selected image slices from medical scans that contain an abnormality. For example, the abnormality classification function can be trained on a set of two-dimensional cropped slices that include abnormalities. The selected image slices and/or the cropped region in each selected image slice for each scan in the training set can be automatically selected based upon the known location of the abnormality. Input to the abnormality classification function can include the full medical scan, one or more selected full image slices, and/or one or more selected image slices cropped based on a selected region. Thus, the abnormality classification step can include automatically selecting one or more image slices that include the detected abnormality. The slice selection can include selecting the center slice in a set of consecutive slices that are determined to include the abnormality or selecting a slice that has the largest cross-section of the abnormality, or selecting one or more slices based on other criteria. The abnormality classification step can also include automatically generating one or more cropped two-dimensional images corresponding to the one or more of the selected image slices based on an automatically selected region that includes the abnormality.

Input to the abnormality classification function can also include other data associated with the medical scan, including patient history, risk factors, or other metadata. The abnormality classification step can also include determining some or all of the characteristics based on data of the medical scan itself. For example, the abnormality size and volume can be determined based on a number of pixels determined to be part of the detected abnormality. Other classifiers such as abnormality texture and/or smoothness can be determined by performing one or more other preprocessing functions on the image specifically designed to characterize such features. Such preprocessed characteristics can be included in the input to the abnormality classification function to the more difficult task of assigning a medical code or generating other diagnosis data. The training data can also be preprocessed to include such preprocessed features.

A similar scan identification step 1376 can also be performed on a medical scan with a detected abnormality and/or can be performed on the abnormality region 1373 determined in the detection step 1372. The similar scan identification step 1376 can include generating similar abnormality data 1377, for example, by identifying one or more similar medical scans or one or more similar cropped two-dimensional images from a database of medical scans and/or database of cropped two-dimensional images. Similar medical scans and/or cropped images can include medical scans or cropped images that are visually similar, medical scans or cropped images that have known abnormalities in a similar location to an inferred abnormality location of the given medical scan, medical scans that have known abnormalities with similar characteristics to inferred characteristics of an abnormality in the given scan, medical scans with similar patient history and/or similar risk factors, or some combination of these factors and/or other known and/or inferred factors. The similar abnormality data 1377 can be mapped to the medical scan to populate some or all of its corresponding similar scan data 480 for use by one or more other subsystems 101 and/or client devices 120.

The similar scans identification step 1376 can include performing a scan similarity algorithm, which can include generating a feature vector for the given medical scan and for medical scans in the set of medical scans, where the feature vector can be generated based on quantitative and/or category based visual features, inferred features, abnormality location and/or characteristics such as the predetermined size and/or volume, patient history and/or risk factor features, or other known or inferred features. A medical scan similarity analysis function can be applied to the feature vector of the given medical scan and one or more feature vectors of medical scans in the set. The medical scan similarity analysis function can include computing a similarity distance such as the Euclidian distance between the feature vectors, and assigning the similarity distance to the corresponding medical scan in the set. Similar medical scans can be identified based on determining one or more medical scans in the set with a smallest computed similarity distance, based on ranking medical scans in the set based on the computed similarity distances and identifying a designated number of top ranked medical scans, and/or based on determining if a similarity distance between the given medical scan and a medical scan in the set is smaller than a similarity threshold. Similar medical scans can also be identified based on determining medical scans in a database that mapped to a medical code that matches the medical code of the medical scan, or mapped to other matching classifying data. A set of identified similar medical scans can also be filtered based on other inputted or automatically generated criteria, where for example only medical scans with reliable diagnosis data or rich patient reports, medical scans with corresponding with longitudinal data in the patient file such as multiple subsequent scans taken at later dates, medical scans with patient data that corresponds to risk factors of the given patient, or other identified criteria, where only a subset of scans that compare favorably to the criteria are selected from the set and/or only a highest ranked single scan or subset of scans are selected from the set, where the ranking is automatically computed based on the criteria. Filtering the similar scans in this fashion can include calculating, or can be based on previously calculated, one or more scores as discussed herein. For example, the ranking can be based on a longitudinal quality score, such as the longitudinal quality score 434, which can be calculated for an identified medical scan based on a number of subsequent and/or previous scans for the patient. Alternatively or in addition, the ranking can be based on a confidence score associated with diagnosis data of the scan, such as confidence score data 460, based on performance score data associated with a user or medical entity associated with the scan, based on an amount of patient history data or data in the medical scan entry 352, or other quality factors. The identified similar medical scans can be filtered based on ranking the scans based on their quality score and/or based on comparing their quality score to a quality score threshold. In some embodiments, a longitudinal threshold must be reached, and only scans that compare favorably to the longitudinal threshold will be selected. For example, only scans with at least three scans on file for the patient and final biopsy data will be included.

In some embodiments, the similarity algorithm can be utilized in addition to or instead of the trained abnormality classification function to determine some or all of the inferred classification data 1375 of the medical scan, based on the classification data such as abnormality classification data 445 or other diagnosis data 440 mapped to one or more of the identified similar scans. In other embodiments, the similarity algorithm is merely used to identify similar scans for review by medical professionals to aid in review, diagnosis, and/or generating medical reports for the medical image.

A display parameter step 1378 can be performed based on the detection and/or classification of the abnormality. The display parameter step can include generating display parameter data 1379, which can include parameters that can be used by an interactive interface to best display each abnormality. The same or different display parameters can be generated for each abnormality. The display parameter data generated in the display parameter step 1378 can be mapped to the medical scan to populate some or all of its corresponding display parameter data 470 for use by one or more other subsystems 101 and/or client devices 120.

Performing the display parameter step 1378 can include selecting one or more image slices that include the abnormality by determining the one or more image slices that include the abnormality and/or determining one or more image slices that has a most optimal two-dimensional view of the abnormality, for example by selecting the center slice in a set of consecutive slices that are determined to include the abnormality, selecting a slice that has the largest cross-section of the abnormality, selecting a slice that includes a two-dimensional image of the abnormality that is most similar to a selected most similar two-dimensional-image, selecting the slice that was used as input to the abnormality classification step and/or similar scan identification step, or based on other criteria. This can also include automatically cropping one or more selected image slices based on an identified region that includes the abnormality. This can also select an ideal Hounsfield window that best displays the abnormality. This can also include selecting other display parameters based on data generated by the medical scan interface evaluating system and based on the medical scan.

FIGS. 8A-8F illustrate embodiments of a medical picture archive integration system 2600. The medical picture archive integration system 2600 can provide integration support for a medical picture archive system 2620, such as a PACS that stores medical scans. The medical picture archive integration system 2600 can utilize model parameters received from a central server system 2640 via a network 2630 to perform an inference function on de-identified medical scans of medical scans received from the medical picture archive system 2620. The annotation data produced by performing the inference function can be transmitted back to the medical picture archive system. Furthermore, the annotation data and/or de-identified medical scans can be sent to the central server system 2640, and the central server system can train on this information to produce new and/or updated model parameters for transmission back to the medical picture archive integration system 2600 for use on subsequently received medical scans.

In various embodiments, medical picture archive integration system 2600 includes a de-identification system that includes a first memory designated for protected health information (PHI), operable to perform a de-identification function on a DICOM image, received from a medical picture archive system, to identify at least one patient identifier and generate a de-identified medical scan that does not include the at least one patient identifier. The medical picture archive integration system further includes a de-identified image storage system that stores the de-identified medical scan in a second memory that is separate from the first memory, and an annotating system, operable to utilize model parameters received from a central server to perform an inference function on the de-identified medical scan, retrieved from the second memory to generate annotation data for transmission to the medical picture archive system as an annotated DICOM file.

The first memory and the second memory can be implemented by utilizing separate storage systems: the first memory can be implemented by a first storage system designated for PHI storage, and the second memory can be implemented by a second storage system designated for storage of de-identified data. The first storage system can be protected from access by the annotating system, while the second storage system can be accessible by the annotating system. The medical picture archive integration system 2600 can be operable to perform the de-identification function on data in first storage system to generate de-identified data. The de-identified data can then be stored in the second storage system for access by the annotating system. The first and second storage systems can be physically separate, each utilizing at least one of their own, separate memory devices. Alternatively, the first and second storage systems can be virtually separate, where data is stored in separate virtual memory locations on the same set of memory devices. Firewalls, virtual machines, and/or other protected containerization can be utilized to enforce the separation of data in each storage system, to protect the first storage system from access by the annotating system and/or from other unauthorized access, and/or to ensure that only data of the first storage system that has been properly de-identified through application of the de-identification function can be stored in the second storage system.

Figure 8A:
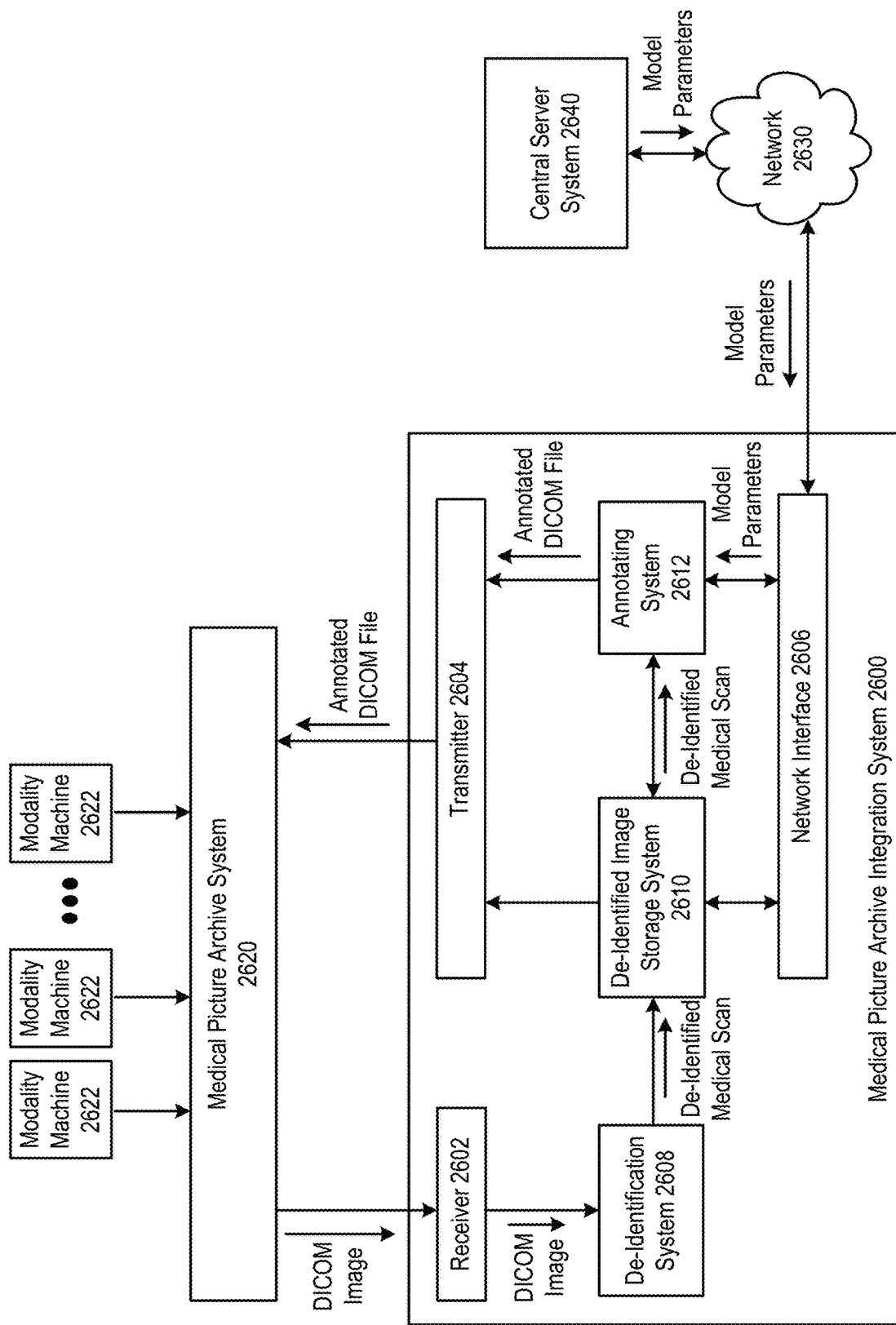
FIGS. 8A-8F are schematic block diagrams of a medical picture archive integration system in accordance with various embodiments.

As shown in FIG. 8A, the medical picture archive system 2620 can receive image data from a plurality of modality machines 2622, such as CT machines, MRI machines, x-ray machines, and/or other medical imaging machines that produce medical scans. The medical picture archive system 2620 can store this image data in a DICOM image format and/or can store the image data in a plurality of medical scan entries 352 as described in conjunction with some or all of the attributes described in conjunction with FIGS. 4A and 4B. While "DICOM image" will be used herein to refer to medical scans stored by the medical picture archive system 2620, the medical picture archive integration system 2600 can provide integration support for medical picture archive systems 2620 that store medical scans in other formats.

The medical picture archive integration system 2600 can include a receiver 2602 and a transmitter 2604, operable to transmit and receive data from the medical picture archive system 2620, respectively. For example, the receiver 2602 and transmitter 2604 can be configured to receive and transmit data, respectively, in accordance with a DICOM communication protocol and/or another communication protocol recognized by the medical image archive system 2620. The receiver can receive DICOM images from the medical picture archive system 2620. The transmitter 2604 can send annotated DICOM files to the medical picture archive system 2620.

DICOM images received via receiver 2602 can be sent directly to a de-identification system 2608. The de-identification system 2608 can be operable to perform a de-identification function on the first DICOM image to identify at least one patient identifier in the DICOM image, and to generate a de-identified medical scan that does not include the identified at least one patient identifier. As used herein, a patient identifier can include any patient identifying data in the image data, header, and/or metadata of a medical scan, such as a patient ID number or other unique patient identifier, an accession number, a service-object pair (SOP) instance unique identifier (UID) field, scan date and/or time that can be used to determine the identity of the patient that was scanned at that date and/or time, and/or other private data corresponding to the patient, doctor, or hospital. In some embodiments, the de-identified medical scan is still in a DICOM image format. For example, a duplicate DICOM image that does not include the patient identifiers can be generated, and/or the original DICOM image can be altered such that the patient identifiers of the new DICOM image are masked, obfuscated, removed, replaced with a custom fiducial, and/or otherwise anonymized. In other embodiments, the de-identified medical scan is formatted in accordance with a different image format and/or different data format that does not include the identifying information. In some embodiments, other private information, for example, associated with a particular doctor or other medical professional, can be identified and anonymized as well.

Some patient identifying information can be included in a DICOM header of the DICOM image, for example, in designated fields for patient identifiers. These corresponding fields can be anonymized within the corresponding DICOM header field. Other patient identifying information can be included in the image itself, such as in medical scan image data 410. For example, the image data can include a patient name or other identifier that was handwritten on a hard copy of the image before the image was digitized. As another example, a hospital administered armband or other visual patient information in the vicinity of the patient may have been captured in the image itself. A computer vision model can detect the presence of these identifiers for anonymization, for example, where a new DICOM image includes a fiducial image that covers the identifying portion of the original DICOM image. In some embodiments, patient information identified in the DICOM header can be utilized to detect corresponding patient information in the image itself. For example, a patient name extracted from the DICOM header before anonymization can be used to search for the patient name in the image and/or to detect a location of the image that includes the patient name. In some embodiments, the de-identification system 2608 is implemented by the de-identification system discussed in conjunction with FIGS. 10A, 10B and 11, and/or utilizes functions and/or operations discussed in conjunction with FIGS. 10A, 10B and 11.

The de-identified medical scan can be stored in de-identified image storage system 2610 and the annotating system 2612 can access the de-identified medical scan from the de-identified image storage system 2610 for processing. The de-identified storage system can archive a plurality of de-identified DICOM images and/or can serve as temporary storage for the de-identified medical scan until processing of the de-identified medical scan by the annotating system 2612 is complete. The annotating system 2612 can generate annotation data by performing an inference function on the de-identified medical scan, utilizing the model parameters received from the central server system 2640. The annotation data can correspond to some or all of the diagnosis data 440 as discussed in conjunction with FIGS. 4A and 4B. In come embodiments, the annotating system 2612 can utilize the model parameters to perform inference step 1354, the detection step 1372, the abnormality classification step 1374, the similar scan identification step 1376, and/or the display parameter step 1378 of the medical scan image analysis system 112, as discussed in conjunction with FIG. 7B, on de-identified medical scans received from the medical picture archive system 2620.

In some embodiments, model parameters for a plurality of inference functions can be received from the central server system 2640, for example, where each inference function corresponds to one of a set of different scan categories. Each scan category can correspond to a unique combination of one or a plurality of scan modalities, one of a plurality of anatomical regions, and/or other scan classifier data 420. For example, a first inference function can be trained on and intended for de-identified medical scans corresponding chest CT scans, and a second inference function can be trained on and intended for de-identified medical scans corresponding to head MRI scans. The annotating system can select one of the set of inference functions based on determining the scan category of the DICOM image, indicated in the de-identified medical scan, and selecting the inference function that corresponds to the determined scan category.

To ensure that scans received from the medical picture archive system 2620 match the set of scan categories for which the annotating system is operable to perform a corresponding inference function, the transmitter can transmit requests, such as DICOM queries, indicating image type parameters such as parameters corresponding to scan classifier data 420, for example indicating one or more scan modalities, one or more anatomical regions, and/or other parameters. For example, the request can indicate that all incoming scans that match the set of scan categories corresponding to a set of inference functions the annotating system 2612 for which the annotating system has obtained model parameters from the central server system 2640 and is operable to perform.

Once the annotation data is generated by performing the selected inference function, the annotating system 2612 can generate an annotated DICOM file for transmission to the medical image archive system 2620 for storage. The annotated DICOM file can include some or all of the fields of the diagnosis data 440 and/or abnormality annotation data 442 of FIGS. 4A and 4B. The annotated DICOM file can include scan overlay data, providing location data of an identified abnormality and/or display data that can be used in conjunction with the original DICOM image to indicate the abnormality visually in the DICOM image and/or to otherwise visually present the annotation data, for example, for use with the medical scan assisted review system 102. For example, a DICOM presentation state file can be generated to indicate the location of an abnormality identified in the de-identified medical scan. The DICOM presentation state file can include an identifier of the original DICOM image, for example, in metadata of the DICOM presentation state file, to link the annotation data to the original DICOM image. In other embodiments, a full, duplicate DICOM image is generated that includes the annotation data with an identifier linking this duplicate annotated DICOM image to the original DICOM image.

The identifier linking the annotated DICOM file to the original DICOM image can be extracted from the original DICOM file by the de-identification system 2608, thus enabling the medical picture archive system 2620 to link the annotated DICOM file to the original DICOM image in its storage. For example, the de-identified medical scan can include an identifier that links the de-identified medical scan to the original DICOM file, but does not link the de-identified medical scan to a patient identifier or other private data.

In some embodiments, generating the annotated DICOM file includes altering one or more fields of the original DICOM header. For example, standardized header formatting function parameters can be received from the central server system and can be utilized by the annotating system to alter the original DICOM header to match a standardized DICOM header format. The standardized header formatting function can be trained in a similar fashion to other medical scan analysis functions discussed herein and/or can be characterized by some or all fields of a medical scan analysis function entry 356. The annotating system can perform the standardized header formatting function on a de-identified medical scan to generate a new, standardized DICOM header for the medical scan to be sent back to the medical picture archive system 2620 in the annotated DICOM file and/or to replace the header of the original DICOM file. The standardized header formatting function can be run in addition to other inference functions utilized to generate annotation data. In other embodiments, the medical picture archive integration system 2600 is implemented primarily for header standardization for medical scans stored by the medical picture archive system 2620. In such embodiments, only the standardized header formatting function is performed on the de-identified data to generate a modified DICOM header for the original DICOM image, but the de-identified medical scan is not annotated.

In some embodiments of header standardization, the annotation system can store a set of acceptable, standardized entries for some or all of the DICOM header fields, and can select one of the set of acceptable, standardized entries in populating one or more fields of the new DICOM header for the annotated DICOM file. For example, each of the set of scan categories determined by the annotating system can correspond to a standardized entry of one or more fields of the DICOM header. The new DICOM header can thus be populated based on the determined scan category.

In some embodiments, each of the set of standardized entries can be mapped to a set of related, non-standardized entries, such as entries in a different order, commonly misspelled entries, or other similar entries that do not follow a standardized format. For example, one of the set of acceptable, standardized entries for a field corresponding to a scan category can include "Chest CT", which can be mapped to a set of similar, non-standardized entries which can include "CT chest", "computerized topography CT", and/or other entries that are not standardized. In such embodiments, the annotating system can determine the original DICOM header is one of the similar non-standardized entries, and can select the mapped, standardized entry as the entry for the modified DICOM header. In other embodiments, the image data itself and/or or other header data can be utilized by the annotation system to determine a standardized field. For example, an input quality assurance function 1106 can be trained by the central server system and sent to the annotating system to determine one or more appropriate scan classifier fields, or one or more other DICOM header fields, based on the image data or other data of the de-identified medical scan. One or more standardized labels can be assigned to corresponding fields of the modified DICOM header based on the one or more fields determined by the input quality assurance function.

In some embodiments, the DICOM header is modified based on the annotation data generated in performing the inference function. In particular, a DICOM priority header field can be generated and/or modified automatically based on the severity and/or time-sensitivity of the abnormalities detected in performing the inference function. For example, a DICOM priority header field can be changed from a low priority to a high priority in response to annotation data indicating a brain bleed in the de-identified medical scan of a DICOM image corresponding to a head CT scan, and a new DICOM header that includes the high priority DICOM priority header field can be sent back to the medical picture archive system 2620 to replace or otherwise be mapped to the original DICOM image of the head CT scan.

In various embodiments, the medical picture archive system 2620 is disconnected from network 2630, for example, to comply with requirements regarding Protected Health Information (PHI), such as patient identifiers and other private patient information included in the DICOM images and/or otherwise stored by the medical picture archive system 2620. The medical picture archive integration system 2600 can enable processing of DICOM images while still protecting private patient information by first de-identifying DICOM data by utilizing de-identification system 2608. The de-identification system 2608 can utilize designated processors and memory of the medical picture archive integration system, for example, designated for PHI. The de-identification system 2608 can be decoupled from the network 2630 to prevent the DICOM images that still include patient identifiers from being accessed via the network 2630. For example, as shown in FIG. 8A, the de-identification system 2608 is not connected to network interface 2606. Furthermore, only the de-identification system 2608 has access to the original DICOM files received from the medical picture archive system 2620 via receiver 2602. The de-identified image storage system 2610 and annotating system 2612, as they are connected to network 2630 via network interface 2606, only store and have access to the de-identified medical scan produced by the de-identification system 2608.

Figure 8B:
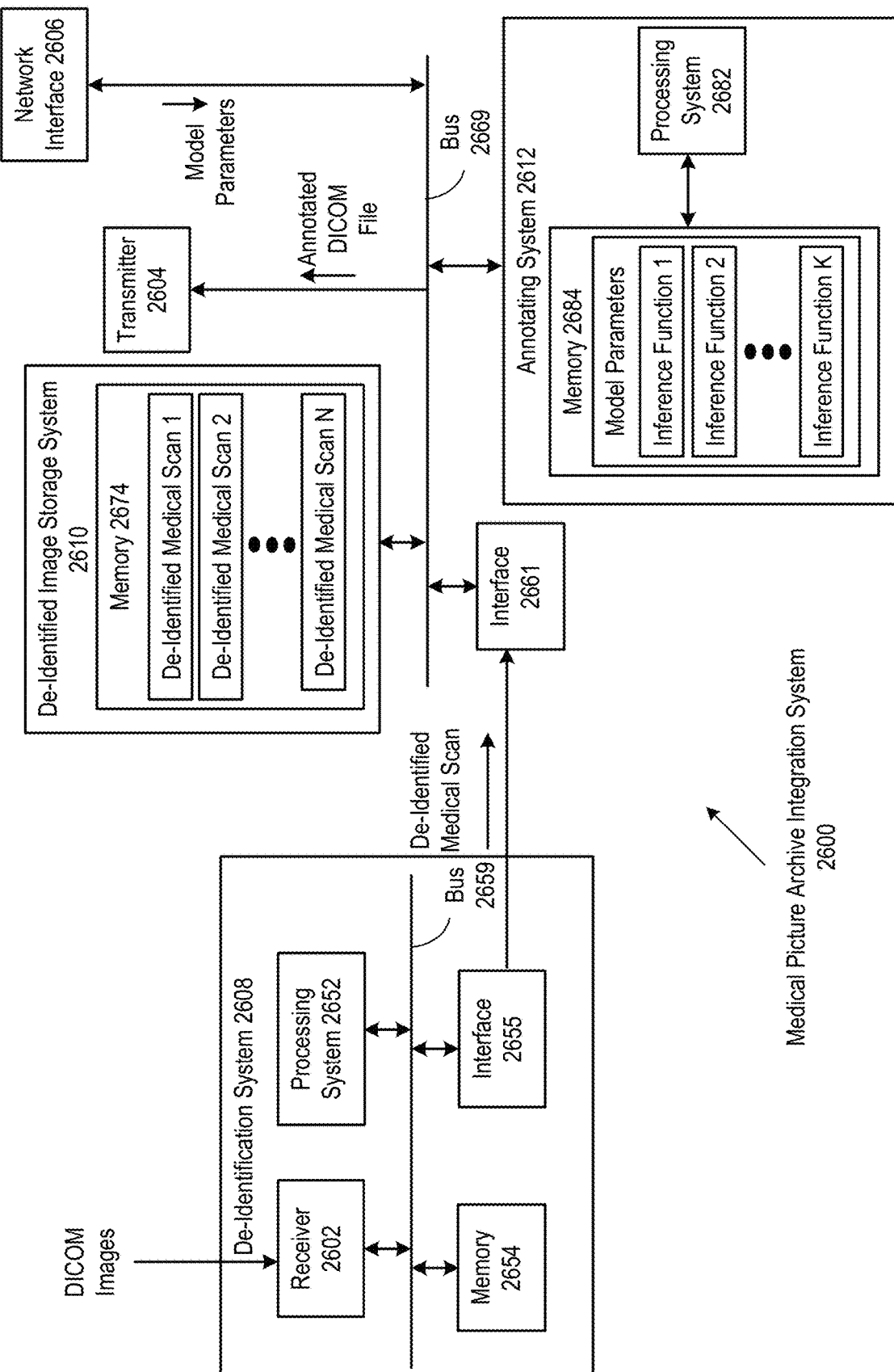

This containerization that separates the de-identification system 2608 from the de-identified image storage system 2610 and the annotating system 2612 is further illustrated in FIG. 8B, which presents an embodiment of the medical picture archive integration system 2600. The de-identification system 2608 can include its own designated memory 2654 and processing system 2652, connected to receiver 2602 via bus 2659. For example, this memory 2654 and processing system 2652 can be designated for PHI, and can adhere to requirements for handling PHI. The memory 2654 can store executable instructions that, when executed by the processing system 2652, enable the de-identification system to perform the de-identification function on DICOM images received via receiver 2602 of the de-identification system. The incoming DICOM images can be temporarily stored in memory 2654 for processing, and patient identifiers detected in performing the de-identification function can be temporarily stored in memory 2654 to undergo anonymization. Interface 2655 can transmit the de-identified medical scan to interface 2661 for use by the de-identified image storage system 2610 and the annotating system 2612. Interface 2655 can be protected from transmitting original DICOM files and can be designated for transmission of de-identified medical scan only.

Bus 2669 connects interface 2661, as well as transmitter 2604 and network interface 2606, to the de-identified image storage system 2610 and the annotating system 2612. The de-identified image storage system 2610 and annotating system 2612 can utilize separate processors and memory, or can utilize shared processors and/or memory. For example, the de-identified image storage system 2610 can serve as temporary memory of the annotating system 2612 as de-identified images are received and processed to generate annotation data.

As depicted in FIG. 8B, the de-identified image storage system 2610 can include memory 2674 that can temporarily store incoming de-identified medical scans as it undergoes processing by the annotating system 2612 and/or can archive a plurality of de-identified medical scans corresponding to a plurality of DICOM images received by the medical picture archive integration system 2600. The annotating system 2612 can include a memory 2684 that stores executable instructions that, when executed by processing system 2682, cause the annotating system 2612 perform a first inference function on de-identified medical scan to generate annotation data by utilizing the model parameters received via interface 2606, and to generate an annotated DICOM file based on the annotation data for transmission via transmitter 2604. The model parameters can be stored in memory 2684, and can include model parameters for a plurality of inference functions, for example, corresponding to a set of different scan categories.

The medical picture archive integration system can be an onsite system, installed at a first geographic site, such as a hospital or other medical entity that is affiliated with the medical picture archive system 2620. The hospital or other medical entity can further be responsible for the PHI of the de-identification system, for example, where the memory 2654 and processing system 2652 are owned by, maintained by, and/or otherwise affiliated with the hospital or other medical entity. The central server system 2640 can be located at a second, separate geographic site that is not affiliated with the hospital or other medical entity and/or at a separate geographic site that is not affiliated with the medical picture archive system 2620. The central server system 2640 can be a server configured to be outside the network firewall and/or out outside the physical security of the hospital or other medical entity or otherwise not covered by the particular administrative, physical and technical safeguards of the hospital or other medical entity.

Figure 8C:
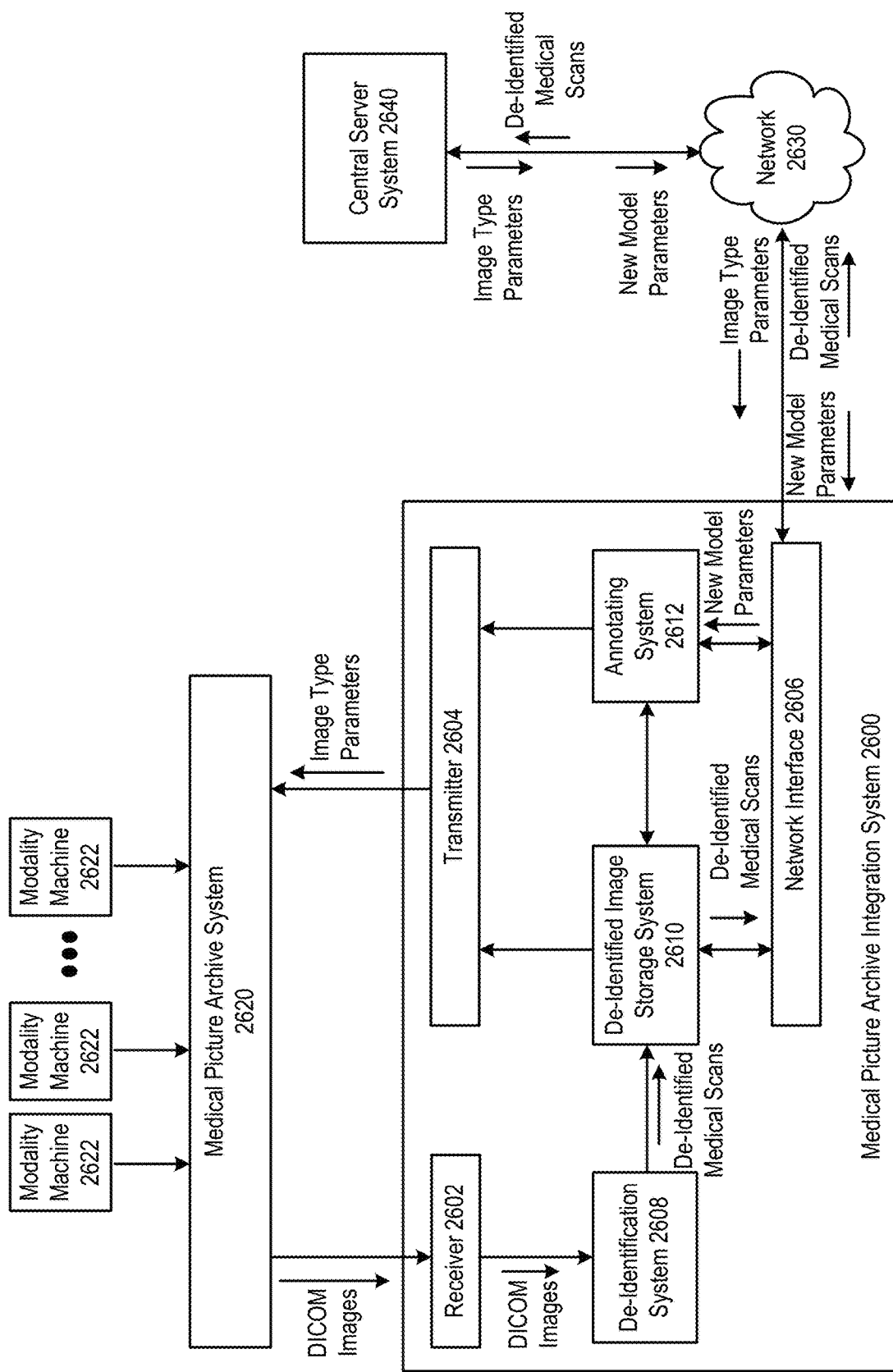

FIG. 8C further illustrates how model parameters can be updated over time to improve existing inference functions and/or to add new inference functions, for example corresponding to new scan categories. In particular, the some or all of the de-identified medical scans generated by the de-identification system 2608 can be transmitted back to the central server system, and the central server system 2640 can train on this data to improve existing models by producing updated model parameters of an existing inference function and/or to generate new models, for example, corresponding to new scan categories, by producing new model parameters for new inference functions. For example, the central server system 2640 can produce updated and/or new model parameters by performing the training step 1352 of the medical scan image analysis system 112, as discussed in conjunction with FIG. 7A, on a plurality of de-identified medical scans received from the medical picture archive integration system 2600.

The image type parameters can be determined by the central server system to dictate characteristics of the set of de-identified medical scans to be received to train and/or retrain the model. For example, the image type parameters can correspond to one or more scan categories, can indicate scan classifier data 420, can indicate one or more scan modalities, one or more anatomical regions, a date range, and/or other parameters. The image type parameters can be determined by the central server system based on training parameters 620 determined for the corresponding inference function to be trained, and/or based on characteristics of a new and/or existing scan category corresponding to the inference function to be trained. The image type parameters can be sent to the medical picture archive integration system 2600, and a request such as a DICOM query can be sent to the medical picture archive system 2620, via transmitter 2604, that indicates the image type parameters. For example, the processing system 2682 can be utilized to generate the DICOM query based on the image type parameters received from the central server system 2640. The medical picture archive system can automatically transmit one or more DICOM images to the medical picture archive integration system in response to determining that the one or more DICOM images compares favorably to the image type parameters. The DICOM images received in response can be de-identified by the de-identification system 2608. In some embodiments, the de-identified medical scans can be transmitted directly to the central server system 2640, for example, without generating annotation data.

The central server system can generate the new and/or updated model parameters by training on the received set of de-identified medical scans, and can transmit the new and/or updated model parameters to the de-identified storage system. If the model parameters correspond to a new inference function for a new scan category, the medical picture archive integration system 2600 can generate a request, such as a DICOM query, for transmission to the medical picture archive system indicating that incoming scans corresponding to image type parameters corresponding to the new scan category be sent to the medical picture archive integration system. The annotating system can update the set of inference functions to include the new inference function, and the annotating system can select the new inference function from the set of inference functions for subsequently generated de-identified medical scans by the de-identification system by determining each of these de-identified medical scans indicate the corresponding DICOM image corresponds to the new scan category. The new model parameters can be utilized to perform the new inference function on each of these de-identified medical scans to generate corresponding annotation data, and an annotated DICOM file corresponding to each of these de-identified medical scans can be generated for transmission to the medical picture archive system via the transmitter.

In some embodiments, the central server system 2640 receives a plurality of de-identified medical scans from a plurality of medical picture archive integration system 2600, for example, each installed at a plurality of different hospitals or other medical entities, via the network 2630. The central server system can generate training sets by integrating de-identified medical scans from some or all of the plurality of medical picture archive integration systems 2600 to train one or more inference functions and generate model parameters. The plurality of medical picture archive integration systems 2600 can utilize the same set of inference functions or different sets of inference functions. In some embodiments, the set of inference functions utilized by the each of the plurality of medical picture archive systems 2620 are trained on different sets of training data. For example, the different sets of training data can correspond to the set of de-identified medical scans received from the corresponding medical picture archive integration system 2600.

In some embodiments, the medical scan diagnosing system 108 can be utilized to implement the annotating system 2612, where the corresponding subsystem processing device 235 and subsystem memory device 245 of the medical scan diagnosing system 108 are utilized to implement the processing system 2682 and the memory 2684, respectively. Rather than receiving the medical scans via the network 150 as discussed in conjunction with FIG. 6A, the medical scan diagnosing system 108 can perform a selected medical scan inference function 1105 on an incoming de-identified medical scan generated by the de-identification system 2608 and/or retrieved from the de-identified image storage system 2610. Memory 2684 can store the set of medical scan inference functions 1105, each corresponding to a scan category 1120, where the inference function is selected from the set based on determining the scan category of the de-identified medical scan and selecting the corresponding inference function. The processing system 2682 can perform the selected inference function 1105 to generate the inference data 1110, which can be further utilized by the annotating system 2612 to generate the annotated DICOM file for transmission back to the medical picture archive system 2620. New medical scan inference functions 1105 can be added to the set when corresponding model parameters are received from the central server system. The remediation step 1140 can be performed locally by the annotating system 2612 and/or can be performed by the central server system 2640 by utilizing one or more de-identified medical scans and corresponding annotation data sent to the central server system 2640. Updated model parameters can be generated by the central server system 2640 and sent to the medical picture archive integration system 2600 as a result of performing the remediation step 1140.

The central server system 2640 can be implemented by utilizing one or more of the medical scan subsystems 101, such as the medical scan image analysis system 112 and/or the medical scan diagnosing system 108, to produce model parameters for one or more inference functions. The central server system can store or otherwise communicate with a medical scan database 342 that includes the de-identified medical scans and/or annotation data received from one or more medical picture archive integration systems 2600. Some or all entries of the medical scan database 342 can be utilized to as training data to produce model parameters for one or more inference functions. These entries of the medical scan database 342 can be utilized by other subsystems 101 as discussed herein. For example, other subsystems 101 can utilize the central server system 2640 to fetch medical scans and/or corresponding annotation data that meet specified criteria. The central server system 2640 can query the medical picture archive integration system 2600 based on this criteria, and can receive de-identified medical scans and/or annotation data in response. This can be sent to the requesting subsystem 101 directly and/or can be added to the medical scan database 342 or another database of the database storage system 140 for access by the requesting subsystem 101.

Alternatively or in addition, the central server system 2640 can store or otherwise communicate with a user database 344 storing user profile entries corresponding to each of a plurality of medical entities that each utilize a corresponding one of a plurality of medical picture archive integration systems 2600. For example, basic user data corresponding to the medical entity can be stored as basic user data, a number of scans or other consumption information indicating usage of one or more inference functions by corresponding medical picture archive integration system can be stored as consumption usage data, and/or a number of scans or other contribution information indicating de-identified scans sent to the central server system as training data can be stored as contribution usage data. The user profile entry can also include inference function data, for example, with a list of model parameters or function identifiers, such as medical scan analysis function identifiers 357, of inference functions currently utilized by the corresponding medical picture archive integration system 2600. These entries of the user database 344 can be utilized by other subsystems 101 as discussed herein.

Alternatively or in addition, the central server system 2640 can store or otherwise communicate with a medical scan analysis function database 346 to store model parameters, training data, or other information for one or more inference functions as medical scan analysis function entries 356. In some embodiments, model parameter data 623 can indicate the model parameters and function classifier data 610 can indicate the scan category of inference function entries. In some embodiments, the medical scan analysis function entry 356 can further include usage identifying information indicating a medical picture archive integration system identifier, medical entity identifier, and/or otherwise indicating which medical archive integration systems and/or medical entities have received the corresponding model parameters to utilize the inference function corresponding to the medical scan analysis function entry 356. These entries of the medical scan analysis function database 346 can be utilized by other subsystems 101 as discussed herein.

In some embodiments, the de-identification function is a medical scan analysis function, for example, with a corresponding medical scan analysis function entry 356 in the medical scan analysis function database 346. In some embodiments, the de-identification function is trained by the central server system 2640. For example, the central server system 2640 can send de-identification function parameters to the medical picture archive integration system 2600 for use by the de-identification system 2608. In embodiments with a plurality of medical picture archive integration systems 2600, each of the plurality of medical picture archive integration systems 2600 can utilize the same or different de-identification functions. In some embodiments, the de-identification function utilized by the each of the plurality of medical picture archive integration systems 2600 are trained on different sets of training data. For example, the different sets of training data can correspond to each different set of de-identified medical scans received from each corresponding medical picture archive integration system 2600.

Figure 8D:
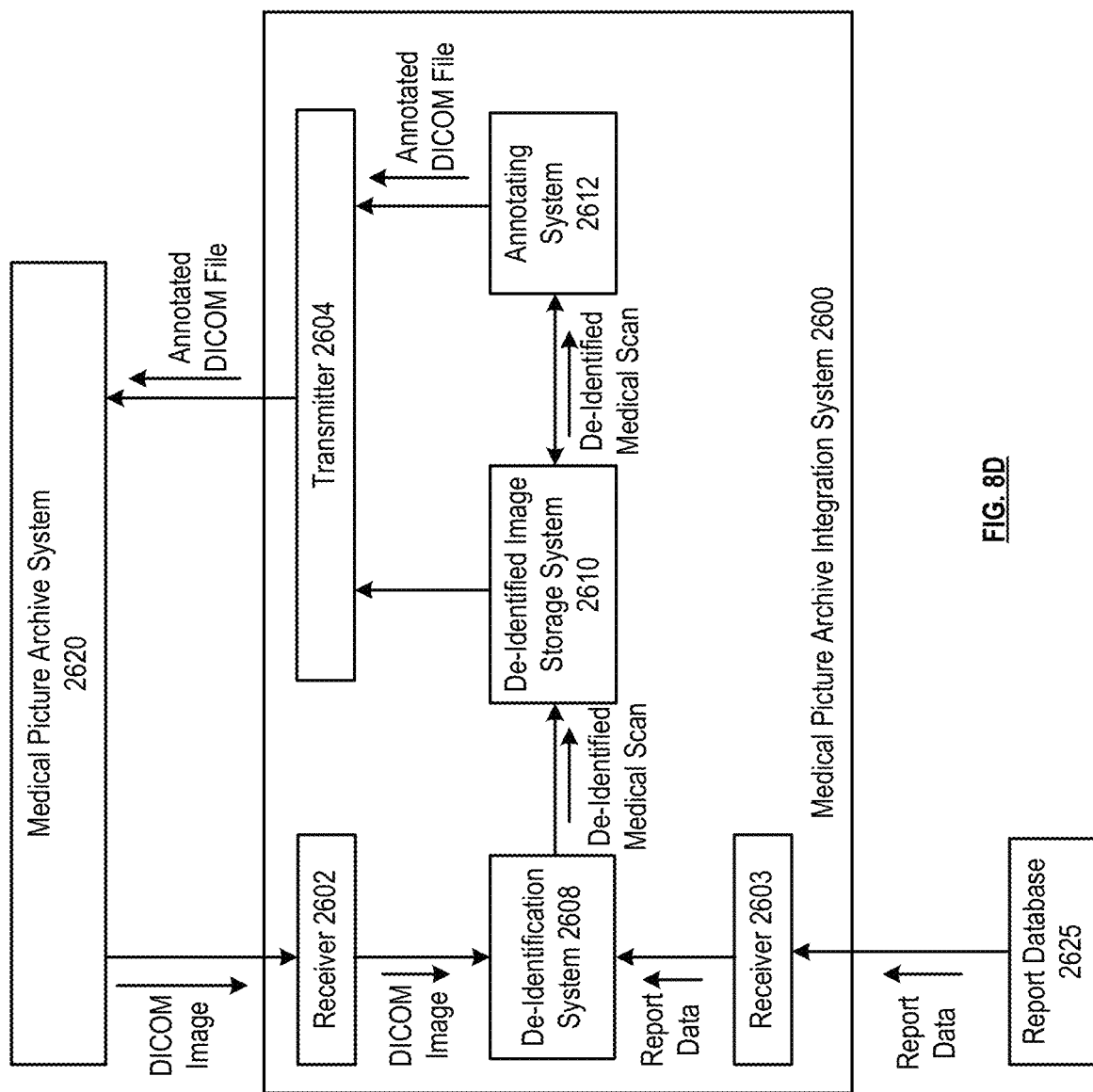
Figure 8E:
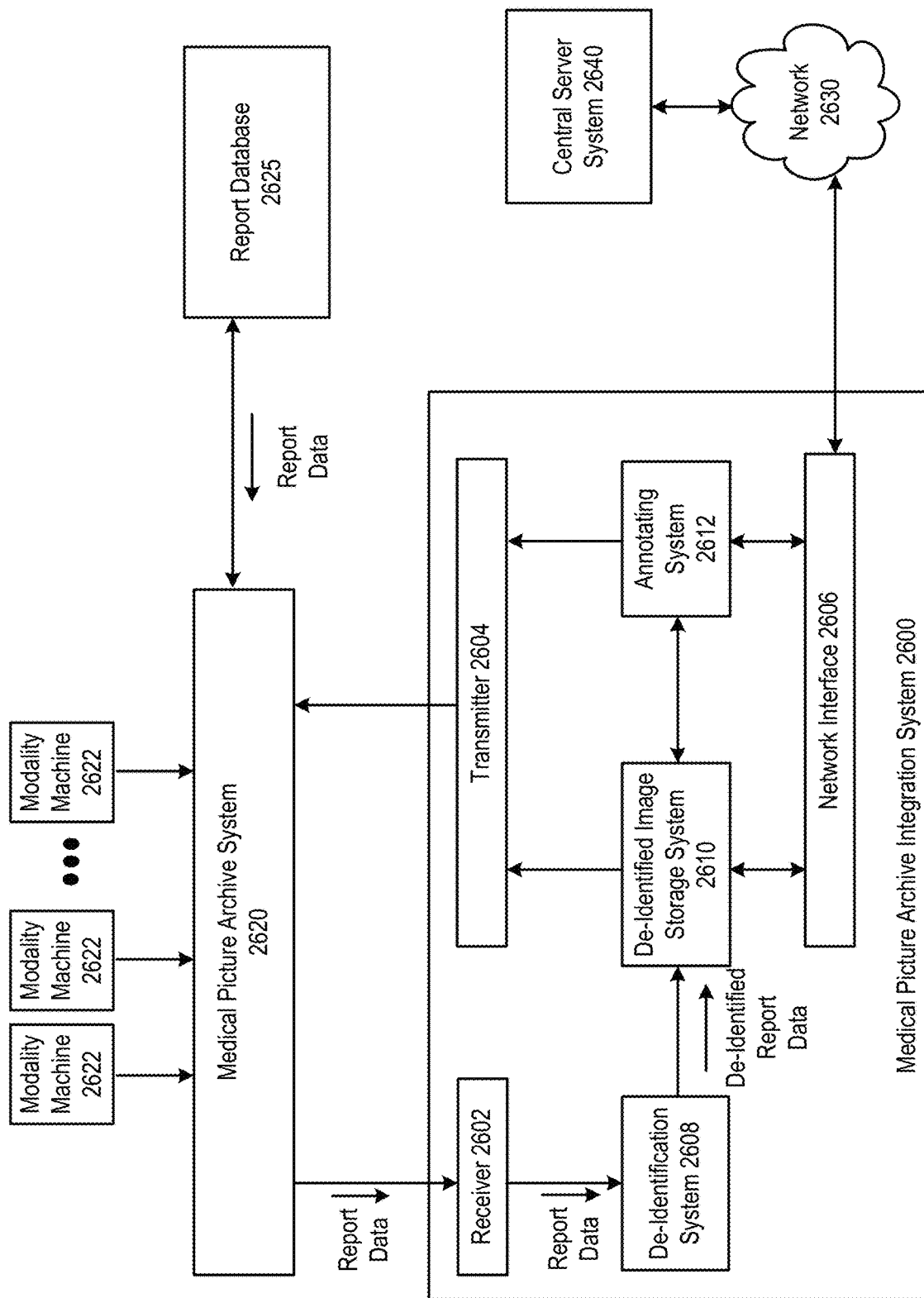
Figure 8F:
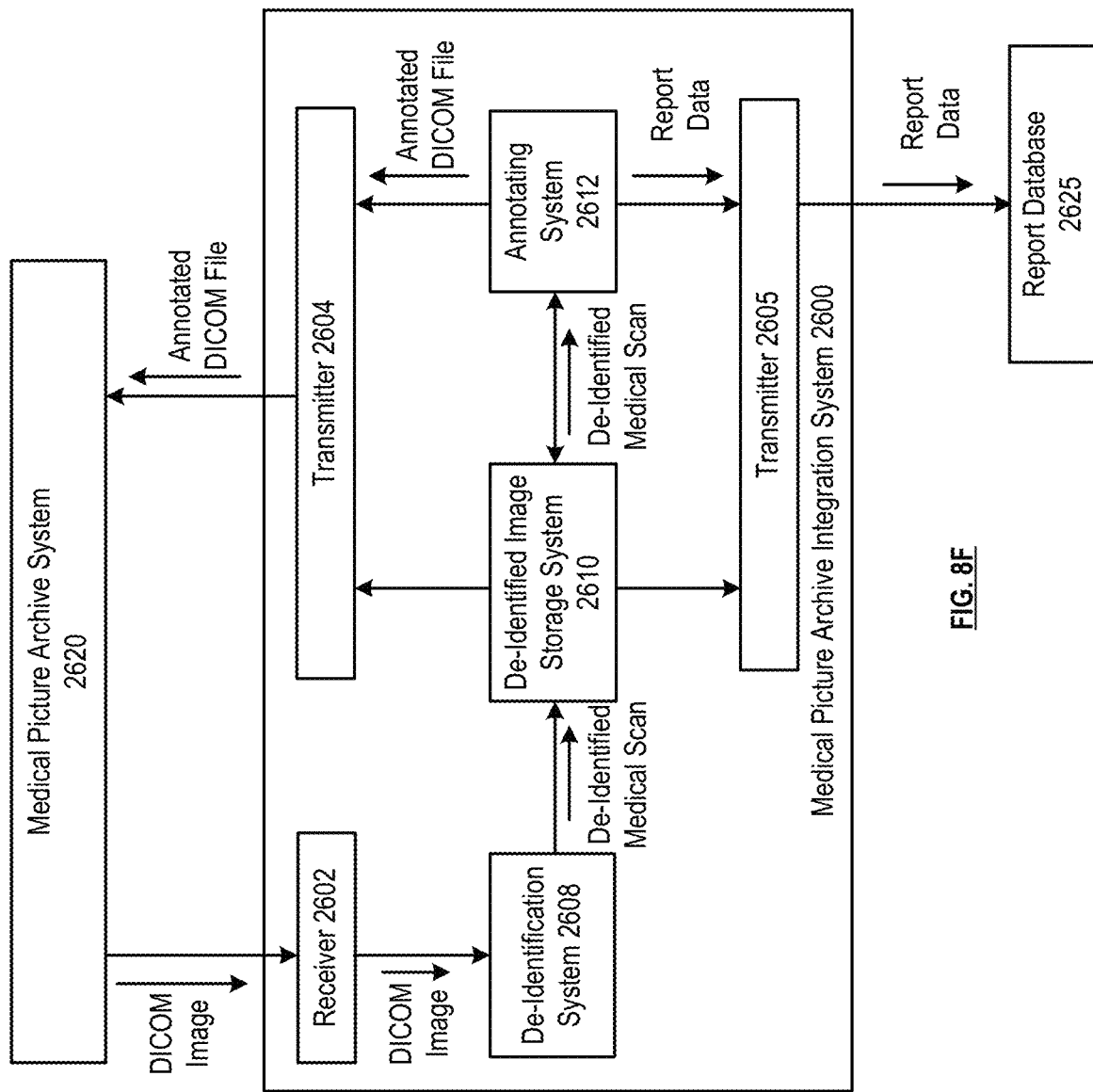

In some embodiments, as illustrated in FIGS. 8D-8F, the medical picture archive integration system 2600 can further communicate with a report database 2625, such as a Radiology Information System (RIS), that includes a plurality of medical reports corresponding to the DICOM images stored by the medical picture archive system 2620.

As shown in FIG. 8D, the medical picture archive integration system 2600 can further include a receiver 2603 that receives report data, corresponding to the DICOM image, from report database 2625. The report database 2625 can be affiliated with the medical picture archive system 2620 and can store report data corresponding to DICOM images stored in the medical picture archive system. The report data of report database 2625 can include PHI, and the report database 2625 can thus be disconnected from network 2630.

The report data can include natural language text, for example, generated by a radiologist that reviewed the corresponding DICOM image. The report data can be used to generate the de-identified medical scan, for example, where the de-identification system 2608 performs a natural language analysis function on the report data to identify patient identifying text in the report data. The de-identification system 2608 can utilize this patient identifying text to detect matching patient identifiers in the DICOM image to identify the patient identifiers of the DICOM image and generate the de-identified medical scan. In some embodiments, the report data can be de-identified by obfuscating, hashing, removing, replacing with a fiducial, or otherwise anonymizing the identified patient identifying text to generate de-identified report data.

The de-identified report data can be utilized by the annotating system 2612, for example, in conjunction with the DICOM image, to generate the annotation data. For example, the annotating system 2612 can perform a natural language analysis function on the de-identified natural language text of the report data to generate some or all of the annotation data. In some embodiments, the de-identified report data is sent to the central server system, for example, to be used as training data for inference functions, for natural language analysis functions, for other medical scan analysis functions, and/or for use by at least one other subsystem 101. For example, other subsystems 101 can utilize the central server system 2640 to fetch medical reports that correspond to particular medical scans or otherwise meet specified criteria. The central server system 2640 can query the medical picture archive integration system 2600 based on this criteria, and can receive de-identified medical reports in response. This can be sent to the requesting subsystem 101 directly, can be added to the medical scan database 342, a de-identified report database, or another database of the database storage system 140 for access by the requesting subsystem 101.

In some embodiments the medical picture archive integration system 2600 can query the report database 2625 for the report data corresponding to a received DICOM image by utilizing a common identifier extracted from the DICOM image.

In some embodiments, the report data can correspond to a plurality of DICOM images. For example, the report data can include natural language text describing a plurality of medical scans of a patient that can include multiple sequences, multiple modalities, and/or multiple medical scans taken over time. In such embodiments, the patient identifying text and/or annotation data detected in the report data can also be applied to de-identify and/or generate annotation data for the plurality of DICOM images it describes. In such embodiments, the medical picture archive integration system 2600 can query the medical picture archive system 2620 for one or more additional DICOM images corresponding to the report data, and de-identified data and annotation data for these additional DICOM images can be generated accordingly by utilizing the report data.

In some embodiments, as shown in FIG. 8E, the medical picture archive system 2620 communicates with the report database 2625. The medical picture archive system 2620 can request the report data corresponding to the DICOM image from the report database 2625, and can transmit the report data to the medical picture archive integration system 2600 via a DICOM communication protocol for receipt via receiver 2602. The medical picture archive system 2620 can query the report database 2625 for the report data, utilizing a common identifier extracted from the corresponding DICOM image, in response to determining to send the corresponding DICOM image to the medical picture archive integration system 2600.

FIG. 8F presents an embodiment where report data is generated by the annotating system 2612 and is transmitted, via a transmitter 2605, to the report database 2625, for example via a DICOM communication protocol or other protocol recognized by the report database 2625. In other embodiments, the report data is instead transmitted via transmitter 2604 to the medical picture archive system 2620, and the medical picture archive system 2620 transmits the report data to the report database 2625.

The report data can be generated by the annotating system 2612 as output of performing the inference function on the de-identified medical scan. The report data can include natural language text data 448 generated automatically based on other diagnosis data 440 such as abnormality annotation data 442 determined by performing the inference function, for example, by utilizing a medical scan natural language generating function trained by the medical scan natural language analysis system 114. The report data can be generated instead of, or in addition to, the annotated DICOM file.

Figure 9:
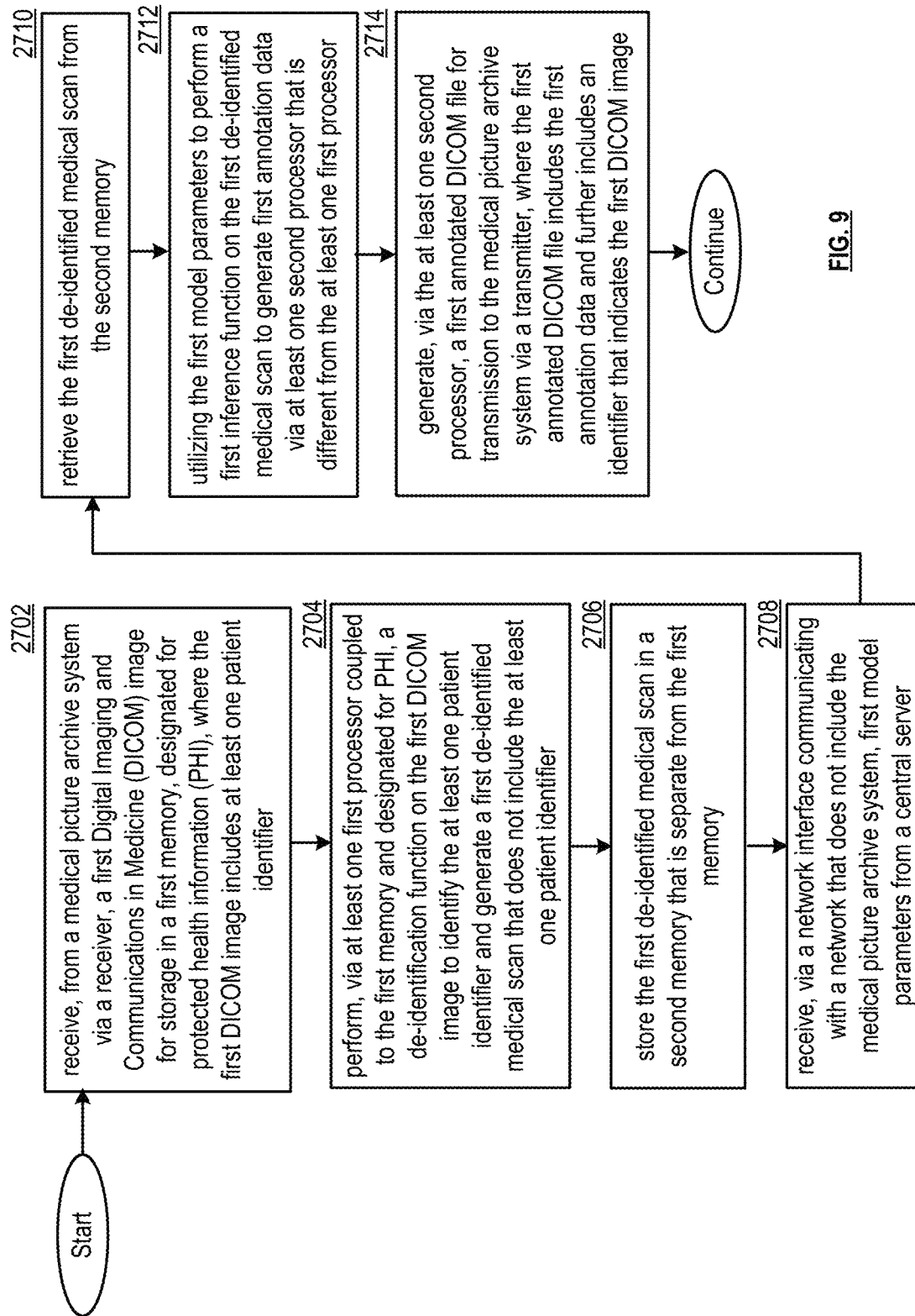
FIG. 9 is a flowchart representation of a method for execution by a medical picture archive integration system in accordance with various embodiments.

FIG. 9 presents a flowchart illustrating a method for execution by a medical picture archive integration system 2600 that includes a first memory and a second memory that store executional instructions that, when executed by at least one first processor and at least one second processor, respectfully, cause the medical picture archive integration system to perform the steps below. In various embodiments, the first memory and at least one first processor are implemented by utilizing, respectfully, the memory 2654 and processing system 2652 of FIG. 8B. In various embodiments, the second memory is implemented by utilizing the memory 2674 and/or the memory 2684 of FIG. 8B. In various embodiments, the at least one second processor is implemented by utilizing the processing system 2682 of FIG. 8B.

Step 2702 includes receiving, from a medical picture archive system via a receiver, a first DICOM image for storage in the first memory, designated for PHI, where the first DICOM image includes at least one patient identifier. Step 2704 includes performing, via at least one first processor coupled to the first memory and designated for PHI, a de-identification function on the first DICOM image to identify the at least one patient identifier and generate a first de-identified medical scan that does not include the at least one patient identifier.

Step 2706 includes storing the first de-identified medical scan in a second memory that is separate from the first memory. Step 2708 includes receiving, via a network interface communicating with a network that does not include the medical picture archive system, first model parameters from a central server.

Step 2710 includes retrieving the first de-identified medical scan from the second memory. Step 2712 includes utilizing the first model parameters to perform a first inference function on the first de-identified medical scan to generate first annotation data via at least one second processor that is different from the at least one first processor. Step 2714 includes generating, via the at least one second processor, a first annotated DICOM file for transmission to the medical picture archive system via a transmitter, where the first annotated DICOM file includes the first annotation data and further includes an identifier that indicates the first DICOM image. In various embodiments, the first annotated DICOM file is a DICOM presentation state file.

In various embodiments, the second memory further includes operational instructions that, when executed by the at least one second processor, further cause the medical picture archive integration system to retrieve a second de-identified medical scan from the de-identified image storage system, where the second de-identified medical scan was generated by the at least one first processor by performing the de-identification function on a second DICOM image received from the medical picture archive system. The updated model parameters are utilized to perform the first inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the second memory stores a plurality of de-identified medical scans generated by the at least one first processor by performing the de-identification function on a corresponding plurality of DICOM images received from the medical picture archive system via the receiver. The plurality of de-identified medical scans is transmitted to the central server via the network interface, and the central server generates the first model parameters by performing a training function on training data that includes the plurality of de-identified medical scans.

In various embodiments, the central server generates the first model parameters by performing a training function on training data that includes a plurality of de-identified medical scans received from a plurality of medical picture archive integration systems via the network. Each of the plurality of medical picture archive integration systems communicates bidirectionally with a corresponding one of a plurality of medical picture archive systems, and the plurality of de-identified medical scans corresponds to a plurality of DICOM images stored by the plurality of medical picture archive integration systems.

In various embodiments, the first de-identified medical scan indicates a scan category of the first DICOM image. The second memory further stores operational instructions that, when executed by the at least one second processor, further cause the medical picture archive integration system to select the first inference function from a set of inference functions based on the scan category. The set of inference functions corresponds to a set of unique scan categories that includes the scan category. In various embodiments, each unique scan category of the set of unique scan categories is characterized by one of a plurality of modalities and one of a plurality of anatomical regions.

In various embodiments, the first memory further stores operational instructions that, when executed by the at least one first processor, further cause the medical picture archive integration system to receive a plurality of DICOM image data from the medical picture archive system via the receiver for storage in the first memory in response to a query transmitted to the medical picture archive system via the transmitter. The query is generated by the medical picture archive integration system in response to a request indicating a new scan category received from the central server via the network. The new scan category is not included in the set of unique scan categories, and the plurality of DICOM image data corresponds to the new scan category. The de-identification function is performed on the plurality of DICOM image data to generate a plurality of de-identified medical scans for transmission to the central server via the network.

The second memory further stores operational instructions that, when executed by the at least one second processor, further cause the medical picture archive integration system to receive second model parameters from the central server via the network for a new inference function corresponding to the new scan category. The set of inference functions is updated to include the new inference function. The second de-identified medical scan is retrieved from the first memory, where the second de-identified medical scan was generated by the at least one first processor by performing the de-identification function on a second DICOM image received from the medical picture archive system. The new inference function is selected from the set of inference functions by determining the second de-identified medical scan indicates the second DICOM image corresponds to the new scan category. The second model parameters are utilized to perform the new inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the medical picture archive integration system generates parameter data for transmission to the medical picture archive system that indicates the set of unique scan categories. The medical picture archive system automatically transmits the first DICOM image to the medical picture archive integration system in response to determining that the first DICOM image compares favorably to one of the set of unique scan categories.

In various embodiments, the second memory further stores operational instructions that, when executed by the at least one second processor, cause the medical picture archive integration system to generate a natural language report data is based on the first annotation data and to transmit, via a second transmitter, the natural language report data to a report database associated with the medical picture archive integration system, where the natural language report data includes an identifier corresponding to the first DICOM image.

In various embodiments, the first memory further stores operational instructions that, when executed by the at least one first processor, cause the medical picture archive integration system to receive, via a second receiver, a natural language report corresponding to the first DICOM image from the report database. A set of patient identifying text included in the natural language report are identified. Performing the de-identification function on the first DICOM image includes searching the first DICOM image for the set of patient identifying text to identify the at least one patient identifier.

In various embodiments, the first memory is managed by a medical entity associated with the medical picture archive system. The medical picture archive integration system is located at a first geographic site corresponding to the medical entity, and the central server is located at a second geographic site. In various embodiments, the first memory is decoupled from the network to prevent the first DICOM image that includes the at least one patient identifier from being communicated via the network. In various embodiments, the medical picture archive system is a Picture Archive and Communication System (PACS) server, and the first DICOM image is received in response to a query sent to the medical picture archive system by the transmitter in accordance with a DICOM communication protocol.

Figure 10A:
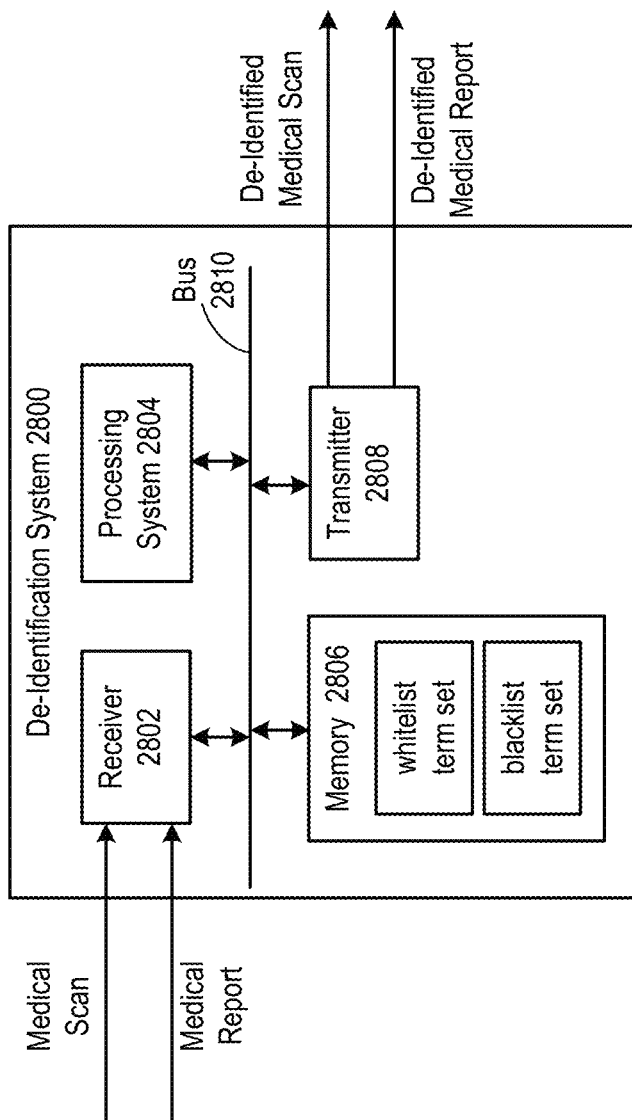
FIG. 10A is a schematic block diagram of a de-identification system in accordance with various embodiments.

FIG. 10A presents an embodiment of a de-identification system 2800. The de-identification system 2800 can be utilized to implement the de-identification system 2608 of FIGS. 8A-8F. In some embodiments, the de-identification system 2800 can be utilized by other subsystems to de-identify image data, medical report data, private fields of medical scan entries 352 such as patient identifier data 431, and/or other private fields stored in databases of the database memory device 340.

The de-identification system can be operable to receive, from at least one first entity, a medical scan and a medical report corresponding to the medical scan. A set of patient identifiers can be identified in a subset of fields of a header of the medical scan. A header anonymization function can be performed on each of the set of patient identifiers to generate a corresponding set of anonymized fields. A de-identified medical scan can be generated by replacing the subset of fields of the header of the medical scan with the corresponding set of anonymized fields.

A subset of patient identifiers of the set of patient identifiers can be identified in the medical report by searching text of the medical report for the set of patient identifiers. A text anonymization function can be performed on the subset of patient identifiers to generate corresponding anonymized placeholder text for each of the subset of patient identifiers. A de-identified medical report can be generated by replacing each of the subset of patient identifiers with the corresponding anonymized placeholder text. The de-identified medical scan and the de-identified medical report can be transmitted to a second entity via a network.

As shown in FIG. 10A, the de-identification system 2800 can include at least one receiver 2802 operable to receive medical scans, such as medical scans in a DICOM image format. The at least one receiver 2802 is further operable to receive medical reports, such as report data 449 or other reports containing natural language text diagnosing, describing, or otherwise associated the medical scans received by the de-identification system. The medical scans and report data can be received from the same or different entity, and can be received by the same or different receiver 2802 in accordance with the same or different communication protocol. For example, the medical scans can be received from the medical picture archive system 2620 of FIGS. 8A-8F and the report data can be received from the report database 2625 of FIGS. 8D-8F. In such embodiments, the receiver 2802 can be utilized to implement the receiver 2602 of FIG. 8B.

The de-identification system 2800 can further include a processing system 2804 that includes at least one processor, and a memory 2806. The memory 2806 can store operational instructions that, when executed by the processing system, cause the de-identification system to perform at least one patient identifier detection function on the received medical scan and/or the medical report to identify a set of patient identifiers in the medical scan and/or the medical report. The operational instructions, when executed by the processing system, can further cause the de-identification system to perform an anonymization function on the medical scan and/or the medical report to generate a de-identified medical scan and/or a de-identified medical report that do not include the set of patient identifiers found in performing the at least one patient identifier detection function. Generating the de-identified medical scan can include generating a de-identified header and generating de-identified image data, where the de-identified medical scan includes both the de-identified header and the de-identified image data. The memory 2806 can be isolated from Internet connectivity, and can be designated for PHI.

The de-identification system 2800 can further include at least one transmitter 2808, operable to transmit the de-identified medical scan and de-identified medical report. The de-identified medical scan and de-identified medical report can be transmitted back to the same entity from which they were received, respectively, and/or can be transmitted to a separate entity. For example, the at least one transmitter can transmit the de-identified medical scan to the de-identified image storage system 2610 of FIGS. 8A-8F and/or can transmit the de-identified medical scan to central server system 2640 via network 2630 of FIGS. 8A-8F. In such embodiments, the transmitter 2808 can be utilized to implement the interface 2655 of FIG. 8B. The receiver 2802, processing system 2804, memory 2806, and/or transmitter 2808 can be connected via bus 2810.

Some or all of the at least one patient identifier detection function and/or at least one anonymization function as discussed herein can be trained and/or implemented by one or subsystems 101 in the same fashion as other medical scan analysis functions discussed herein, can be stored in medical scan analysis function database 346 of FIG. 3, and/or can otherwise be characterized by some or all fields of a medical scan analysis function entry 356 of FIG. 5.

The de-identification system 2800 can perform separate patient identifier detection functions on the header of a medical report and/or medical scan, on the text data of the medical report, and/or on the image data of the medical scan, such as text extracted from the image data of the medical scan. Performance of each of these functions generates an output of its own set of identified patient identifiers. Combining these sets of patient identifiers yields a blacklist term set. A second pass of the header of a medical report and/or medical scan, on the text data of the medical report, and/or on the image data of the medical scan that utilizes this blacklist term set can catch any terms that were missed by the respective patient identifier detection function, and thus, the outputs of these multiple identification processes can support each other. For example, some of the data in the headers will be in a structured form and can thus be easier to reliably identify. This can be exploited and used to further anonymize these identifiers when they appear in free text header fields, report data, and/or in the image data of the medical scan. Meanwhile, unstructured text in free text header fields, report data, and/or image data of the medical scan likely includes pertinent clinical information to be preserved in the anonymization process, for example, so it can be leveraged by at least one subsystems 101 and/or so it can be leveraged in training at least one medical scan analysis function.

At least one first patient identifier detection function can include extracting the data in a subset of fields of a DICOM header, or another header or other metadata of the medical scan and/or medical report with a known type that corresponds to patient identifying data. For example, this patient identifying subset of fields can include a name field, a patient ID number field or other unique patient identifier field, a date field, a time field, an age field, an accession number field, SOP instance UID, and/or other fields that could be utilized to identify the patient and/or contain private information. A non-identifying subset of fields of the header can include hospital identifiers, machine model identifiers, and/or some or all fields of medical scan entry 352 that do not correspond to patient identifying data. The patient identifying subset of fields and the non-identifying subset of fields can be mutually exclusive and collectively exhaustive with respect to the header. The at least one patient identifier function can include generating a first set of patient identifiers by ignoring the non-identifying subset of fields and extracting the entries of the patient identifying subset of fields only. This first set of patient identifiers can be anonymized to generate a de-identified header as discussed herein.

In some embodiments, at least one second patient identifier detection function can be performed on the report data of the medical report. The at least one second patient identifier detection function can include identifying patient identifying text in the report data by performing a natural language analysis function, for example, trained by the medical scan natural language analysis system 114. For example, the at least one second patient identifier detection function can leverage the known structure of the medical report and/or context of the medical report. A second set of patient identifiers corresponding to the patient identifying text can be determined, and the second set of patient identifiers can be anonymized to generate a de-identified medical report. In some embodiments, a de-identified medical report includes clinical information, for example, because the portion of the original medical report that includes the clinical information was deemed to be free of patient identifying text and/or because the portion of the original medical report that includes the clinical information was determined to include pertinent information to be preserved.

In some embodiments, the medical report includes image data corresponding to freehand or typed text. For example the medical report can correspond to a digitized scan of original freehand text written by a radiologist or other medical professional. In such embodiments, the patient identifier detection function can first extract the text from the freehand text in the image data to generate text data before the at least one second patient identifier detection function is performed on the text of the medical report to generate the second set of patient identifiers.

In some embodiments, the at least one second patient identifier detection function can similarly be utilized to identify patient identifying text in free text fields and/or unstructured text fields of a DICOM header and/or other metadata of the medical scan and/or medical report data by performing a natural language analysis function, for example, trained by the medical scan natural language analysis system 114. A third set of patient identifiers corresponding to this patient identifying text of the free text and/or unstructured header fields can be determined, and the third set of patient identifiers can be anonymized to generate de-identified free text header field and/or unstructured header fields. In some embodiments, a de-identified free text header field and/or unstructured header field includes clinical information, for example, because the portion of the original corresponding header field that includes the clinical information was deemed to be free of patient identifying text and/or because the portion of the original corresponding header field that includes the clinical information was determined to include pertinent information to be preserved.

Patient identifiers can also be included in the image data of the medical scan itself. For example, freehand text corresponding to a patient name written on a hard copy of the medical scan before digitizing can be included in the image data, as discussed in conjunction with FIG. 10B. Other patient identifiers, such as information included on a patient wristband or other identifying information located on or within the vicinity of the patient may have been captured when the medical scan was taken, and can thus be included in the image. At least one third patient identifier detection function can include extracting text from the image data and/or detecting non-text identifiers in the image data by performing a medical scan image analysis function, for example, trained by the medical scan image analysis system 112. For example, detected text that corresponds to an image location known to include patient identifiers, detected text that corresponds to a format of a patient identifier, and/or or detected text or other image data determined to correspond to a patient identifier can be identified. The at least one third patient identifier detection function can further include identifying patient identifying text in the text extracted from the image data by performing the at least one second patient identifier detection function and/or by performing a natural language analysis function. A fourth set of patient identifiers corresponding to patient identifying text or other patient identifiers detected in the image data of the medical scan can be determined, and the fourth set of patient identifiers can be anonymized in the image data to generate de-identified image data of the medical scan as described herein. In particular, the fourth set of patient identifiers can be detected in a set of regions of image data of the medical scan, and the set of regions of the image data can be anonymized.

In some embodiments, only a subset of the patient identifier detection functions described herein are performed to generate respective sets of patient identifiers for anonymization. In some embodiments, additional patient identifier detection functions can be performed on the medical scan and/or medical report to determine additional respective sets of patient identifiers for anonymization. The sets of patient identifiers outputted by performing each patient identifier detection function can have a null or non-null intersection. The sets of patient identifiers outputted by performing each patient identifier function can have null or non-null set differences.

Cases where the sets of patient identifiers have non-null set differences can indicate that a patient identifier detected by one function may have been missed by another function. The combined set of patient identifiers, for example, generated as the union of the sets of sets of patient identifiers outputted by performing each patient identifier function, can be used to build a blacklist term set, for example, stored in memory 2806. The blacklist term set can designate the final set of terms to be anonymized. A second pass of header data, medical scans, medical reports, and/or any free text extracted from the header data, the medical scan, and/or the medical report can be performed by utilizing the blacklist term set to flag terms for anonymization that were not caught in performing the respective at least one patient identifier detection function. For example, performing the second pass can include identifying at least one patient identifier of the blacklist term set in the header, medical report, and/or image data of the medical scan. This can include by searching corresponding extracted text of the header, medical report, and/or image data for terms included in blacklist term set and/or by determining if each term in the extracted text is included in the blacklist term set.

In some embodiments, at least one patient identifier is not detected until the second pass is performed. Consider an example where a free text field of a DICOM header included a patient name that was not detected in performing a respective patient identifier detection function on the free text field of the DICOM header. However, the patient name was successfully identified in the text of the medical report in performing a patient identifier detection function on the medical report. This patient name is added to the blacklist term list, and is detected in a second pass of the free text field of the DICOM header. In response to detection in the second pass, the patient name of the free text field of the DICOM header can be anonymized accordingly to generate a de-identified free text field. Consider a further example where the patient name is included in the image data of the medical scan, but was not detected in performing a respective patient identifier detection function on the free text field of the DICOM header. In the second pass, this patient name can be detected in at least one region of image data of the medical scan by searching the image data for the blacklist term set.

In some embodiments, performing some or all of the patient identifier detection functions includes identifying a set of non-identifying terms, such as the non-identifying subset of fields of the header. In particular, the non-identifying terms can include terms identified as clinical information and/or other terms determined to be preserved. The combined set of non-identifying terms, for example, generated as the union of the sets of sets of non-identifying outputted by performing each patient identifier function, can be used to build a whitelist term set, for example, stored in memory 2806. Performing the second pass can further include identifying at least one non-identifying term of the whitelist term set in the header, medical report, and/or image data of the medical scan, and determining not to anonymize, or to otherwise ignore, the non-identifying term.

In various embodiments, some or all terms of the whitelist term set can be removed from the blacklist term set. In particular, at least one term previously identified as a patient identifier in performing one or more patient identifier detection functions is determined to be ignored and not anonymized in response to determining the term is included in the whitelist term set. This can help ensure that clinically important information is not anonymized, and is thus preserved in the de-identified medical scan and de-identified medical report.

In some embodiments, the second pass can be performed after each of the patient identifier detection functions are performed. For example, performing the anonymization function can include performing this second pass by utilizing the blacklist term set to determine the final set of terms to be anonymized. New portions of text in header fields, not previously detected in generating the first set of patient identifiers or the third set of patient identifiers, can be flagged for anonymization by determining these new portions of text correspond to terms of the blacklist term set. New portions of text the medical report, not previously detected in generating in the second set of patient identifiers, can be flagged for anonymization by determining these new portions of text correspond to terms of the blacklist term set. New regions of the image data of the medical scan, not previously detected in generating the fourth set of patient identifiers, can be flagged for anonymization by determining these new portions of text correspond to terms of the blacklist term set.

In some embodiments, the blacklist term set is built as each patient identifier detection function is performed, and performance of subsequent patient identifier detection functions includes utilizing the current blacklist term set. For example, performing the second patient identifier detection function can include identifying a first subset of the blacklist term set in the medical report by searching the text of the medical report for the blacklist term set and/or by determining if each term in the text of the medical report is included in the blacklist term set. Performing the second patient identifier detection function can further include identifying at least one term in the medical report that is included in the whitelist term set, and determining to ignore the term in response. The first subset can be anonymized to generate the de-identified medical report as discussed herein. New patient identifiers not already found can be appended to the blacklist term set, and the updated blacklist term set can be applied to perform a second search of the header and/or image data of the medical scan, and at least one of the new patient identifiers can be identified in the header in the second search of the header and/or in the image data in a second search of the image data. These newly identified patient identifiers in the header and/or image data are anonymized in generating the de-identified medical scan.

As another example, a second subset of the blacklist term set can be detected in a set of regions of image data of the medical scan by performing the medical scan image analysis function on image data of the medical scan, where the image analysis function includes searching the image data for the set of patient identifiers. For example, the medical scan image analysis function can include searching the image data for text, and the second subset can include detected text that matches one or more terms of the blacklist term set. In some embodiments, detected text that matches one or more terms of the whitelist term set can be ignored. The second subset can be anonymized to generate de-identified image data as discussed herein. New patient identifiers that are detected can be appended to the blacklist term set, and the updated blacklist term set can be applied to perform a second search of the header and/or metadata of the medical scan, and/or can be applied to perform a second search of the medical report. At least one of the new patient identifiers can be identified in the header as a result of performing the second search of the header and/or at least one of the new patient identifiers can be identified medical report as a result of performing the second search of the medical report. These newly identified patient identifiers can be anonymized in the header along with the originally identified blacklist term set in generating the de-identified header, and/or can be anonymized in the medical report along with the originally identified first subset in generating the de-identified medical report.

In some embodiments, the memory 2806 further stores a global blacklist, for example, that includes a vast set of known patient identifying terms. In some embodiments, the global blacklist is also utilized by at least one patient identifier detection function and/or in performing the second pass to determine patient identifying terms for anonymization. In some embodiments, the blacklist term set generated for a particular medical scan and corresponding medical report can be appended to the global blacklist for use in performing the second pass and/or in detecting patient identifiers in subsequently received medical scans and/or medical reports.

Alternatively or in addition, the memory 2806 can further store a global whitelist, for example, that includes a vast set of terms that can be ignored. In particular, the global whitelist can include clinical terms and/or other terms that are deemed beneficial to preserve that do not correspond to patient identifying information. In some embodiments, the global whitelist is utilized by at least one patient identifier detection function and/or in performing the second pass to determine terms to ignore in the header, image data, and/or medical report. In some embodiments, the whitelist term set generated for a particular medical scan and corresponding medical report can be appended to the global whitelist for use in performing the second pass and/or in ignoring terms in subsequently received medical scans and/or medical reports.

Alternatively or in addition, the memory 2806 can further store a global graylist, for example, that includes ambiguous terms that could be patient identifying terms in some contexts, but non-identifying terms in other contexts. For example, "Parkinson" could correspond to patient identifying data if part of a patient name such as "John Parkinson", but could correspond to non-patient identifying data meant to be ignored and preserved in the de-identified medical report and/or de-identified medical scan if part of a diagnosis term such as "Parkinson's disease." In some embodiments, the global graylist is also utilized in performing the second pass and/or in performing at least one patient identifier detection function to determine that a term is included in the graylist, and to further determine whether the term should be added to the blacklist term set for anonymization or whitelist term set to be ignored by leveraging context of accompanying text, by leveraging known data types of a header field from which the term was extracted, by leveraging known structure of the term, by leveraging known data types of a location of the image data from which the term was extracted, and/or by leveraging other contextual information. In some embodiments, the graylist term set can be updated based on blacklist and/or whitelist term sets for a particular medical scan and corresponding medical report.

In some embodiments, the at least one anonymization function includes a fiducial replacement function. For example, some or all of the blacklist term set can be replaced with a corresponding, global fiducial in the header, report data, and/or image data. In some embodiments, the global fiducial can be selected from a set of global fiducials based on a type of the corresponding patient identifier. Each patient identifier detected in the header and/or medical report can be replaced with a corresponding one of the set of global text fiducials. Each patient identifiers detected in the image data can be replaced with a corresponding one of the set of global image fiducials. For example, one or more global image fiducials can overlay pixels of regions of the image data that include the identifying patient data, to obfuscate the identifying patient data in the de-identified image data.

The global text fiducials and/or global image fiducials can be recognizable by inference functions and/or training functions, for example, where the global text fiducials and global image fiducials are ignored when processed in a training step to train an inference function and/or are ignored in an inference step when processed by an inference function. Furthermore, the global text fiducials and/or global image fiducials can be recognizable by a human viewing the header, medical report, and/or image data. For example, a radiologist or other medical professional, upon viewing a header, medical report, and/or image data, can clearly identify the location of a patient identifier that was replaced by the fiducial and/or can identify the type of patient identifier that was replaced by the fiducial.

As an example, the name "John Smith" can be replaced in a header and/or medical report with the text "% PATIENT NAME %", where the text "% PATIENT NAME %" is a global fiducial for name types of the header and/or the text of medical reports. The training step and/or inference step of medical scan natural language analysis functions can recognize and ignore text that matches "% PATIENT NAME %" automatically.

Figure 10B:
FIG. 10B is an illustration of an example of anonymizing patient identifiers in image data of a medical scan in accordance with various embodiments.

FIG. 10B illustrates an example of anonymizing patient identifiers in image data of a medical scan. In this example, the name "John Smith" and the date "May 4, 2010" is detected as freehand text in the original image data of a medical scan. The regions of the image data that include the patient identifiers can each be replaced by global fiducial in the shape of a rectangular bar, or any other shape. As shown in FIG. 10B, a first region corresponding to the location of "John Smith" in the original image data is replaced by fiducial 2820 in the de-identified image data, and a second region corresponding to the location of "May 4, 2010" in the original image data is replaced by fiducial 2822 in the de-identified image data. The size, shape, and/or location of each global visual fiducial can be automatically determined based on the size, shape, and/or location of the region that includes the patient identifier to minimize the amount of the image data that is obfuscated, while still ensuring the entirety of the text is covered. While not depicted in FIG. 10B, the fiducial can be of a particular color, for example, where pixels of the particular color are automatically recognized by the training step and/or inference step of medical scan image analysis functions to indicate that the corresponding region be ignored, and/or where the particular color is not included in the original medical scan and/or is known to not be included in any medical scans. The fiducial can include text recognizable to human inspection such as "% PATIENT NAME" and "% DATE" as depicted in FIG. 10B, and/or can include a QR code, logo, or other unique symbol recognizable to human inspection and/or automatically recognizable by the training step and/or inference step of medical scan image analysis functions to indicate that the corresponding region be ignored.

In some embodiments, other anonymization functions can be performed on different ones of the patient identifying subset of fields to generate the de-identified header, de-identified report data, and/or de-identified image data. For example, based on the type of identifying data of each field of the header, different types of header anonymization functions and/or text anonymization functions can be selected and utilized on the header fields, text of the report, and/or text extracted from the image data. A set of anonymization functions can include a shift function, for example, utilized to offset a date, time or other temporal data by a determined amount to preserve absolute time difference and/or to preserve relative order over multiple medical scans and/or medical reports of a single patient. FIG. 10B depicts an example where the shift function is performed on the date detected in the image data to generate fiducial 2822, where the determined amount is 10 years and 1 month. The determined amount can be determined by the de-identification system randomly and/or pseudo-randomly for each patient and/or for each medical scan and corresponding medical report, ensuring the original date cannot be recovered by utilizing a known offset. In various embodiments, other medical scans and/or medical reports are fetched for the same patient by utilizing a patient ID number or other unique patient identifier of the header. These medial scans and reports can be anonymized as well, where the dates and/or times detected in these medical scans and/or medical reports offset by the same determined amount, randomized or pseudo-randomized for particular patient ID number, for example, based on performing a hash function on the patient ID number.

The set of anonymization functions can include at least one hash function, for example utilized to hash a unique patient ID such as a patient ID number, accession number, and/or SOP instance UID of the header and/or text. In some embodiments, the hashed SOP instance UID, accession number, and/or patient ID number are prepended with a unique identifier, stored in a database of the memory 2806 and/or shared with the entities to which the de-identified medical scans and/or medical reports are transmitted, so that de-identified medical scans and their corresponding de-identified medical reports can be linked and retrieved retroactively. Similarly, longitudinal data can be preserved as multiple medical scans and/or medical reports of the same patient will be assigned the same hashed patient ID.

The set of anonymization functions can further include at least one manipulator function for some types of patient identifiers. Some values of header fields and/or report text that would normally not be considered private information can be considered identifying patient data if they correspond to an outlier value or other rare value that could then be utilized to identify the corresponding patient from a very small subset of possible options. For example, a patient age over 89 could be utilized to determine the identity of the patient, for example, if there are very few patients over the age of 89. To prevent such cases, in response to determining that a patient identifier corresponds to an outlier value and/or in response to determining that a patient identifier compares unfavorably to a normal-range threshold value, the patient identifier can be capped at the normal-range threshold value or can otherwise be manipulated. For example, a normal-range threshold value corresponding to age can be set at 89, and generating a de-identified patient age can include capping patient ages that are higher than 89 at 89 and/or can include keeping the same value for patient ages that are less than or equal to 89.

In some embodiments, the de-identified header data is utilized to replace the corresponding first subset of patient identifiers detected in the medical report with text of the de-identified header fields. In other embodiments, a set of text anonymization functions includes a global text fiducial replacement function, shift function, a hash function, and/or manipulator functions that anonymize the corresponding types of patient identifiers in the medical report separately.

In some embodiments where the image data of a medical scan includes an anatomical region corresponding to a patient's head, the image data may include an identifying facial structure and/or facial features that could be utilized to determine the patient's identity. For example, a database of facial images, mapped to a corresponding plurality of people including the patient, could be searched and a facial recognition function could be utilized to identify the patient in the database. Thus, facial structure included in the image data can be considered patient identifying data.

To prevent this problem and maintain patient privacy, the de-identification system can further be implemented to perform facial obfuscation for facial structure detected in medical scans. At least one region of the image data that includes identifying facial structure can be determined by utilizing a medical image analysis function. For example, the medical image analysis function can include a facial detection function that determines the regions of the image data that include identifying facial structure based on searching the image data for pixels with a density value that corresponds to facial skin, facial bone structure, or other density of an anatomical mass type that corresponds to identifying facial structure, and the facial obfuscation function can be performed on the identified pixels. Alternatively or in addition, the facial detection function can determine the region based on identifying at least one shape in the image data that corresponds to a facial structure.

The image obfuscation function can include a facial structure obfuscation function performed on the medical scan to generate de-identified image data that does not include identifying facial structure. For example, the facial structure obfuscation function can mask, scramble, replace with a fiducial, or otherwise obfuscate the pixels of the region identified by the facial detection function. In some embodiments, the facial structure obfuscation function can perform a one-way function on the region that preserves abnormalities of the corresponding portions of the image, such as nose fractures or facial skin legions, while still obfuscating the identifying facial structure such that the patient is not identifiable. For example, the pixels of the identifying facial structure can be altered such that they converge towards a fixed, generic facial structure. In some embodiments, a plurality of facial structure image data of a plurality of patients can be utilized to generate the generic facial structure, for example, corresponding to an average or other combination of the plurality of faces. For example, the pixels of the generic facial structure can be averaged with, superimposed upon, or otherwise combined with the pixels of the region of the image data identified by the facial detection function in generating the de-identified image data.

In some embodiments, a hash function can be performed on an average of the generic facial structure and the identified facial structure of the image data so that the generic facial structure cannot be utilized in conjunction with the resulting data of the de-identified image data to reproduce the original, identifying facial structure. In such embodiments, the hash function can alter the pixel values while still preserving abnormalities. In some embodiments, a plurality of random, generic facial structures can be generated by utilizing the plurality of facial structure image data, for example, where each if the plurality of facial structure image data are assigned a random or pseudo-random weight in an averaging function utilized to create the generic facial structure, where a new, random or pseudo-random set of weights are generated each time the facial structure obfuscation function is utilized to create a new, generic facial structure to be averaged with the identified facial structure in creating the de-identified image data to ensure the original identifying facial structure cannot be extracted from the resulting de-identified image data.

While facial obfuscation is described herein, similar techniques can be applied in a similar fashion to other anatomical regions that are determined to include patient identifiers and/or to other anatomical regions that can be utilized to extract patient identifying information if not anonymized.

In some embodiments, the at least one receiver 2802 is included in at least one transceiver, for example, enabling bidirectional communication between the medical picture archive system 2620 and/or the report database 2625. In such embodiments, the de-identification system 2800 can generate queries to the medical picture archive system 2620 and/or the report database 2625 for particular medical scans and/or medical reports, respectively. In particular, if the medical scan and medical report are stored and/or managed by separate memories and/or separate entities, they may not be received at the same time. However, a linking identifier, such as DICOM identifiers in headers or metadata of the medical scan and/or medical report, such accession number, patient ID number, SOP instance UID, or other linking identifier that maps the medical scan to the medical report can be utilized to fetch a medical report corresponding to a received medical scan and/or to fetch a medical scan corresponding to a received medical report via a query sent utilizing the at least one transceiver. For example, in response to receiving the medical scan from the medical picture archive system 2620, the de-identification system can extract a linking identifier from a DICOM header of the medical scan, and can query the report database 2625 for the corresponding medical report by indicating the linking identifier in the query. Conversely, in response to receiving the medical report from the report database 2625, the de-identification system can extract the linking identifier from a header, metadata, and/or text body of the medical report, and can query the medical picture archive system 2620 for the corresponding medical scan by indicating the linking identifier in the query. In some embodiments, a mapping of de-identified medical scans to original medical scans, and/or a mapping of de-identified medical reports to original medical reports can be stored in memory 2806. In some embodiments, linking identifiers such as patient ID numbers can be utilized to fetch additional medical scans, additional medical reports, or other longitudinal data corresponding to the same patient.

FIG. 11 presents a flowchart illustrating a method for execution by a de-identification system 2800 that stores executional instructions that, when executed by at least one processor, cause the de-identification to perform the steps below.

Step 2902 includes receiving from a first entity, via a receiver, a first medical scan and a medical report corresponding to the medical scan. Step 2904 includes identifying a set of patient identifiers in a subset of fields of a first header of the first medical scan. Step 2906 includes performing a header anonymization function on each of the set of patient identifiers to generate a corresponding set of anonymized fields. Step 2908 includes generating a first de-identified medical scan by replacing the subset of fields of the first header of the first medical scan with the corresponding set of anonymized fields. Step 2910 includes identifying a first subset of patient identifiers of the set of patient identifiers in the medical report by searching text of the medical report for the set of patient identifiers. Step 2912 includes performing a text anonymization function on the first subset of patient identifiers to generate corresponding anonymized placeholder text for each of the first subset of patient identifiers. Step 2914 includes generating a de-identified medical report by replacing each of the first subset of patient identifiers with the corresponding anonymized placeholder text. Step 2916 includes transmitting, via a transmitter, the de-identified first medical scan and the de-identified medical report to a second entity via a network.

In various embodiments, the medical scan is received from a Picture Archive and Communication System (PACS), where the medical report is received from a Radiology Information System (RIS), and where the first de-identified medical scan and the de-identified medical report are transmitted to a central server that is not affiliated with the PACS or the RIS. In various embodiments, first medical scan and the medical report are stored in a first memory for processing. The first memory is decoupled from the network to prevent the set of patient identifiers from being communicated via the network. The first de-identified medical scan and the de-identified medical report are stored in a second memory that is separate from the first memory. The first de-identified medical scan and the de-identified medical report are fetched from the second memory for transmission to the second entity.

In various embodiments, the header anonymization function performed on each of the set of patient identifiers is selected from a plurality of header anonymization functions based on one of a plurality of identifier types of the corresponding one of the subset of fields. In various embodiments, the plurality of identifier types includes a date type. A shift function corresponding to the date type is performed on a first date of the first header to generate the first de-identified medical scan, where the shift function includes offsetting the first date by a determined amount. A second medical scan is received, via the receiver, that includes a second header. A unique patient ID of the first header matches a unique patient ID of the second header. The shift function is performed on a second date of the second header by offsetting the second date by the determined amount to generate a second de-identified medical scan. The second de-identified medical scan is transmitted to the second entity via the network.

In various embodiments, the plurality of identifier types includes a unique patient ID type. A hash function corresponding the unique patient ID type is performed on the unique patient ID of the first header to generate the first de-identified medical scan. The hash function is performed on the unique patient ID of the second header to generate the second de-identified medical scan. An anonymized unique patient ID field of the first de-identified medical scan matches an anonymized unique patient ID field of the second de-identified medical scan as a result of the unique patient ID of the first header matching the unique patient ID of the second header.

In various embodiments, the plurality of identifier types includes a linking identifier type that maps the medical scan to the medical report. A hash function corresponding to the linking identifier type is performed on a linking identifier of the first header to generate a hashed linking identifier. A linking identifier field of the first de-identified medical scan includes the hashed linking identifier. Performing the text anonymization function on the first subset of patient identifiers includes determining one of the first subset of patient identifiers corresponds to linking identifier text and performing the hash function on the one of the first subset of patient identifiers to generate the hashed linking identifier, where the de-identified medical report includes the hashed linking identifier.

In various embodiments, a second subset of patient identifiers of the set of patient identifiers is identified in a set of regions of image data of the medical scan by performing an image analysis function on image data of the medical scan. The image analysis function includes searching the image data for the set of patient identifiers. An identifier type is determined for each of the second subset of patient identifiers. One of a plurality of image fiducials is selected for each of the second subset of patient identifiers based on the identifier type. De-identified image data is generated, where a set of regions of the de-identified image data, corresponding to the set of regions of the image data, includes the one of the plurality of image fiducials to obfuscate each of the second subset of patient identifiers. Generating the first de-identified medical scan further includes replacing the image data of the medical scan with the de-identified image data.

In various embodiments, a new patient identifier is identified in the medical report by performing a natural language analysis function on the medical report, where new patient identifier is not included in the set of patient identifiers. The set of patient identifiers is updated to include the new patient identifier prior to searching the image data of the medical scan for the set of patient identifiers, and the second subset of patient identifiers includes the new patient identifier.

In various embodiments, the memory further stores a global identifier blacklist. The natural language analysis function includes searching the medical report for a plurality of terms included in the global identifier blacklist to identify the new patient identifier. In various embodiments, the de-identification system determines that the global identifier blacklist does not include one of the set of patient identifiers, and the global identifier blacklist is updated to include the one of the set of patient identifiers.

In various embodiments, performing the image analysis function further includes identifying a new patient identifier in the image data, where new patient identifier is not included in the set of patient identifiers. Identifying text is extracted from a region of the image data corresponding to the new patient identifier. The new patient identifier is identified in the medical report by searching text of the medical report for the identifying text. The text anonymization function is performed on new patient identifier to generate anonymized placeholder text for the new patient identifier. Generating the de-identified medical report further includes replacing the identifying text with the anonymized placeholder text for the new patient identifier.

In various embodiments, generating the de-identified image data further includes detecting an identifying facial structure in the image data of the medical scan. Generating the de-identified image data includes performing a facial structure obfuscation function on the image data, and where the de-identified image data does not include the identifying facial structure.

FIG. 12A illustrates an embodiment of an intensity transform augmentation system 3002. The intensity transform augmentation system 3002 can be utilized to perform density windowing, adjust the brightness or contrast, or otherwise perform at least one intensity transformation function on medical scans of a training set prior to training a computer vision model. A medical scan training set can be received by the intensity transform augmentation system 3002, for example, from medical scan database 342. Transformation function parameter data is also received and/or determined locally. A pre-processing step 3005 utilizes the transformation function parameter data to perform one or more intensity transformation functions, indicated by the transformation function parameter data, on some or all medical scans in the training set to produce at least one augmented image as output of at least one intensity transformation function for some or all of the medical scans in the training set. The augmented images can replace the original medical scans to produce the pre-processed training set, and/or can supplement the original medical scans to produce the pre-processed training set. A training step 3010 can be performed on the pre-processed training set to generate a computer vision model. Model parameters or other data associated with the model can be stored locally for further use, can be sent directly to one or more other subsystems 101 for use, can be sent to a client device 120 for display, and/or can be transmitted for storage in a corresponding medical scan analysis function entry in the medical scan analysis function database 346.

Some or all of the steps and/or processes performed by the intensity transform augmentation system 3002 as discussed herein can be performed automatically, without human intervention. Alternatively or in addition, some or all of the step and/or processed performed by the intensity transform augmentation system 3002 as discussed herein can be performed in response to user input received from a client device, corresponding to user interaction with the client device in response to a prompt displayed by an interface of a display device. Such prompts can be generated by the intensity transform augmentation system 3002 for transmission to the client device.

As shown in FIG. 12A, the intensity transform augmentation system 3002 can communicate bi-directionally, via network 150, with the medical scan database 342, medical scan analysis function database 346, and/or other databases of the database storage system 140, with one or more client devices 120, and/or, while not shown in FIG. 12A, one or more subsystems 101 of FIG. 1. In some embodiments, the intensity transform augmentation system 3002 is an additional subsystem 101 of the medical scan processing system 100, implemented by utilizing the subsystem memory device 245, subsystem processing device 235, and/or subsystem network interface 265 of FIG. 2A. In some embodiments, the intensity transform augmentation system 3002 is implemented by utilizing, or otherwise communicates with, the central server 2640. For example, the model data of one or more computer vision models generated by the intensity transform augmentation system 3002 can be utilized as one or more inference functions sent to the annotating system of the medical picture archive integration system 2600. As another example, some or all of the databases of the database storage system 140 are populated with de-identified data generated by the medical picture archive integration system 2600. In some embodiments, the intensity transform augmentation system 3002 can receive de-identified medical scans, annotation data, and/or reports directly from the medical picture archive integration system 2600. For example, the intensity transform augmentation system 3002 can request de-identified medical scans, annotation data, and/or reports that match requested criteria, for example, corresponding to training set criteria. In some embodiments, some or all of the intensity transform augmentation system 3002 is implemented by utilizing other subsystems 101 and/or is operable to perform functions or other operations described in conjunction with one or more other subsystems 101. In some embodiments, the intensity transform augmentation system 3002 is integrated within and/or utilizes the medical scan image analysis system 112.

The transformation function parameter data is depicted as being retrieved from medical scan analysis function database 346, for example, where some or all intensity transformation functions are stored as medical scan analysis function entries 356 and/or are trained and/or utilized as medical scan analysis functions as described herein. In some embodiments, the transformation function parameter data is stored and/or updated locally. In some embodiments, some or all of the transformation function parameter data is determined based on to user input to a client device 120, for example, in response to a prompt displayed by a display device of the client device, and sent to the intensity transform augmentation system 3002. For example, a user can generate and/or modify one or more intensity transformation functions and/or can select one or more intensity transforms to be utilized from a pre-determined intensity transformation function set. The transformation function parameter data can indicate one or more intensity transformation functions to be applied to the medical scan, as discussed in further detail in FIGS. 12B-12F.

The training step 3010 can correspond to some or all steps of the training step 1352 of FIG. 7A. The training step 3010 can be performed by utilizing the medical scan image analysis system 112. The training step 3010 can include training a neural network or other machine learning model. Output label data can be received in conjunction with the medical scan training set, and can be utilized to train the model. For example, the output label data can be received in conjunction with the medical scan training set, for example, corresponding to annotation data, diagnosis data, report data, metadata of the medical scan, and/or fields of medical scan entries of the medical scans in the training set. The same output label data originally assigned to each medical scan in the training set can be assigned to each corresponding augmented image produced in the pre-processing step for utilization in training step 3010. In some embodiments, the output label is utilized to select the subset of the set of intensity transformation functions that will be applied and/or to otherwise determine one or more of the intensity transformation functions that will be utilized, for example, based on density properties of an abnormality indicated in the output label and/or a region of interest indicated in the output label.

The training set can correspond to the training set data 621 of a corresponding medical scan function entry for the model to be generated. Medical scans to be included in the training set can be determined by the intensity transform augmentation system 3002 based on corresponding criteria for the model to be trained and/or can be indicated via user input to a client device via a user interface displayed on a display device.

The model data can correspond to a computer vision model discussed in conjunction with the medical scan image analysis system 112, discussed with one or more other subsystems as discussed herein, and/or any computer vision model that is trained on medical scan image data and can generate abnormality data or other inference data for new medical scans. In some embodiments, the computer vision model is a neural network.

FIG. 12B illustrates an example of performing pre-processing step 3005. In some embodiments, a single augmented image is generated for each medical scan in the training set by utilizing an intensity transformation function, and the same or different intensity transformation function can be performed on each medical scan. In other embodiments, a plurality of augmented images can be generated for each medical scan in the training set by utilizing a set of intensity transformation functions 1-$n$, where the set of intensity transformation functions are the same or different for each medical scan. In some embodiments, the set of intensity transformation functions includes an identity function, and/or the un-processed image data of the medical scan itself can otherwise be included in the pre-processed training set.

In some embodiments, some or all of the set of intensity transformation functions correspond to one of a plurality of different anatomy features, for example, present in the training set of medical scans. In particular, each intensity transformation function can be based on the density properties of the corresponding anatomy feature, for example, to accentuate the corresponding anatomy feature adjusting a contrast and/or brightness of image data of the one of the training set of medical scans. The different anatomy features can include, for example, air, fat, soft tissue, bone, blood, other fluids, parenchyma, gallstone, and/or foreign body features. Some of the different anatomy features can correspond to abnormalities included in the training set of medical scans. The different anatomy features can correspond to mutually exclusive density value ranges.

The transformation function parameter data can indicate the set of intensity transformation functions, and/or different transform function parameter data can indicate each of the set of intensity transformation functions. The transformation function parameter data can further indicate input conditions for some or all of the set of intensity transformation functions, for example, where a subset of the set of intensity transformation functions are selected from the set to be performed on the medical scan. The input conditions can correspond to scan type or other criteria corresponding to each medical scan, and/or can correspond to randomly generated conditions. For example, the pre-processing step 3005 can include determining a subset of the set of intensity transformation functions to be performed on each medical scan of the training set based on the modality of the medical scan, the anatomical region of the medical scan, the patient history or other patient data corresponding to the medical scan, longitudinal data received along with the medical scan, metadata of the medical scan, density properties of an a anatomical feature included in the medical scan, density properties of an abnormality indicated in diagnosis data or other metadata of the medial scan, density properties of an anatomical feature identified as being of interest, and/or a density value histogram of the medical scan. The scan classifier data 420, diagnosis data 440, and/or other fields of the medical scan entry can be utilized to dictate which subset of functions are utilized.

For example, a first subset of the intensity transformation functions can be determined for a first medical scan of the training set, and a second subset of intensity transformation functions can be determined for a second medical scan of the training set, where the set difference between the first subset and the second subset are non-null. The first and second subset can be selected based on different anatomy features present in different anatomical regions of the first medical scan and second medical scans, respectively. Alternatively or in addition, the first and second subset can be selected based on density properties of different abnormalities indicated in the output label of the first and second medical scans, respectively. Alternatively or in addition, the first and second subset can be selected based on different anatomy features corresponding to different regions of interest indicated in output label of the first and second medical scans, respectively. As another example, the pre-processing step 3005 can include determining some or all of the transformation function parameter data randomly and/or pseudo-randomly in accordance with a uniform distribution or other pre-determined random distribution.

In some embodiments, the input to some or all intensity transformation functions includes a plurality of pixel values of the image data of the medical scan, and the output is a plurality of corresponding pixel values of an augmented image. For example, a plurality of pixels of the image data of the medical scan can each indicate a pixel value, which can correspond to a density value such as a Hounsfield unit value and/or raw sensor data captured in generating the medical scan. In some embodiments, the plurality of pixels of the image data of the medical scan instead correspond to greyscale values, RGB values, or other values in accordance with an image format such as a JPEG format. For example, contrasting parameters and/or density windowing may have already been applied and/or the image data may have been undergone other pre-processing to convert density values to greyscale values. In some embodiments, the input is determined based on the display parameter data 470, for example, based on density window data 475.

In some embodiments, a data format of the intensity transformation function output is different from a data format of the intensity transformation function input. For example, the input can correspond to density values of raw sensor data, and the output can correspond to greyscale values of a JPEG. In other embodiments, the data format of the intensity transformation function output is the same as the image format of the intensity transformation function input. For example, the input can correspond to greyscale values of a JPEG, and the output can correspond to greyscale values of a new JPEG. In such embodiments, the new JPEG can be generated by utilizing the intensity transformation function to alter contrast and/or brightness of the input JPEG, to otherwise re-contrast the JPEG, to apply an image filter to the input JPEG, and/or otherwise alter the pixel values of the input JPEG. Some or all of the set of intensity transformation functions can utilize the same or different type of input format. Some or all of the set of intensity transformation functions can generate the same or different type of output format. In some embodiments, every one of the set of intensity transformation functions produces the same output image format that corresponds to an input image format of the training step 3010 and/or an input image format to the final model generated by the intensity transform augmentation system 3002.

A plurality of pixel values for each of a plurality of pixels of an augmented image can be generated by performing the intensity transformation function on each of the pixel values of each of the plurality of corresponding pixels of the medical scan. Each pixel value can be processed independently of the neighboring pixels, where the output pixel value is a deterministic mapping of input pixel value. The deterministic mapping of the intensity transformation function can be in accordance with a linear function, a piecewise function, a non-linear function, and/or any deterministic function. The deterministic mapping of the intensity transformation function can be a monotonically increasing function. In some embodiments, the intensity transformation function is reversible, and the input medical scan can be regenerated by performing an inverse transformation function. In other embodiments, some input pixel values, such as one or more similar pixel values, are mapped to the same output pixel value, and/or the original input cannot be regenerated.

In some embodiments, some or all medical scans of the training set correspond to medical scans that include a plurality of image slices 412. In such embodiments, each of the set of intensity transformation functions can be performed on all of the plurality of image slices. In such embodiments, each augmented image can include a plurality of augmented image slices. The plurality of augmented image slices produced by a same one of the intensity transformation functions can be grouped together in the same set of augmented image slices to be fed into the model as training data, or can be processed separately.

In some embodiments, the training set includes a plurality of medical studies, and the model is trained on the plurality of medical studies. Each of the plurality of medical studies can include longitudinal data, such as longitudinal data 433, that includes set of medical scans. The same and/or different set of intensity transformation functions can be performed on each medical scan in the longitudinal data of a medical study to produce corresponding augmented longitudinal data that includes a set of augmented images for each of the medical scans in the longitudinal data. Each of the plurality of augmented images produced by a same one of the intensity transformation functions can be grouped together in the same set of augmented longitudinal data to be fed into the model as training data, or can be processed separately.

FIG. 12C illustrates an example intensity transformation function 3050 that utilizes a density windowing function. A density window boundary pair 3052 can designate which subrange of densities within a total range of possible density values are assigned a pixel value in the image data. The density window width 3054 and density window center 3056, are defined by a given density window boundary pair 3052, and similarly, the density window boundary pair 3052 can be determined by a given density window width 3054 and the density window center 3056. Thus, the density window boundary pair 3052, density window width 3054, and/or a density window center 3056 can be utilized as intensity transformation function parameters. In some embodiments, as shown in FIG. 12C, the deterministic mapping is in accordance with a linear function with a an input domain that spans the entirety of density values bounded by the density window boundary pair 3052 and an output range that spans the entirety of possible pixel values and/or is otherwise bounded by a maximum and minimum pixel value. In some embodiments, the density window center 3056 indicates the density value that is mapped to a midpoint value of the span of output pixel values. In some embodiments, density values that are less than the lower bound of the density window boundary pair are mapped to the minimum pixel value, and/or density values that are greater than the upper bound of the density window boundary pair are mapped to the maximum pixel value. In some embodiments, the density windowing corresponds to density windowing techniques discussed in conjunction with the medical scan image analysis system 112.

In some embodiments, the density window for a particular intensity transformation function can be based on the density properties of a corresponding anatomy feature, for example, to accentuate the corresponding anatomy feature. In some embodiments, a known average density value of the anatomy feature is utilized to determine the density window center, for example, where the density window center is set to the known average density value. In some embodiments, a known standard deviation of density of the anatomy feature is utilized to determine the value density window width, where the width is set to a larger value for higher standard deviations. In some embodiments, a density value of an abnormality of an output label for a particular medical scan in the training set and/or average density value of an abnormality classification corresponding to the known abnormality in the medical scan is utilized to determine the density window.

FIGS. 12D-12F illustrate additional examples of intensity transformation functions 3050 that can be utilized in accordance with various embodiments. FIG. 12D illustrates an example where the deterministic mapping is still defined in accordance with a density window boundary pair, but also utilizes a non-linear deterministic mapping within the density window. For example, the non-linear deterministic mapping can be indicated by a mean and a standard deviation included in the transformation function parameter data. Similar to the density window center, the mean can correspond to a input density value that is mapped to the midpoint output pixel value. The standard deviation can indicate how the density values will be distributed across the span of output pixel values in the mapping. Rather than a linear mapping within a density window boundary pair 3052, a deterministic mapping can be in accordance with a cumulative distribution function (CDF) of the normal function as depicted in FIG. 12D, where the density window center is assigned the mean value, and where the density window boundary pair 3052 is assigned to three standard deviations higher and lower than the density window center (or alternatively, the density window width is assigned to six times the standard deviation). As another example where the intensity transformation function is in accordance with a normal distribution, density values that fall within bounds a first standard deviation lower and higher than the mean can be mapped to approximately 68 percent of the output pixel values, centered at the midpoint output pixel value, density values that fall within bounds a second deviation lower and higher than the mean can be mapped to approximately 95 percent of the output pixel values, centered at the midpoint output pixel value, and/or density values that fall within bounds a third standard deviation lower and higher than the mean can be mapped to approximately 99.7 percent of the output pixel values. The non-linear function can be in accordance with a CDF of another distribution that can correspond to a symmetric or skewed distribution, and can be defined by a mean, standard deviation, and/or other parameters of the other distribution indicated in the parameter data.

FIG. 12E illustrates an example where the deterministic mapping of an intensity transformation function 3050 is a non-linear function that spans the entire range of possible density values of the input medical scan, for example, where the entire range of possible density values are utilized and no windowing boundaries are applied. FIG. 12F illustrates an example where the deterministic mapping of an intensity transformation function 3050 is a non-linear function that maps other pixel values, such as greyscale color values of an input image, to pixel values of the output. For example, both the input and output image data of the intensity transformation function 3050 can have a same image format. Some or all of the set of intensity transformation functions **1-*n* can utilize examples illustrated in FIGS. 12C-12F**, and/or can utilize other function types. In some embodiments, every one of the set of intensity transformation functions is a different, deterministic, monotonically increasing mapping of input pixel value to output pixel value. The transformation function parameter data can indicate a CDF, formula, function coefficients, and/or can otherwise indicate and/or define the deterministic mapping of each of the set of intensity transformation functions.

In some embodiments, the transformation function parameter data can indicate desired distribution data of the output pixel values, and the desired distribution data is utilized to determine the deterministic mapping, given the image data of the input medical scan. In particular, the desired distribution data can indicate a shape, distribution parameters such as a distribution function and/or mean and standard deviation, and/or boundary data indicating the desired output histogram of pixel values. While an exact match of the desired distribution data may be unreasonable, defined or predetermined bounds indicating an allowable deviation from the desired distribution can be indicated, and the final distribution of the output histogram can be in accordance with the bounds. In such embodiments, a histogram of the density values and/or other value type of the input pixels is utilized to determine a distribution of the input pixel values. By utilizing this distribution of input pixel values and the desired output distribution, the intensity transformation function 3050 that, when applied to input pixel values of the determined input distribution, generates this desired output distribution. In this fashion, the intensity transformation function can be determined separately for each medical scan, based on their own pixel distribution data. In some embodiments, the desired output histogram is in accordance with a uniform distribution. In other embodiments, the desired output histogram is in accordance with a normal distribution or any other distribution, which can be indicated by a mean, standard deviation, and/or other parameters in the transformation function parameter data.

In some embodiments, such intensity transformation functions 3050 that utilize desired distribution data of the output pixels can be pre-determined, for example, based on pre-determined grouping of scans with similar pixel value histograms. In some embodiments, these pre-determined groupings are grouped by scan type, such as modality, anatomical region, and/or other scan classifier data 420. For example, the pre-determined groupings can be formed in response to determining these scan type groupings have similar density value distributions. In some embodiments, other custom groupings are determined, for example, by utilizing a clustering algorithm. Intensity transformation functions can be generated for an average input pixel distribution of each of these pre-determined groups, where the intensity transformation function generates the desired output distribution for this average input pixel distribution. Some or all of the set of intensity transformation functions 1-$n$ can be generated in this fashion for some or all medical scans in the training set and/or for medical scans processed in accordance with FIG. 12G. Medical scans can be assigned to a most similar one of the groups, for example, by performing a similarity function and/or by utilizing the scan classifier data 420. The pre-determined deterministic mapping for the assigned group can be utilized on the scan in performing the corresponding intensity transformation function.

In some embodiments, some or all of the transformation function parameter data for some or all of the set of intensity transformation function 1-$n$ are determined via user input to client device 120 via interaction with a user interface displayed by a display device. In some embodiments, some or all of the transformation function parameter data for some or all of the set of intensity transformation function 1-$n$ are determined as part of the transform parameter evaluation step discussed in conjunction with FIG. 12H.

In some embodiments, one or more intensity transformation functions are determined randomly. For example, some or all of the intensity transformation function parameters that dictate the deterministic mapping can be generated via a random or pseudo-random process. In particular, for each medical scan in the training set, some or all of the intensity transformation function parameters can be determined randomly, separately, for one or more intensity transformation functions to be performed on each of the medical scans in the training set. For example, the density window boundary pair (or alternatively, the density window center and density window width) of a density window of the intensity transformation function can be determined via a random or pseudo-random selection. As another example, the mean and standard deviation dictating a normal CDF or other CDF of the intensity transformation function can be determined via a random or pseudo-random selection. As another example, a single one, or proper subset of size greater than one, of the set of pre-defined intensity transformation functions 1-$n$ as discussed in FIG. 12B can be selected from the set via a random or pseudo-random selection. As another example, parameters dictating the shape and/or other features of the desired output histogram utilized to generate the intensity transformation function can be determined via a random or pseudo-random selection.

In some embodiments, the random or pseudo-random selection is in accordance with a pre-defined random distribution, which can be the same or different for each of the set of intensity transformation function parameters. The pre-defined random distribution can be uniform, normal, or can be in accordance with another random distribution. For example, for one of the intensity transformation functions that corresponds to a particular anatomical feature, pre-defined mean values for the random selection of some or all parameters can be set based on the density properties of the particular anatomical feature and/or the values of parameters for the corresponding one of the set of intensity transformation functions 1-$n$. Similarly, known density ranges and/or known density variability of the particular anatomical feature can be utilized to determine a pre-defined standard deviation for the random selection of some or all parameters. The random selection of each parameter can correspond to a uniform, normal, or other distribution centered at the pre-defined mean value and/or pre-defined standard deviation value of the corresponding parameter. In some embodiments, the random intensity transformation function parameters are given pre-defined means corresponding to given intensity transformation function parameters and/or learned intensity transform function parameters as discussed in accordance with the FIG. 12H, and normal or other random distribution utilized in random selection of each parameter in accordance with the pre-defined means.

In some embodiments, the random distribution for one or more parameters and/or for selection of one or more intensity transformation functions from the set is determined separately for each medical scan, for example, based on the scan type, anatomical region, and/or other scan classifier data 420 or metadata associated with the medical scan, and each of the parameters are randomly selected in accordance with each determined corresponding random distribution.

In some embodiments, some or all of the intensity transformation function parameters for random selection, and/or some or all of the random distributions dictating random selection of the intensity transformation function parameters, are determined via user input to client device 120 via interaction with a user interface displayed by a display device. In some embodiments, some or all of the intensity transformation function parameters for random selection, and/or some or all of the random distributions dictating random selection of the intensity transformation function parameters, are determined as part of the transform parameter evaluation step discussed in conjunction with FIG. 12H. For example, optimal random distributions for selection of each of the intensity transformation function parameters and/or for selection of one of the set of intensity transformation function can be determined, and the random intensity transformation function parameters utilized for some or all of the training set of medical scans are generated in accordance with the optimal random distribution.

FIG. 12G illustrates an embodiment of an intensity transform augmentation system 3002 that is operable to generate inference data for new medical scans once the model has been generated as discussed in conjunction with FIG. 12A. In this fashion, new medical scans can undergo the same and/or similar pre-processing as the medical scans of the training set utilized to generate the model before being fed into the model themselves. In some embodiment, a different subsystem 101 is responsible for generating inference data for new medical scans.

The intensity transform augmentation system 3002 can receive a new medical scan, for example, not included in the training set, for processing. The medical scan can be retrieved from the same or different medical scan database 342 as the training set, can be received from a client device 120 and/or another subsystem 101, and/or can be otherwise received for processing. A pre-processing step 3006 can be applied to the incoming medical scan. The pre-processing step 3006 can include utilizing transformation function parameter data to produce a pre-processed medical scan from the medical scan. An inference function 3030 can be performed on the pre-processed medical scan by utilizing the computer vision model generated as discussed in FIG. 12 to produce inference data. The inference data can be transmitted to a client device 120 for display via a display device, for example, by utilizing the medical scan assisted review system 102. Alternatively or in addition, the inference data can be transmitted back to the medical scan database 342 to be mapped to the medical scan and/or can be transmitted to one or more other subsystems 101.

The pre-processing step 3006 can the same a pre-processing step 3005. In some embodiments, pre-processing step 3006 includes applying a single intensity transformation function to the medical scan to produce a single augmented image. In some embodiments, pre-processing step 3006 includes selecting the single intensity transformation function from set of intensity transformation functions utilized in pre-processing step 3005, and/or otherwise determining the parameters of the single intensity transformation function. For example, the pre-processing step can include determining the single intensity transformation function based on the scan classifier data 420, modality of the medical scan, the anatomical region of the medical scan, the patient history or other patient data corresponding to the medical scan, longitudinal data received along with the medical scan, metadata of the medical scan, density properties of an a anatomical feature included in the medical scan, density properties of an anatomical feature identified as being of interest, and/or a density value histogram of the medical scan. In some embodiments, the pre-processing step 3006 includes selecting the intensity transformation function based on the random intensity transformation function parameter selection as discussed herein. In some embodiments, the pre-processing step 3006 includes selecting the intensity transformation function based on the density value histogram determined for the image data of the new medical scan and/or based on most similar one of the pre-determined grouping generated based on the scan classifier data, as discussed herein, to generate an augmented image with a desired output distribution. In some embodiments, the pre-processing step 3006 includes determining to apply an identity function and/or includes otherwise leaving the image data of the medical scan unaltered.

The transformation function parameter data utilized by the pre-processing step 3006 can be the same as the transformation function parameter data of pre-processing step 3005, can correspond to a subset of the transformation function parameter data of pre-processing step 3005, for example, corresponding to a single one of the set of intensity transformation functions, and/or can be different from the transformation function parameter data of pre-processing step 3005. The transformation function parameter data can be stored locally, can be fetched from the medical scan analysis function database 346 as shown in FIG. 12G, and/or can otherwise be determined.

The inference function 3030 can be performed by utilizing the computer vision model indicated in the model data to produce inference data. The inference function can utilize the inference step 1354 of FIG. 7B to generate one or more probability matrices 1371 of the inference data. The inference function 3030 can utilize the detection step 1372, abnormality classification step 1374, similar scan identification step 1376, and/or display parameter step 1378 of FIG. 7B in generating the inference data. The display parameter step 1378 can indicate contrast parameters corresponding to the intensity transformation function utilized in performing the pre-processing step 3006. The inference data can correspond to some or all diagnosis data 440 and/or can indicate one or more abnormalities detected in the medical scan. The inference function can correspond to any medical scan analysis function and/or inference function described herein. The model data utilized to perform the inference function can be retrieved from the medical scan analysis function database 346 and/or can be stored locally.

In some embodiments, a subset of the set of intensity transformation functions of size greater than two, are selected in the pre-processing step 3006 in the same fashion as selection in pre-processing step 3005. In some embodiments, the entire set of intensity transformation functions are utilized. The subset or entire set of intensity transformation functions can be applied to the new medical scan to produce a plurality of augmented images. In some embodiments, each of the augmented images are fed into the model separately, and thus inference data is generated for each of the plurality of augmented images. The inference function 3030 can include processing this set of inference data to determine final inference data, for example, by determining consensus inference data across the set of inference data, by performing an average on some or all of the set of inference data, by indicating all of the set of inference data, by indicating different abnormalities indicating in different ones of the set of inference data, by selecting a most severe one of the set of inference data and/or one of the set of inference data indicating a highest probability of one or more abnormalities, and/or by otherwise consolidating the set of inference data.

In other embodiments, performing the training step 3010 includes jointly processing the set of augmented images for each medical scan in the training set as a same set of input data to the model. A set of augmented images for the new medical scan can be generated by performing the same set of intensity transformation functions in pre-processing step 3006, for example, by utilizing the same pre-processing step 3005. Performing the inference function 3030 can include jointly processing this set of augmented images for the new medical scan by feeding the set of augmented images as input to the model to generate the inference data.

FIG. 12H illustrates an embodiment of an intensity transform augmentation system 3002 that is utilized as a contrast parameter learning system. Rather than utilizing a predetermined set of intensity transformation functions and/or random intensity transformation functions as discussed herein, the intensity transform augmentation system 3002 can learn and/or otherwise generate one or more intensity transformation functions to utilize in pre-processing the training data to generate the model and/or in pre-processing new medical scans that are fed into the model in generating inference data.

As shown in FIG. 12H, a transform parameter evaluation step 3070 utilizes model data of a computer vision model to determine significant transformation function parameter data. The significant transformation function parameter data can correspond to one or more intensity transformation function parameters and/or other contrast parameter data determined to be statistically significant, determined to favorably influence the model accuracy, and/or otherwise determined to be utilized to re-train the model to improve the performance of the model. The pre-processing step 3005 can be utilized to generate a pre-processed training set by utilizing the transform parameter data on a medical scan training set, which can be the same or different from the medical scan training set originally used to train the computer vision model. The pre-processed training set can correspond to a re-contrasted version of the training set utilized to train the computer vision model. The pre-processing step 3005 can include performing one or more intensity transformation functions indicated in the significant transformation function parameter data determined in the transform parameter evaluation step 3070 to generate the pre-processed training set, as discussed in conjunction with FIG. 12A. Training step 3010 can be performed by utilizing the pre-processing training set as discussed in conjunction with FIG. 12A to generate an updated computer vision model. The model data of the updated computer vision model can be sent to medical scan function analysis database 346 as a new entry, and/or a new version or otherwise or an updated entry of the previous model. Alternatively or in addition, the significant transformation function parameters can be sent to the medical scan function analysis database 342 as one or more new entries, as one or more new version of one or more existing entries for previous transformation function parameters, and/or as an updated entry of one or more existing entries for previous transformation function parameters.

The updated model data can be utilized by the intensity transform augmentation system itself and/or by other subsystems 101 to generate inference data for new medical scans as discussed in conjunction with FIG. 12G. In some embodiments the significant transformation function parameter data determined in transform parameter evaluation step 3070 can be utilized in performing pre-processing step 3006 on the new medical scans before applying the updated model to generate a pre-processed new medical scan. The pre-processed new medical scan can correspond to a re-contrasted version of the new medical scan received. An updated inference function corresponding to the updated computer vision model can be applied to the pre-processed new medical scan to generate inference data for transmission to a client device as discussed in conjunction with FIG. 12G.

In some embodiments, the significant transformation function parameter data indicates different transformation function parameter data and/or a different one of the set of intensity transformation functions for different sets of medical scan input criteria, such as scan classifier data and/or density value histograms as discussed herein. A single intensity transformation function can be selected based on corresponding features of new medical scan as discussed in conjunction with FIG. 12G. In such embodiments, the significance of this criteria and/or the segmentation of different groupings of medical scan features utilized to determine which one or more intensity transformation function will be utilized on new medical scans can also be generated in the performance of the transform parameter evaluation step 3070.

The model data can correspond to computer vision model generated by the intensity transform augmentation system 3002 itself, for example, in accordance with FIG. 12A. In such cases, the model data can be retrieved from local memory. The model data can correspond to a computer vision model generated by utilizing medical scan image analysis system 112, and/or can correspond to any computer vision model trained on a training set of medical scans. The computer vision model indicated by the model data can have been generated with or without performing a pre-processing step on the a training set of medical scans. In some embodiments, at least one of the set of intensity transformation functions as performed on each medical scan in the training set to produce a pre-processed training set as discussed in conjunction with FIG. 12A. In some embodiments, every one of the set of intensity transformation functions as performed on each medical scan in the training set to produce a pre-processed training set. In some embodiments, the set of intensity transformation functions are selected as a test set of intensity transformation functions and/or an initial set of intensity transformation functions, for example, selected based on user input to a client device for display via a display device.

In some embodiments, performing the transform parameter evaluation step 3070 includes generating a plurality of significance values for each of the set of intensity transformation functions based on evaluating each of their effect on the model. In some embodiments, the set of significance values are ranked, where one or more of the set of intensity transformation functions with a highest ranking are indicated in the significant transformation function parameter data. In some embodiments, the significance values are compared to a significance threshold. For example, the significance threshold can be determined based on user input to client device 120 via interaction with a user interface displayed on a display device. Ones of the set of intensity transformation functions with significance values that compare favorably to the significance threshold can be indicated in the significant transformation function parameter data.

In some embodiments, the means of determining the density window data 475 and/or display parameters 470 as discussed in conjunction with the medical scan image analysis system can be utilized in performing the transform parameter evaluation step 3070. The density window boundary pair (or alternatively, density window center and density window width) of the determined density window and/or contrast parameters indicated in the display parameters can be indicated in the significant transformation function parameter data.

In some embodiments, the model data indicates a plurality of computer vision models. For example, a plurality of computer vision models can be generated by performing a different pre-processing step 3005 one the same training set of medical scans. Each one of the computer vision models can correspond to a pre-processed training set that corresponds to one or more augmented images for each one of the medical scans by utilizing different intensity transformation functions. Some or all of the plurality of computer vision models can be generated by the intensity transform augmentation system 3002 as discussed in conjunction with FIG. 12A.

In some embodiments, the set of computer vision models includes N computer vision models, where each of the set of N computer vision models corresponds to a pre-processed training data that includes augmented images generated by utilizing a single, corresponding one of N different intensity transformation functions on the training data. In such embodiments, determining the significance values can include generating accuracy data based on performing an accuracy step on each computer vision model, for example, where test data is fed into the model and the inference data output is compared to known output labels of the test data to generate the accuracy data. Thus, a model with the most favorable accuracy data can indicate that the corresponding one of the set of intensity transformation functions is of most relative significance, and/or the that the corresponding one of the set of intensity transformation functions can be assigned a highest significance value. In some embodiments, the significance threshold corresponds to an accuracy threshold to which the accuracy data of the corresponding model is compared.

Conversely, each of the set of N computer vision models can correspond to a pre-processed training data that includes augmented images generated by utilizing each of the N possible combinations of N−1 different intensity transformation functions on the training data. Thus, all but one of the set of intensity transformation functions are utilized to generate augmented images utilized in the training set of each model. Accuracy data can similarly be generated for each of these models. In this case, least favorable accuracy data can indicate that the corresponding one of the set of intensity transformation functions that was not included is of most relative significance.

In some embodiments, accuracy differentials between some or all of the models can further indicate whether any of the intensity transformation functions are significant. In some embodiments, a control computer vision model can be generated by utilizing a pre-processed training set, for example where the pre-processed training set is generated by performing all of the set of intensity transformation functions on each of the set of training data. Alternatively or in addition, a control computer vision model can be generated by performing only an identity function, selecting random contrast parameters, and/or otherwise leaving the medical scan image data unaltered in generating the training set utilized to train the model. Alternatively or in addition, a control computer vision model can be generated by utilizing a pre-processed training set generated by utilizing previously determined significant transformation function parameters, for example, as part of an iterative process to further improve performance. Some or all of the additional computer vision models generated by intelligently selecting subsets of the set of intensity transformation functions, and/or by determining random and/or new parameters for a new set of intensity transformation functions, can be considered experimental computer vision models. Accuracy data for the experimental computer vision models can be compared to one or more of the control computer vision models, and/or can be compared to each other. The magnitude of differentials between accuracy data between experimental computer vision models and the one or more control computer vision models can be utilized to determine whether intensity transformation functions that are included and/or that were removed from each experimental computer vision model are statistically significant and/or otherwise influence the model. Experimental computer vision models with accuracy data with highest magnitude differentials from the control can indicate ones of the set of intensity transformation functions that where included and/or removed that have a greatest influence on the model.

In some embodiments, the transform parameter evaluation step 3070 includes an iterative process of tweaking parameters of one or more intensity transformation functions. For example, random or pre-determined parameters for one or more initial intensity transformation functions utilized to pre-process training data is determined. One or more models are generated and evaluated, and one or more of the parameters are changed accordingly, for example, where changes are greater when the parameters are determined to be less significant and when changes are smaller when the parameters are determined to be more significant. Alternatively or in addition, one or more intensity transformation functions are added and/or dropped from the set of intensity transformation functions based on which of the set of intensity transformation functions are determined to be significant. One or models are then regenerated by utilizing the new parameters, and the new parameters are again changed accordingly and/or one or more intensity transformation functions are added and/or dropped from the set of intensity transformation functions accordingly. This process can continue for a fixed number of iterations, until the accuracy data of the one or more models compares favorably to an accuracy threshold, and/or until the significance score of one or more of the intensity transformation functions compares favorably to a threshold. In some embodiments, this iterative process is in accordance with an optimization algorithm and/or a greedy optimization algorithm.

In some embodiments, the transform parameter evaluation step 3070 is inherently incorporated within the training process of the model itself. For example, the model can take density value and/or raw sensor data of the medical scan in an input layer of a neural network, and/or can take greyscale pixel values corresponding to original contrast parameters. A first layer and/or first set of layers can correspond to the pre-processing step, where weights connecting the input layer and first set of layers correspond to performing the intensity transformation function. For example, the weights can indicate the deterministic mapping. A final one of the first set of layers of the neural network can correspond to the pixel values of the augmented image data and/or an otherwise re-contrasted image. Performing the training step 3010 to train the model is utilized to generate the final set of weights corresponding to the learned intensity transformation function, for example, where these weights of the first set of layers are iteratively improved to increase accuracy of the model. In some embodiments, a weights for a plurality of intensity transformation functions are learned in this process, and criteria for which types of medical scans each of the plurality of intensity transformation functions are applied can be learned and/or can be predesignated. In some embodiments, other model types and/or learning methodologies are employed to determine the intensity transformation function and/or to learn a plurality of intensity transformation function to be applied to medical scans that fit a set of predesignated or learned criteria.

In some embodiments, the significant transformation function parameter data indicates that no transformation function parameters were determined to be significant, indicates that no intensity transformation functions out-performed the others, and/or otherwise indicates that the model accuracy is not affected by re-contrasting and/or other intensity transformations. In such embodiments, the intensity transform augmentation system 3002 can determine to keep the original model data, and the re-training is not performed. Similarly, image data of new incoming medical scans can remain unaltered when the inference function is performed. In some embodiments, in response to determining that altering contrast parameters does not significantly affect the model, the model can be re-trained on the original, raw input data, for example, if it had been previously trained on a different image format corresponding to applying contrast parameters to the raw input data. In some embodiments, in response to determining significant transformation function parameter data indicates that no transformation function parameters were determined to be significant, the iterative process of tweaking parameters can be initiated until significant transformation function parameters are determined. This can include re-setting initial parameters to new random initial parameters, prompting the user to set new initial parameters via user input to a user interface, and/or tweaking the current parameters based on their respective performance.

In some embodiments, the intensity transform augmentation system 3002 utilizes a plurality of computer vision models. In particular the plurality of computer vision models can correspond to different medical scan types, different medical scan modalities, different anatomical regions, different patient history, different medical entities, different geographic regions, different types of abnormalities that are detected, and/or other different criteria. In some embodiments, the criteria segmenting the plurality of different computer vision models is based on the scan classifier data 420. In some embodiments, the criteria segmenting the plurality of different computer vision models is determined based on user input to client device 120 via interaction with a user interface displayed on a display device. In some embodiments, the criteria segmenting the plurality of different computer vision models is learned by the intensity transform augmentation system 3002, for example, in conjunction with performing the transform parameter evaluation step 3070. The criteria distinguishing each of the plurality of computer vision models can be utilized to identify corresponding training data utilized to train each model. Furthermore, one of the plurality of computer vision models can be selected to process incoming medical scans based on evaluating the medical scan and/or metadata of the medical scan and determining which of the plurality of computer vision models has corresponding criteria that most favorably compares to the medical scan.

In such embodiments, the training data of each of the plurality of computer vision models can undergo separate pre-processing steps 3005 that utilize different sets of intensity transformation functions and/or different transformation function parameter data corresponding to the same or different types of intensity transformation functions. In some embodiments, set of intensity transformation functions utilized in pre-processing steps 3005 for each of the plurality of computer vision models can be determined based on user input to client device 120 via interaction with a user interface displayed on a display device.

In some embodiments, the set of intensity transformation functions utilized in pre-processing steps 3005 can be determined based on density properties of anatomical features corresponding to the scan type and/or anatomical region of the corresponding one of the plurality of computer vision models. In some embodiments, the set of intensity transformation functions utilized in pre-processing steps 3005 can be determined based on density properties of types of abnormalities that are detected in the scan type and/or anatomical region of the corresponding one of the plurality of computer vision models. In some embodiments, the set of intensity transformation functions utilized in pre-processing steps 3005 can be determined based on density properties of one or more particular types of abnormalities that the corresponding one of the plurality of computer vision models is trained to detect. In some embodiments, different random distributions corresponding to random selection of intensity transformation function parameters are utilized by the different ones of the plurality of computer vision models.

In some embodiments, the set of intensity transformation functions utilized in pre-processing steps 3005 for each of the plurality of computer vision models are determined in accordance with the transform parameter evaluation step 3070 of FIG. 12H. For example, each of the plurality of computer vision models can be processed separately, and different significant transformation function parameter data can be generated for each of the plurality of computer vision models, and determine the indicate the set of intensity transformation functions utilized in pre-processing steps 3005. In some embodiments, determining the criteria that segment different ones of the of computer vision models can also be determined by utilizing the transform parameter evaluation step, for example, as part of an iterative process.

In various embodiments, the intensity transform augmentation system 3002 includes a at least one processor and a memory that stores operational instructions that, when executed by the at least one processor, cause the intensity transform augmentation system to receive, via a receiver, a training set of medical scans. A plurality of sets of augmented images are generated, where each set of augmented images in the plurality of sets of augmented images is generated by performing a set of intensity transformation functions on one of the training set of medical scans, and where each of the set of intensity transformation functions are based on density properties of corresponding one of a plurality of different anatomy features present in the training set of medical scans. A computer vision model is generated by performing a training step on the plurality of sets of augmented images, where each augmented image of a set of augmented images is assigned same output label data based on a corresponding one of the training set of medical scans. A new medical scan is received, via the receiver. Inference data is generated by performing an inference function that utilizes the computer vision model on the new medical scan. The inference data is transmitted, via a transmitter, to a client device for display via a display device.

Alternatively or in addition, the operational instructions, when executed by the at least one processor, cause the intensity transform augmentation system to receive, via the receiver, a training set of medical scans. Random intensity transformation function parameters are generated for each medical scan of the training set of medical scans. A plurality of augmented images are generated, where each of the plurality of augmented images is generated by performing a intensity transformation function on one of the training set of medical scans by utilizing the random intensity transform parameters generated for the one of the training set of medical scan. A computer vision model is generated by performing a training step on the plurality of augmented images. A new medical scan is received via the receiver. Inference data is generated by performing an inference function that utilizes the computer vision model on the new medical scan. The inference data is transmitted, via the transmitter, to a client device for display via a display device.

Alternatively or in addition, the intensity transform augmentation system is implemented as a contrast parameter learning system. The operational instructions, when executed by the at least one processor, cause the contrast parameter learning system to generate contrast significance data for a computer vision model, where the computer vision model was generated by performing a training step on a training set of medical scans. Significant contrast parameters are identified based on the contrast significance data. A re-contrasted training set is generated by performing an intensity transformation function on the training set of medical scans, where the intensity transformation function utilizes the significant contrast parameters. A re-trained model is generated by performing the training step on the first re-contrasted training set. A new medical scan is received via the receiver. Re-contrasted image data of the new medical scan is generated by performing the intensity transformation function. Inference data is generated by performing an inference function that utilizes the first re-trained model on the re-contrasted image data. The inference data is transmitted via the transmitter to a client device for display via a display device.

FIG. 13 presents a flowchart illustrating a method for execution by an intensity transform augmentation system 3002 that stores executional instructions that, when executed by at least one processor, cause the intensity transform augmentation system 3002 to perform the steps below.

Step 3102 includes receiving, via a receiver, a training set of medical scans. Step 3104 includes generating a plurality of sets of augmented images. Each set of augmented images in the plurality of sets of augmented images is generated by performing a set of intensity transformation functions on one of the training set of medical scans. Each of the set of intensity transformation functions can be based on density properties of corresponding one of a plurality of different anatomy features present in the training set of medical scans. For example, the plurality of different anatomy features can include bone, soft tissue, fat, fluid, and/or air.

Step 3106 includes generating a computer vision model by performing a training step on the plurality of sets of augmented images. Each augmented image of the set of augmented images is assigned same output label data based on a corresponding one of the training set of medical scans. Step 3108 includes receiving, via the receiver, a new medical scan. Step 3110 includes generating inference data by performing an inference function that utilizes the computer vision model on the new medical scan. Step 3112 includes transmitting, via a transmitter, the inference data to a client device for display via a display device.

In various embodiments, performing one of the set of intensity transformation functions on the one of the training set of the medical scans includes adjusting a contrast of image data of the one of the training set of medical scans to accentuate the corresponding one of the plurality of different anatomy features. In various embodiments, performing one of the set of intensity transformation functions on the one of the training set of the medical scans includes adjusting a brightness of image data of the one of the training set of medical scans to accentuate the corresponding one of the plurality of different anatomy features.

In various embodiments, the training set of medical scans includes a first subset of medical scans that corresponds to a first anatomical region and a second subset of medical scans that corresponds to a second anatomical region. A first proper subset of the set of intensity transformation functions is applied to medical scans of the first subset based on a first subset of the plurality of different anatomy features present in the first anatomical region. A second proper subset of the set of intensity transformation functions is applied to medical scans of the second subset based a second subset of the plurality of different anatomy features present in the second anatomical region. A set difference between the first proper subset of the set of intensity transformation functions and the second proper subset of the set of intensity transformation functions is non-null.

In various embodiments, the training set of medical scans includes a first subset of medical scans that corresponds to a first abnormality output label and a second subset of medical scans that corresponds to a second abnormality output label. A first proper subset of the set of intensity transformation functions is applied to medical scans of the first subset based on first density properties of the first abnormality output label. A second proper subset of the set of intensity transformation functions is applied to medical scans of the second subset based on second density properties of the second abnormality output label. A set difference between the first proper subset of the set of intensity transformation functions and the second proper subset of the set of intensity transformation functions is non-null.

In various embodiments, the training set of medical scans includes a first subset of medical scans that corresponds to a first region of interest output label and a second subset of medical scans that corresponds to a second region of interest output label. A first proper subset of the set of intensity transformation functions is applied to medical scans of the first subset based on a first subset of the plurality of different anatomy features that correspond to the first region of interest output label, and a second proper subset of the set of intensity transformation functions is applied to medical scans of the second subset based on a second subset of the plurality of different anatomy features that correspond to the second region of interest output label. A set difference between the first proper subset of the set of intensity transformation functions and the second proper subset of the set of intensity transformation functions is non-null.

In various embodiments, the set of intensity transformation functions is performed on image data of the training set of medical scans to produce the plurality of sets of augmented images. Generating the computer vision model includes performing the training step on the image data of the training set of medical scans and the plurality of sets of augmented images. In various embodiments, each of the set of intensity transformation functions is performed on raw sensor data of one of the training set of medical scans to generate one of a corresponding set of augmented images. In various embodiments, the raw sensor data is in a first data format and the one of the corresponding set of augmented images is in a second data format. In various embodiments, the second data format is a JPEG image format.

In various embodiments, performing each of the set of intensity transformation functions includes calculating each one of a plurality of pixel values of the augmented image as a deterministic function of each corresponding one of a plurality of density values of the raw sensor data. In various embodiments, the deterministic function utilized by at least one of the set of intensity transformation functions is a non-linear function of density value. In various embodiments, some or all of the intensity transformation functions utilize a deterministic function of density value in accordance with a different mean and different standard deviation of a cumulative distribution function of a normal distribution.

In various embodiments, some or all of the set of intensity transformation functions is in accordance with a different density window boundary pair. In various embodiments, some or all of the set of intensity transformation functions is in accordance with a different density window center. In various embodiments, some or all of the set of intensity transformation functions is in accordance with a different density window width.

In various embodiments, function parameter data is received from a client device. The function parameter data corresponds to user input in response to a prompt displayed via a user interface on a display device that corresponds to the client device. At least one of the set of intensity transformation functions is performed in accordance with the function parameter data.

In various embodiments, the same output label data indicates known abnormality data of the corresponding one of the training set of medical scans, and the inference data indicates at least one abnormality detected in the new medical scan.

In various embodiments, each medical scan of the training set of medical scans includes a set of image slices. The set of intensity transformation functions is performed on each of the set of image slices on one of the training set of medical scans to generate a corresponding set of augmented images of the plurality of sets of augmented images. In various embodiments, the training set of medical scans includes a plurality of longitudinal data sets that each include a plurality of medical scans. The set of intensity transformation functions is performed on each of the plurality of longitudinal data sets to generate a corresponding longitudinal set of augmented images of the plurality of sets of augmented images.

FIG. 14 presents a flowchart illustrating a method for execution by an intensity transform augmentation system 3002 that stores executional instructions that, when executed by at least one processor, cause the intensity transform augmentation system 3002 to perform the steps below. Some or all steps of FIG. 14 can be performed by the intensity transform augmentation system 3002 alternatively or in addition to some or all of the steps of FIG. 13.

Step 3202 includes receiving, via a receiver, a training set of medical scans. Step 3204 includes generating random intensity transformation function parameters for each medical scan of the training set of medical scans. Step 3206 includes generating a plurality of augmented images, where each of the plurality of augmented images is generated by performing a intensity transformation function on one of the training set of medical scans by utilizing the random intensity transformation parameters generated for the one of the training set of medical scans. Step 3208 includes generating a computer vision model by performing a training step on the plurality of augmented images. Step 3210 includes receiving, via the receiver, a new medical scan. Step 3212 includes generating inference data by performing an inference function that utilizes the computer vision model on the new medical scan. Step 3214 includes transmitting, via a transmitter, the inference data to a client device for display via a display device.

In various embodiments, generating the computer vision model includes performing the training step on image data of each of the training set of medical scans and the plurality of augmented images.

In various embodiments, performing the intensity transformation function on the one of the training set of medical scans includes calculating each one of a plurality of greyscale pixel values of the augmented image as a deterministic function of each corresponding one of a plurality of density values of raw sensor data of the one of the training set of medical scans. In various embodiments, performing the intensity transformation function on the one of the training set of medical scans includes calculating each one of a final plurality of greyscale pixel values of the augmented image as a deterministic function of each corresponding one of an initial plurality of greyscale pixel values of image data of the one of the training set of medical scans. In various embodiments, generating the computer vision model includes performing the training step on image data of each the training set of medical scans and the plurality of augmented images.

In various embodiments, generating the random intensity transform parameters includes randomly selecting a density window center and a density window boundary pair. The intensity transformation function is a density windowing function defined by the density window center and the density window boundary pair. In various embodiments, the random intensity transformation function is a non-linear function defined by the random intensity transform parameters. In various embodiments, generating the random intensity transform parameters includes randomly selecting a mean value and further includes randomly selecting a standard deviation value. The intensity transformation function is performed in accordance with the mean value and the standard deviation value. In various embodiments, performing the intensity transformation function on the one of the training set of medical scans includes calculating each one of a final plurality of pixel values of the augmented image as a deterministic function of each corresponding one of an initial plurality of pixel values of the one of the training set of medical scans, where the deterministic function is a cumulative distribution function of a normal distribution designated by the mean value and the standard deviation value.

In various embodiments, a final histogram indicating an occurrence of pixel values for each of the plurality of augmented images reflects the mean value and the standard deviation value. In various embodiments, an initial histogram indicating an occurrence of pixel values for the one of the training set of medical scans is utilized to determine the random intensity transformation function such that the final histogram reflects the mean value and the standard deviation value.

In various embodiments, the random intensity transformation function parameters are selected randomly from a discrete set of pre-determined parameter options. In various embodiments, the random intensity transformation function parameters are generated in accordance with a non-uniform random distribution. In various embodiments, an optimal random distribution for parameter selection is determined. The random intensity transformation function parameters for all of the training set of medical scans are generated in accordance with the optimal random distribution. In various embodiments random distribution parameter data is received from a client device. The random distribution parameter data corresponds to user input in response to a prompt displayed via a user interface on a display device that corresponds to the client device. The non-uniform random distribution utilized to generate the random intensity transformation function parameters corresponds to the random distribution parameter data.

In various embodiments, a set of random distributions for parameter selection are determined. selecting one of the set of random distributions is selected for each medical scan of the training set of medical scans, based on a metadata or other characteristics of each medical scan of the training set of medical scans. The random intensity transformation function parameters are generated for the corresponding medical scan in accordance with the one of the set of random distributions.

In various embodiments, a set of augmented images are generated for each of the training set of medical scans, and the random intensity transformation function parameters are generated separately for utilization in performing the intensity transformation function on the each of the training set of medical scans to generate each of the set of augmented images. In various embodiments a set of random distributions for parameter selection are determined. The random intensity transformation function parameters are generated in accordance with each of the set of random distributions for the each of the training set of medical scans to generate the set of augmented images. In various embodiments, the set of random distributions each have mean parameter values corresponding to one of a set of windowing functions. In various embodiments, each of the set of windowing functions is based on density properties of a corresponding one of a plurality of different anatomy features.

In various embodiments, a set of output label data corresponding to the training set of medical scans indicates known abnormality data of the training set of medical scans, performance of the training step utilizes the set of output label data, and the inference data indicates at least one abnormality detected in the new medical scan.

FIG. 15 presents a flowchart illustrating a method for execution by an intensity transform augmentation system 3002 for example, implemented as a contrast parameter learning system. The intensity transform augmentation system 3002 stores executional instructions that, when executed by at least one processor, cause the intensity transform augmentation system 3002 to perform the steps below. Some or all steps of FIG. 15 can be performed by the intensity transform augmentation system 3002 alternatively or in addition to some or all of the steps of FIG. 13 and/or FIG. 14.

Step 3302 includes generating first contrast significance data for a first computer vision model, where the computer vision model was generated by performing a training step on a first training set of medical scans. Step 3304 includes identifying first significant contrast parameters based on the first contrast significance data. Step 3306 includes generating a first re-contrasted training set by performing a first intensity transformation function on the first training set of medical scans, where the first intensity transformation function utilizes the first significant contrast parameters. Step 3308 includes generating a first re-trained model by performing the training step on the first re-contrasted training set. Step 3310 includes receiving, via a receiver, a new medical scan. Step 3312 includes generating re-contrasted image data of the new medical scan by performing the first intensity transformation function. Step 3314 includes generating inference data by performing an inference function that utilizes the first re-trained model on the re-contrasted image data. Step 3316 includes transmitting, via a transmitter, the inference data to a client device for display via a display device.

In various embodiments, the first training set of medical scans corresponds to a first one of a plurality of medical scan types. Second contrast significance data is generated for a second computer vision model, where the second computer vision model was generated by performing the training step on a second training set of medical scans that correspond to a second one of a plurality of medical scan types that is different from the first one of the plurality of medical scan types. Second significant contrast parameters are identified based on the second contrast significance data, where the second significant contrast parameters are different from the first significant contrast parameters. A second re-contrasted training set is generated by performing a second intensity transformation function on a the second training set of medical scans, where the second intensity transformation function utilizes the second significant contrast parameters. A second re-trained model is generated by performing the training step on the second re-contrasted training set. The first intensity transformation function and the inference function that utilizes the first re-trained model is utilized for the new medical scans in response to determining the new medical scan corresponds to the first one of the plurality of medical scan types.

In various embodiments, the first one of the plurality of medical scan types and the second one of the plurality of medical scan types correspond to different anatomical regions. In various embodiments, the first one of the plurality of medical scan types and the second one of the plurality of medical scan types correspond to different modalities.

In various embodiments, first intensity transformation function is a non-linear function. In various embodiments, the first significant contrast parameters indicate a mean and a standard deviation utilized to perform the non-linear function on each of a plurality of pixels to produce re-contrasted image data. In various embodiments, the non-linear function is a CDF corresponding to a normal distribution. In various embodiments, the first significant contrast parameters indicate a density window boundary pair.

In various embodiments a plurality of sets of augmented images are generated. Each set of augmented images in the plurality of sets of augmented images is generated by performing a set of intensity transformation functions on one of the first training set of medical scans. In various embodiments, each of the set of intensity transformation functions are based on density properties of corresponding one of a plurality of different anatomy features present in the training set of medical scans. The first computer vision model is generated by performing the training step on the plurality of sets of augmented images, where each augmented image of a set of augmented images is assigned same output label data based on a corresponding one of the training set of medical scans. In various embodiments, significant contrast parameters utilized to perform the first intensity transformation function correspond to contrast parameters utilized by a corresponding one of the set of intensity transformation functions. In various embodiments, the first contrast significance data indicates a ranking of the set of intensity transformation functions, and the first significant contrast parameters are identified to correspond to the contrast parameters utilized by the one of the set of intensity transformation functions in response to the one of the set of intensity transformation functions having a most favorable rank in the ranking.

In various embodiments, the first contrast significance data indicates a proper subset of the set of intensity transformation functions that includes at least two of the set of intensity transformation functions. The first re-contrasted training set is generated by performing a the proper subset of intensity transformation function on the first training set of medical scans to generate a plurality of sets of augmented images. The first re-trained model is generated by performing the training step on the plurality of sets of augmented images. In various embodiments, significance values are calculated for each of the set of intensity transformation functions. A significant significant subset of the set of intensity transformation functions is generated by including ones of the set of intensity transformation functions with a corresponding significance value that compares favorably to a significance threshold. The proper subset corresponds to the significant subset.

In various embodiments, the re-contrasted image data of the new medical scan includes a set of images, generated by performing the proper subset of the set of intensity transformation functions on the new medical scan. Generating the inference data includes performing the inference function on the set of images the re-contrasted image data to generate a set of partial inference data. A consensus function is performed on the set of partial inference data to generate the inference data.

In various embodiments, a plurality of sets of augmented images are generated. Each set of augmented images in the plurality of sets of augmented images is generated by performing a set of intensity transformation functions on one of the first training set of medical scans. A set of computer vision models are generated that each correspond to one of the set of intensity transformation functions. Each of the set of computer vision models is generated by performing the training step on ones of the plurality of sets of augmented images that were generated by utilizing the corresponding one of the set of the intensity transformation functions. Model accuracy data is generated for each of the set of computer vision models. Model ranking data is generated by ranking the set of computer vision models in accordance with the model accuracy data. The first contrast significance data indicates the one of the set of intensity transformation functions that corresponds to a most favorably ranked one of the set of computer vision models in the model ranking data.

In various embodiments, the first contrast significance data is generated by calculating significance values for each of a set of contrast parameters that each correspond to contrast settings for at least one of the medical scans of the first training set. Ones of the set of contrast parameters with a corresponding significance value that compares favorably to a significance threshold are indicated in the first contrast significance data. In various embodiments, none of the set of contrast parameters have a corresponding significance value that compares favorably to the significance threshold, and where the first intensity transformation function corresponds to an identity function in response to the first contrast significance data indicating no significant contrast parameters.

In various embodiments, the set of contrast parameters correspond to a set of intensity transformation functions applied to the medical scans of the training set, and none of the set of contrast parameters have a corresponding significance value that compares favorably to the significance threshold. A new set of contrast parameters are selected. An updating training set of medical scans are generated by performing a new set of intensity transformation functions that utilize the new set of contrast parameters on the training set of medical scans. The training step is re-performed on a the updated training set of medical scans to generate an updated first computer vision model. Updated first contrast significance data is generated for the updated first computer vision model, where the first significant contrast parameters are identified based on the updated first contrast significance data, and where the first significant contrast parameters include contrast parameters of the new set of contrast parameters.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may further be used herein, the term "associated with", includes direct and/or indirect coupling of separate items and/or one item being embedded within another item. As may still further be used herein, the term "automatically" refers to an action caused directly by a processor of a computer network in response to a triggering event and particularly without human interaction.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", "processing device" and/or "processing unit" may be a single processing device or a plurality of processing devices. Such a processing device may be a microprocessor, micro-controller, digital signal processor, graphics processing unit, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures and/or described herein. Such a memory device or memory element can be included in an article of manufacture. While the processing module, module, processing circuit, and/or processing unit device may be a general purpose computing device, the execution of the hard coded and/or operational instructions by the processing module, module, processing circuit, and/or processing unit configures such a general purpose computing device as a special purpose computing device to implement the corresponding steps and/or functions illustrated in one or more of the Figures and/or described herein. In particular, the hard coded and/or operational instructions by the processing module, module, processing circuit, and/or processing unit implement acts and algorithms performed by the processing module, module, processing circuit, and/or processing unit. Such acts and algorithms can be identified by name, can be illustrated via flowchart and/or described in words.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The term "system" is used in the description of one or more of the embodiments. A system implements one or more functions via a device such as a processor or other processing device or other hardware that may include or operate in association with a memory that stores operational instructions. A system may operate independently and/or in conjunction with software and/or firmware. As also used herein, a system may contain one or more sub-system, each of which may be one or more systems.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. An intensity transformation augmentation system, comprising:
    at least one processor; and
    a memory that stores operational instructions that, when executed by the at least one processor, cause the intensity transformation augmentation system to:
        receive a training set of medical scans, wherein the training set of medical scans includes a first subset of medical scans that corresponds to a first anatomical region and a second subset of medical scans that corresponds to a second anatomical region;

generate a plurality of sets of augmented images, wherein each set of augmented images in the plurality of sets of augmented images is generated by performing a set of intensity transformation functions on one of the training set of medical scans, wherein each of the set of intensity transformation functions are based on density properties of corresponding one of a plurality of different anatomy features present in the training set of medical scans wherein a first proper subset of the set of intensity transformation functions is applied to medical scans of the first subset based on a first subset of the plurality of different anatomy features present in the first anatomical region, wherein a second proper subset of the set of intensity transformation functions is applied to medical scans of the second subset based a second subset of the plurality of different anatomy features present in the second anatomical region, and wherein a set difference between the first proper subset of the set of intensity transformation functions and the second proper subset of the set of intensity transformation functions is non-null;

generate a computer vision model by performing a training step on the plurality of sets of augmented images, wherein each augmented image of a set of augmented images is assigned same output label data based on a corresponding one of the training set of medical scans;

receive a new medical scan;

generate inference data by performing an inference function that utilizes the computer vision model on the new medical scan; and transmit the inference data to a client device for display via a display device.

2. The intensity transform augmentation system of claim 1, wherein the plurality of different anatomy features include bone, soft tissue, fat, fluid, and air.

3. The intensity transform augmentation system of claim 1, wherein performing one of the set of intensity transformation functions on the one of the training set of the medical scans includes adjusting a contrast of image data of the one of the training set of medical scans to accentuate the corresponding one of the plurality of different anatomy features.

4. The intensity transform augmentation system of claim 1, wherein performing one of the set of intensity transformation functions on the one of the training set of the medical scans includes adjusting a brightness of image data of the one of the training set of medical scans to accentuate the corresponding one of the plurality of different anatomy features.

5. The intensity transform augmentation system of claim 1, wherein the training set of medical scans includes a third subset of medical scans that corresponds to a first abnormality output label and a fourth subset of medical scans that corresponds to a second abnormality output label, wherein a third proper subset of the set of intensity transformation functions is applied to medical scans of the third subset based on first density properties of the first abnormality output label, wherein a fourth proper subset of the set of intensity transformation functions is applied to medical scans of the fourth subset based on second density properties of the second abnormality output label, and wherein a set difference between the third proper subset of the set of intensity transformation functions and the fourth proper subset of the set of intensity transformation functions is non-null.

6. The intensity transform augmentation system of claim 1, wherein the training set of medical scans includes a third subset of medical scans that corresponds to a first region of interest output label and a fourth subset of medical scans that corresponds to a second region of interest output label, wherein a third proper subset of the set of intensity transformation functions is applied to medical scans of the third subset based on a first subset of the plurality of different anatomy features that correspond to the first region of interest output label, wherein a fourth proper subset of the set of intensity transformation functions is applied to medical scans of the fourth subset based on a second subset of the plurality of different anatomy features that correspond to the second region of interest output label, and wherein a set difference between the third proper subset of the set of intensity transformation functions and the fourth proper subset of the set of intensity transformation functions is non-null.

7. The intensity transform augmentation system of claim 1, wherein the set of intensity transformation functions is performed on image data of the training set of medical scans to produce the plurality of sets of augmented images, and wherein generating the computer vision model includes performing the training step on the image data of the training set of medical scans and the plurality of sets of augmented images.

8. The intensity transform augmentation system of claim 1, wherein each of the set of intensity transformation functions is performed on raw sensor data of one of the training set of medical scans to generate one of a corresponding set of augmented images.

9. The intensity transform augmentation system of claim 8, wherein the raw sensor data is in a first data format and wherein the one of the corresponding set of augmented images is in a second data format.

10. The intensity transform augmentation system of claim 9, wherein the second data format is a JPEG image format.

11. The intensity transform augmentation system of claim 8, wherein performing each of the set of intensity transformation functions includes calculating each one of a plurality of pixel values of the augmented image as a deterministic function of each corresponding one of a plurality of density values of the raw sensor data.

12. The intensity transform augmentation system of claim 11, wherein the deterministic function utilized by at least one of the set of intensity transformation functions is a non-linear function of density value.

13. The intensity transform augmentation system of claim 12, wherein the deterministic function utilized by at least one of the set of intensity transformation functions is in accordance with a cumulative distribution function of density value, and wherein the cumulative distribution function is in accordance with a normal distribution.

14. The intensity transform augmentation system of claim 1, wherein each of the set of intensity transformation functions is in accordance with a different density window boundary pair.

15. The intensity transform augmentation system of claim 1, wherein the operational instructions, when executed by the at least one processor, further cause the intensity transformation augmentation system to:

receive function parameter data from a client device, wherein the function parameter data corresponds to user input in response to a prompt displayed via a user interface on a display device that corresponds to the client device; and perform at least one of the set of intensity transformation functions in accordance with the function parameter data.

16. The intensity transform augmentation system of claim 1, wherein the same output label data indicates known abnormality data of the corresponding one of the training set of medical scans, and wherein the inference data indicates at least one abnormality detected in the new medical scan.

17. The intensity transform augmentation system of claim 1, wherein each medical scan of the training set of medical scans includes a set of image slices, and wherein the set of intensity transformation functions is performed on each of the set of image slices on one of the training set of medical scans to generate a corresponding set of augmented images of the plurality of sets of augmented images.

18. The intensity transform augmentation system of claim 1, wherein the training set of medical scans includes a plurality of longitudinal data sets that each include a plurality of medical scans, wherein the set of intensity transformation functions is performed on each of the plurality of longitudinal data sets to generate a corresponding longitudinal set of augmented images of the plurality of sets of augmented images.

19. A method for execution by an intensity transform augmentation system, comprising:
- receiving a training set of medical scans, wherein the training set of medical scans includes a first subset of medical scans that corresponds to a first anatomical region and a second subset of medical scans that corresponds to a second anatomical region;
- generating a plurality of sets of augmented images, wherein each set of augmented images in the plurality of sets of augmented images is generated by performing a set of intensity transformation functions on one of the training set of medical scans, wherein each of the set of intensity transformation functions are based on density properties of corresponding one of a plurality of different anatomy features present in the training set of medical scans wherein a first proper subset of the set of intensity transformation functions is applied to medical scans of the first subset based on a first subset of the plurality of different anatomy features present in the first anatomical region, wherein a second proper subset of the set of intensity transformation functions is applied to medical scans of the second subset based a second subset of the plurality of different anatomy features present in the second anatomical region, and wherein a set difference between the first proper subset of the set of intensity transformation functions and the second proper subset of the set of intensity transformation functions is non-null;
- generating a computer vision model by performing a training step on the plurality of sets of augmented images, wherein each augmented image of a set of augmented images is assigned same output label data based on a corresponding one of the training set of medical scans;
- receiving a new medical scan;
- generating inference data by performing an inference function that utilizes the computer vision model on the new medical scan; and
- transmitting the inference data to a client device for display via a display device.

20. The method of claim 19, wherein performing one of the set of intensity transformation functions on the one of the training set of the medical scans includes adjusting at least one of:
- a contrast of image data of the one of the training set of medical scans, or
- a brightness of image data of the one of the training set of medical scans, to accentuate the corresponding one of the plurality of different anatomy features.

* * * * *